US008058257B2

(12) United States Patent
Tan et al.

(10) Patent No.: US 8,058,257 B2
(45) Date of Patent: *Nov. 15, 2011

(54) COMPOSITIONS AND METHODS FOR INHIBITING EXPRESSION OF A GENE FROM THE JC VIRUS

(75) Inventors: Pamela Tan, Kulmbach (DE); Dinah Sah, Boston, MA (US); Birgit Bramlage, Kulmbach (DE)

(73) Assignee: Alnylam Pharmaceuticals, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/720,465

(22) Filed: Mar. 9, 2010

(65) Prior Publication Data

US 2010/0227915 A1   Sep. 9, 2010

Related U.S. Application Data

(63) Continuation of application No. 11/741,205, filed on Apr. 27, 2007, now Pat. No. 7,691,824.

(60) Provisional application No. 60/795,765, filed on Apr. 28, 2006.

(51) Int. Cl.
*A61K 48/06* (2006.01)
*C07H 21/04* (2006.01)
*C12N 15/00* (2006.01)

(52) U.S. Cl. ...... 514/44; 536/24.4; 435/625; 435/320.1; 435/458

(58) Field of Classification Search .................. None
See application file for complete search history.

(56) References Cited

U.S. PATENT DOCUMENTS 7,691,824 B2 * 4/2010 Tan et al. ............... 514/44 R
2003/0143732 A1   7/2003 Fosnaugh et al.
2004/0259247 A1  12/2004 Tuschl et al.
2007/0004664 A1   1/2007 McSwiggen et al.
2007/0031844 A1   2/2007 Khvorova et al.

OTHER PUBLICATIONS

Agrawal, S., et al., "Antisense oligonucleotides: towards clinical trials." Trends in Biotechnology. Oct. 1996, vol. 14, pp. 376-387.
Bass, B., "The short answer," Nature, May 24, 2001, pp. 428-429, vol. 411.
Elbashir, S., et al., "Analysis of gene function in somatic mammalian cells using small interfering RNAs," Methods, 2002, pp. 199-213, vol. 26.
Elbashir, S., et al., "Duplexes of 21-nucleotide RNAs mediate RNA interference in mammalian cell culture," Nature, May 24, 2001, p. 494-498, vol. 411.
Elbashir, S., et al., "Functional Anatomy of siRNAs for Mediating Efficient RNAi in *Drosophila melanogaster* Embryo Lysate", The EMBO Journal, 2001, pp. 6877-6888, vol. 20, No. 23.
Elbashir, S., et al., "RNA Interference is Mediated by 21-and 22 Nucleotide RNAs," Genes & Development, 2001, pp. 188-200, vol. 15.
Fire, A., "RNA-triggered Gene Silencing," Trends in Genetics, Sep. 1999, pp. 358-363, vol. 15, No. 9.
Fire, A., et al., "Potent and Specific Genetic Interference by Double Stranded RNA in *Caenorhabditis elegans*," Nature, Feb. 19, 1998, pp. 806-811, vol. 391.
Tuschl, T., "Functional genomics: RNA sets the standard," Nature, Jan. 16, 2003, vol. 421, No. 6920, pp. 220-221.
Tuschl T., "RNA Interference and Small Interfering RNAs" Chembiochem, 2001, pp. 239-245, vol. 2.
Tuschl, T., et al., "Small Interfering RNAs: A Revolutionary Tool for the Analysis of Gene Function and Gene Therapy," Molecular Interventions, 2002, pp. 158-167, vol. 2, No. 3.
Tuschl, T., "Mammalian RNA Interference," RNAi, A Guide to Gene Silencing, Chapter 13, G.J. Hannon (ed,), 2003, pp. 265-295.
Tuschl, T., et al., "Targeted mRNA Degradation by Double-Stranded RNA in Vitro," Genes & Development, 1999, pp. 3191-3197, vol. 13.
Tuschl, T., "Expanding small RNA interference," Nature Biotechnology, May 2002, pp. 446-448, vol. 20.
Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.
Examination Report for European Patent Application No. EP 07761452, Aug. 19, 2010, 4 pages.

* cited by examiner

*Primary Examiner* — Richard Schnizer
(74) *Attorney, Agent, or Firm* — Fenwick & West LLP

(57) ABSTRACT

The invention relates to a double-stranded ribonucleic acid (dsRNA) for inhibiting the expression of a gene from the JC Virus (JC virus genome), comprising an antisense strand having a nucleotide sequence which is less that 30 nucleotides in length, generally 19-25 nucleotides in length, and which is substantially complementary to at least a part of a gene from the JC Virus. The invention also relates to a pharmaceutical composition comprising the dsRNA together with a pharmaceutically acceptable carrier; methods for treating diseases caused by JC virus expression and the expression of a gene from the JC Virus using the pharmaceutical composition; and methods for inhibiting the expression of a gene from the JC Virus in a cell.

16 Claims, No Drawings

SEQUENCE LISTING

<160> NUMBER OF SEQ ID NOS: 937

<210> SEQ ID NO 1
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 1
acuuuuaggg uuguacgggt t                                          21

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 2
cccguacaac cuaaaagut t                                           21

```
<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 3
acuuuuaggg uuguacgggt t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 4
cccguacaac ccuaaaagut t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 5
cuuuuagggu uguacgggat t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6
ucccguacaa cccuaaaagt t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 7
cuuuuagggu uguacgggat t                                              21
```

```
<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 8
ucccguacaa cccuaaaagt t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 9
cagagcacaa ggcguaccut t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 10
agguacgccu ugugcucugt t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
cagagcacaa ggcguaccut t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 12
agguacgccu ugugcucugt t                                              21
```

```
<210> SEQ ID NO 13
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 13
cagagcacaa ggcguaccut t                                               21

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 14
agguacgccu ugugcucugt t                                               21

<210> SEQ ID NO 15
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 15
cagagcacaa ggcguaccut t                                               21

<210> SEQ ID NO 16
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 16
agguacgccu ugugcucugt t                                               21

<210> SEQ ID NO 17
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 17
uaggguugua cgggacugut t                                               21
```

```
<210> SEQ ID NO 18
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 18
acagucccgu acaacccuat t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 19
uaggguugua cgggacugut t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 20
acagucccgu acaacccuat t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 21
aggguuguac gggacuguat t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 22
uacagucccg uacaaccccut t                                             21
```

```
<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 23
aggguuguac gggacuguat t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 24
uacagucccg uacaaccut t                                               21

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 25
aggguuguac gggacuguat t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 26
uacagucccg uacaaccut t                                               21

<210> SEQ ID NO 27
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 27
aggguuguac gggacuguat t                                              21
```

```
<210> SEQ ID NO 28
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 28
uacagucccg uacaacccut t                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 29
uuguacggga cuguaacact t                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 30
guguuacagu cccguacaat t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 31
uuguacggga cuguaacact t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 32
guguuacagu cccguacaat t                                              21
```

-continued

```
<210> SEQ ID NO 33
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 33
gccugauuuu gguacauggt t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 34
ccauguacca aaaucaggct t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 35
gaaguaguaa gggcguggat t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 36
uccacgcccu uacuacuuct t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 37
gaaguaguaa gggcguggat t                                              21
```

```
<210> SEQ ID NO 38
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 38
uccacgcccu uacuacuuct t                                                 21

<210> SEQ ID NO 39
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 39
gaaguaguaa gggcguggat t                                                 21

<210> SEQ ID NO 40
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 40
uccacgcccu uacuacuuct t                                                 21

<210> SEQ ID NO 41
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 41
gaaguaguaa gggcguggat t                                                 21

<210> SEQ ID NO 42
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 42
uccacgcccu uacuacuuct t                                                 21
```

-continued

```
<210> SEQ ID NO 43
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 43
auaggccuua cuccugaaat t                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 44
uuucaggagu aaggccuaut t                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 45
auaggccuua cuccugaaat t                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 46
uuucaggagu aaggccuaut t                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 47
gacagccaua ugcaguagut t                                              21
```

```
<210> SEQ ID NO 48
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 48
acuacugcau auggcuguct t                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 49
gacagccaua ugcaguagut t                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 50
acuacugcau auggcuguct t                                              21

<210> SEQ ID NO 51
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 51
gacagccaua ugcaguagut t                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 52
acuacugcau auggcuguct t                                              21
```

```
<210> SEQ ID NO 53
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 53
gacagccaua ugcaguagut t                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 54
acuacugcau auggcuguct t                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 55
aaacuacuug ggcaauagut t                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 56
acuauugccc aaguaguuut t                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 57
aaacuacuug ggcaauagut t                                              21
```

```
<210> SEQ ID NO 58
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 58
acuauugccc aaguaguuut t                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 59
aaacuacuug ggcaauagut t                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 60
acuauugccc aaguaguuut t                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 61
aaacuacuug ggcaauagut t                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 62
acuauugccc aaguaguuut t                                              21
```

```
<210> SEQ ID NO 63
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 63
ucagguucau gggugccgct t                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 64
gcggcaccca ugaaccugat t                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 65
ucagguucau gggugccgct t                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 66
gcggcaccca ugaaccugat t                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 67
guaguaaggg cguggaggct t                                              21
```

```
<210> SEQ ID NO 68
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 68
gccuccacgc ccuuacuact t                                              21

<210> SEQ ID NO 69
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 69
guaguaaggg cguggaggct t                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 70
gccuccacgc ccuuacuact t                                              21

<210> SEQ ID NO 71
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 71
uauugcaagg aauggccuat t                                              21

<210> SEQ ID NO 72
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 72
uaggccauuc cuugcaauat t                                              21
```

```
<210> SEQ ID NO 73
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 73
uauugcaagg aauggccuat t                                             21

<210> SEQ ID NO 74
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 74
uaggccauuc cuugcaauat t                                             21

<210> SEQ ID NO 75
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 75
uauugcaagg aauggccuat t                                             21

<210> SEQ ID NO 76
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 76
uaggccauuc cuugcaauat t                                             21

<210> SEQ ID NO 77
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 77
uauugcaagg aauggccuat t                                             21
```

```
<210> SEQ ID NO 78
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 78
uaggccauuc cuugcaauat t                                              21

<210> SEQ ID NO 79
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 79
aguaguaagg gcguggaggt t                                              21

<210> SEQ ID NO 80
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 80
ccuccacgcc cuuacuacut t                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 81
aguaguaagg gcguggaggt t                                              21

<210> SEQ ID NO 82
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 82
ccuccacgcc cuuacuacut t                                              21
```

```
<210> SEQ ID NO 83
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 83
aguaguaagg gcguggaggt t                                             21

<210> SEQ ID NO 84
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 84
ccuccacgcc cuuacuacut t                                             21

<210> SEQ ID NO 85
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 85
aguaguaagg gcguggaggt t                                             21

<210> SEQ ID NO 86
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 86
ccuccacgcc cuuacuacut t                                             21

<210> SEQ ID NO 87
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 87
ugcuauugcu uugauugcut t                                             21
```

```
<210> SEQ ID NO 88
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 88
agcaaucaaa gcaauagcat t                                             21

<210> SEQ ID NO 89
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 89
ugcuauugcu uugauugcut t                                             21

<210> SEQ ID NO 90
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 90
agcaaucaaa gcaauagcat t                                             21

<210> SEQ ID NO 91
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 91
ugcuauugcu uugauugcut t                                             21

<210> SEQ ID NO 92
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 92
agcaaucaaa gcaauagcat t                                             21
```

```
<210> SEQ ID NO 93
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 93
ugcuauugcu uugauugcut t                                              21

<210> SEQ ID NO 94
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 94
agcaaucaaa gcaauagcat t                                              21

<210> SEQ ID NO 95
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 95
gcuauugcuu ugauugcuut t                                              21

<210> SEQ ID NO 96
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 96
aagcaaucaa agcaauagct t                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 97
gcuauugcuu ugauugcuut t                                              21
```

```
<210> SEQ ID NO 98
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 98
aagcaaucaa agcaauagct t                                              21

<210> SEQ ID NO 99
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 99
ccuuuacuuu uagggguugut t                                             21

<210> SEQ ID NO 100
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 100
acaacccuaa aaguaaaggt t                                              21

<210> SEQ ID NO 101
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 101
uuacuuuuag gguuguacgt t                                              21

<210> SEQ ID NO 102
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 102
cguacaaccc uaaaaguaat t                                              21
```

```
<210> SEQ ID NO 103
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 103
uuacuuuuag gguuguacgt t                                              21

<210> SEQ ID NO 104
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 104
cguacaaccc uaaaaguaat t                                              21

<210> SEQ ID NO 105
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 105
gcuccucaau ggauguugct t                                              21

<210> SEQ ID NO 106
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 106
gcaacaucca uugaggagct t                                              21

<210> SEQ ID NO 107
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 107
uuauaagagg aggaguagat t                                              21
```

```
<210> SEQ ID NO 108
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 108
ucuacuccuc cucuuauaat t                                             21

<210> SEQ ID NO 109
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 109
uuauaagagg aggaguagat t                                             21

<210> SEQ ID NO 110
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 110
ucuacuccuc cucuuauaat t                                             21

<210> SEQ ID NO 111
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 111
aaguaguaag ggcguggagt t                                             21

<210> SEQ ID NO 112
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 112
cuccacgccc uuacuacuut t                                             21
```

```
<210> SEQ ID NO 113
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 113
aaguaguaag ggcguggagt t                                              21

<210> SEQ ID NO 114
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 114
cuccacgccc uuacuacuut t                                              21

<210> SEQ ID NO 115
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 115
aaguaguaag ggcguggagt t                                              21

<210> SEQ ID NO 116
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 116
cuccacgccc uuacuacuut t                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 117
aaguaguaag ggcguggagt t                                              21
```

```
<210> SEQ ID NO 118
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 118
cuccacgccc uuacuacuut t                                              21

<210> SEQ ID NO 119
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 119
uuaggguugu acgggacugt t                                              21

<210> SEQ ID NO 120
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 120
cagucccgua caacccuaat t                                              21

<210> SEQ ID NO 121
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 121
uuaggguugu acgggacugt t                                              21

<210> SEQ ID NO 122
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 122
cagucccgua caacccuaat t                                              21
```

```
<210> SEQ ID NO 123
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 123
gacaugcuuc cuuguuacat t                                              21

<210> SEQ ID NO 124
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 124
uguaacaagg aagcauguct t                                              21

<210> SEQ ID NO 125
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 125
gacaugcuuc cuuguuacat t                                              21

<210> SEQ ID NO 126
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 126
uguaacaagg aagcauguct t                                              21

<210> SEQ ID NO 127
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 127
gacaugcuuc cuuguuacat t                                              21
```

```
<210> SEQ ID NO 128
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 128
uguaacaagg aagcauguct t                                             21

<210> SEQ ID NO 129
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 129
gacaugcuuc cuuguuacat t                                             21

<210> SEQ ID NO 130
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 130
uguaacaagg aagcauguct t                                             21

<210> SEQ ID NO 131
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O' methyl nucleotide
<220> FEATURE:
<221> NAME/KEY: modified_base
<222> LOCATION: (3)..(4)
<223> OTHER INFORMATION: 2'-O' methyl nucleotide
<220> FEATURE:
<221> NAME/KEY: modified_base
<222> LOCATION: (8)..(8)
<223> OTHER INFORMATION: 2'-O' methyl nucleotide
<220> FEATURE:
<221> NAME/KEY: modified_base
<222> LOCATION: (10)..(11)
<223> OTHER INFORMATION: 2'-O' methyl nucleotide
<220> FEATURE:
<221> NAME/KEY: modified_base
<222> LOCATION: (15)..(19)
<223> OTHER INFORMATION: 2'-O' methyl nucleotide
<220> FEATURE:
<221> NAME/KEY: misc_feature
```

```
<222> LOCATION: (20)..(21)
<223> OTHER INFORMATION: Phosphorothioate linkage

<400> SEQUENCE: 131
uguugaaugu uggguuccut t                                          21

<210> SEQ ID NO 132
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O' methyl nucleotide
<220> FEATURE:
<221> NAME/KEY: modified_base
<222> LOCATION: (8)..(8)
<223> OTHER INFORMATION: 2'-O' methyl nucleotide
<220> FEATURE:
<221> NAME/KEY: modified_base
<222> LOCATION: (11)..(11)
<223> OTHER INFORMATION: 2'-O' methyl nucleotide
<220> FEATURE:
<221> NAME/KEY: modified_base
<222> LOCATION: (15)..(15)
<223> OTHER INFORMATION: 2'-O' methyl nucleotide
<220> FEATURE:
<221> NAME/KEY: modified_base
<222> LOCATION: (18)..(18)
<223> OTHER INFORMATION: 2'-O' methyl nucleotide
<220> FEATURE:
<221> NAME/KEY: misc_feature
<222> LOCATION: (20)..(21)
<223> OTHER INFORMATION: Phosphorothioate linkage

<400> SEQUENCE: 132
aggaacccaa cauucaacat t                                          21

<210> SEQ ID NO 133
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 133
uguugaaugu uggguuccut t                                          21

<210> SEQ ID NO 134
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 134
aggaacccaa cauucaacat t                                          21
```

```
<210> SEQ ID NO 135
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 135
uguugaaugu uggguuccut t                                              21

<210> SEQ ID NO 136
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 136
aggaacccaa cauucaacat t                                              21

<210> SEQ ID NO 137
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 137
uguugaaugu uggguuccut t                                              21

<210> SEQ ID NO 138
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 138
aggaacccaa cauucaacat t                                              21

<210> SEQ ID NO 139
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 139
acuuaaccca agaagcucut t                                              21
```

```
<210> SEQ ID NO 140
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 140
agagcuucuu ggguuaagut t                                              21

<210> SEQ ID NO 141
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 141
acuuaaccca agaagcucut t                                              21

<210> SEQ ID NO 142
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 142
agagcuucuu ggguuaagut t                                              21

<210> SEQ ID NO 143
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 143
ucagccugau uuugguacat t                                              21

<210> SEQ ID NO 144
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 144
uguaccaaaa ucaggcugat t                                              21
```

```
<210> SEQ ID NO 145
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 145
ucagccugau uuugguacat t                                             21

<210> SEQ ID NO 146
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 146
uguaccaaaa ucaggcugat t                                             21

<210> SEQ ID NO 147
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 147
uuuuaggguu guacgggact t                                             21

<210> SEQ ID NO 148
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 148
gucccguaca acccuaaaat t                                             21

<210> SEQ ID NO 149
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 149
uuuuaggguu guacgggact t                                             21
```

```
<210> SEQ ID NO 150
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 150
gucccguaca acccuaaaat t                                              21

<210> SEQ ID NO 151
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 151
uuuaggguug uacgggacut t                                              21

<210> SEQ ID NO 152
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 152
agucccguac aacccuaaat t                                              21

<210> SEQ ID NO 153
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 153
uuuaggguug uacgggacut t                                              21

<210> SEQ ID NO 154
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 154
agucccguac aacccuaaat t                                              21
```

```
<210> SEQ ID NO 155
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 155
ucccuugcua cguagaggt t                                              21

<210> SEQ ID NO 156
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 156
ccucuacagu agcaagggat t                                             21

<210> SEQ ID NO 157
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 157
ucccuugcua cguagaggt t                                              21

<210> SEQ ID NO 158
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 158
ccucuacagu agcaagggat t                                             21

<210> SEQ ID NO 159
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 159
cccuugcuac uguagagggt t                                             21
```

```
<210> SEQ ID NO 160
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 160
cccucuacag uagcaagggt t                                              21

<210> SEQ ID NO 161
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 161
cccuugcuac uguagagggt t                                              21

<210> SEQ ID NO 162
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 162
cccucuacag uagcaagggt t                                              21

<210> SEQ ID NO 163
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 163
ugcuccucaa uggauguugt t                                              21

<210> SEQ ID NO 164
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 164
caacauccau ugaggagcat t                                              21
```

```
<210> SEQ ID NO 165
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 165
ugcuccucaa uggauguugt t                                              21

<210> SEQ ID NO 166
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 166
caacauccau ugaggagcat t                                              21

<210> SEQ ID NO 167
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 167
ugcuccucaa uggauguugt t                                              21

<210> SEQ ID NO 168
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 168
caacauccau ugaggagcat t                                              21

<210> SEQ ID NO 169
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 169
ugcuccucaa uggauguugt t                                              21
```

<210> SEQ ID NO 170
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 170
caacauccau ugaggagcat t                                              21

<210> SEQ ID NO 171
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 171
gaucugcucc ucaauggaut t                                              21

<210> SEQ ID NO 172
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 172
auccauugag gagcagauct t                                              21

<210> SEQ ID NO 173
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 173
gaucugcucc ucaauggaut t                                              21

<210> SEQ ID NO 174
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 174
auccauugag gagcagauct t                                              21

```
<210> SEQ ID NO 175
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 175
gaucugcucc ucaauggaut t                                             21

<210> SEQ ID NO 176
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 176
auccauugag gagcagauct t                                             21

<210> SEQ ID NO 177
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 177
gaucugcucc ucaauggaut t                                             21

<210> SEQ ID NO 178
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 178
auccauugag gagcagauct t                                             21

<210> SEQ ID NO 179
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 179
aucugcuccu caauggaugt t                                             21
```

```
<210> SEQ ID NO 180
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 180
cauccauuga ggagcagaut t                                            21

<210> SEQ ID NO 181
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 181
aucugcuccu caauggaugt t                                            21

<210> SEQ ID NO 182
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 182
cauccauuga ggagcagaut t                                            21

<210> SEQ ID NO 183
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 183
ucugcuccuc aauggaugut t                                            21

<210> SEQ ID NO 184
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 184
acauccauug aggagcagat t                                            21
```

```
<210> SEQ ID NO 185
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 185
cugcuccuca auggauguut t                                                    21

<210> SEQ ID NO 186
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 186
aacauccauu gaggagcagt t                                                    21

<210> SEQ ID NO 187
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 187
cugcuccuca auggauguut t                                                    21

<210> SEQ ID NO 188
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 188
aacauccauu gaggagcagt t                                                    21

<210> SEQ ID NO 189
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 189
guuguacggg acuguaacat t                                                    21
```

```
<210> SEQ ID NO 190
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 190
uguuacaguc ccguacaact t                                              21

<210> SEQ ID NO 191
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 191
guuguacggg acuguaacat t                                              21

<210> SEQ ID NO 192
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 192
uguuacaguc ccguacaact t                                              21

<210> SEQ ID NO 193
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 193
uguacgggac uguaacacct t                                              21

<210> SEQ ID NO 194
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 194
gguguuacag ucccguacat t                                              21
```

```
<210> SEQ ID NO 195
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 195
uguacgggac uguaacacct t                                              21

<210> SEQ ID NO 196
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 196
gguguuacag ucccguacat t                                              21

<210> SEQ ID NO 197
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 197
uguacgggac uguaacacct t                                              21

<210> SEQ ID NO 198
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 198
gguguuacag ucccguacat t                                              21

<210> SEQ ID NO 199
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 199
uguacgggac uguaacacct t                                              21
```

```
<210> SEQ ID NO 200
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 200
gguguuacag ucccguacat t                                              21

<210> SEQ ID NO 201
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 201
guacgggacu guaacaccut t                                              21

<210> SEQ ID NO 202
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 202
agguguuaca gucccguact t                                              21

<210> SEQ ID NO 203
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 203
guacgggacu guaacaccut t                                              21

<210> SEQ ID NO 204
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 204
agguguuaca gucccguact t                                              21
```

```
<210> SEQ ID NO 205
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 205
cagccugauu uugguacaut t                                              21

<210> SEQ ID NO 206
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 206
auguaccaaa aucaggcugt t                                              21

<210> SEQ ID NO 207
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 207
cagccugauu uugguacaut t                                              21

<210> SEQ ID NO 208
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 208
auguaccaaa aucaggcugt t                                              21

<210> SEQ ID NO 209
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 209
cagccugauu uugguacaut t                                              21
```

```
<210> SEQ ID NO 210
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 210
auguaccaaa aucaggcugt t                                              21

<210> SEQ ID NO 211
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 211
cagccugauu uugguacaut t                                              21

<210> SEQ ID NO 212
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 212
auguaccaaa aucaggcugt t                                              21

<210> SEQ ID NO 213
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 213
gaauagggag gaauccaugt t                                              21

<210> SEQ ID NO 214
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 214
cauggauucc ucccuauuct t                                              21
```

```
<210> SEQ ID NO 215
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 215
gaauagggag gaauccaugt t                                              21

<210> SEQ ID NO 216
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 216
cauggauucc ucccuauuct t                                              21

<210> SEQ ID NO 217
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 217
gaauagggag gaauccaugt t                                              21

<210> SEQ ID NO 218
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 218
cauggauucc ucccuauuct t                                              21

<210> SEQ ID NO 219
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 219
gaauagggag gaauccaugt t                                              21
```

```
<210> SEQ ID NO 220
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 220
cauggauucc ucccuauuct t                                              21

<210> SEQ ID NO 221
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 221
aagugcugaa uagggaggat t                                              21

<210> SEQ ID NO 222
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 222
uccucccuau ucagcacuut t                                              21

<210> SEQ ID NO 223
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 223
aagugcugaa uagggaggat t                                              21

<210> SEQ ID NO 224
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 224
uccucccuau ucagcacuut t                                              21
```

```
<210> SEQ ID NO 225
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 225
aagugcugaa uagggaggat t                                              21

<210> SEQ ID NO 226
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 226
uccucccuau ucagcacuut t                                              21

<210> SEQ ID NO 227
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 227
aagugcugaa uagggaggat t                                              21

<210> SEQ ID NO 228
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 228
uccucccuau ucagcacuut t                                              21

<210> SEQ ID NO 229
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 229
aggcugcugc uacuauagat t                                              21
```

```
<210> SEQ ID NO 230
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 230
ucuauaguag cagcagccut t                                              21

<210> SEQ ID NO 231
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 231
aggcugcugc uacuauagat t                                              21

<210> SEQ ID NO 232
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 232
ucuauaguag cagcagccut t                                              21

<210> SEQ ID NO 233
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 233
aggcugcugc uacuauagat t                                              21

<210> SEQ ID NO 234
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 234
ucuauaguag cagcagccut t                                              21
```

```
<210> SEQ ID NO 235
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 235
aggcugcugc uacuauagat t                                            21

<210> SEQ ID NO 236
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 236
ucuauaguag cagcagccut t                                            21

<210> SEQ ID NO 237
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 237
agacagccau augcaguagt t                                            21

<210> SEQ ID NO 238
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 238
cuacugcaua uggcugucut t                                            21

<210> SEQ ID NO 239
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 239
agacagccau augcaguagt t                                            21
```

```
<210> SEQ ID NO 240
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 240
cuacugcaua uggcugucut t                                               21

<210> SEQ ID NO 241
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 241
uucagguuca ugggugccgt t                                               21

<210> SEQ ID NO 242
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 242
cggcacccau gaaccugaat t                                               21

<210> SEQ ID NO 243
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 243
uucagguuca ugggugccgt t                                               21

<210> SEQ ID NO 244
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 244
cggcacccau gaaccugaat t                                               21
```

```
<210> SEQ ID NO 245
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 245
uagacagcca uaugcaguat t                                              21

<210> SEQ ID NO 246
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 246
uacugcauau ggcugucuat t                                              21

<210> SEQ ID NO 247
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 247
uagacagcca uaugcaguat t                                              21

<210> SEQ ID NO 248
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 248
uacugcauau ggcugucuat t                                              21

<210> SEQ ID NO 249
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 249
uagacagcca uaugcaguat t                                              21
```

```
<210> SEQ ID NO 250
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 250
uacugcauau ggcugucuat t                                              21

<210> SEQ ID NO 251
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 251
uagacagcca uaugcaguat t                                              21

<210> SEQ ID NO 252
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 252
uacugcauau ggcugucuat t                                              21

<210> SEQ ID NO 253
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 253
ggagcaugac uuuaacccat t                                              21

<210> SEQ ID NO 254
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 254
uggguuaaag ucaugcucct t                                              21
```

```
<210> SEQ ID NO 255
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 255
ggagcaugac uuuaacccat t                                          21

<210> SEQ ID NO 256
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 256
uggguuaaag ucaugcucct t                                          21

<210> SEQ ID NO 257
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 257
ggagcaugac uuuaacccat t                                          21

<210> SEQ ID NO 258
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 258
uggguuaaag ucaugcucct t                                          21

<210> SEQ ID NO 259
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 259
ggagcaugac uuuaacccat t                                          21
```

```
<210> SEQ ID NO 260
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 260
uggguuaaag ucaugcucct t                                            21

<210> SEQ ID NO 261
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 261
guugccuuua cuuuuagggt t                                            21

<210> SEQ ID NO 262
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 262
cccuaaaagu aaaggcaact t                                            21

<210> SEQ ID NO 263
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 263
guugccuuua cuuuuagggt t                                            21

<210> SEQ ID NO 264
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 264
cccuaaaagu aaaggcaact t                                            21
```

```
<210> SEQ ID NO 265
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 265
ugugacuuaa cccaagaagt t                                                 21

<210> SEQ ID NO 266
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 266
cuucuugggu uaagucacat t                                                 21

<210> SEQ ID NO 267
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 267
ugugacuuaa cccaagaagt t                                                 21

<210> SEQ ID NO 268
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 268
cuucuugggu uaagucacat t                                                 21

<210> SEQ ID NO 269
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 269
ugugacuuaa cccaagaagt t                                                 21
```

```
<210> SEQ ID NO 270
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 270
cuucuugggu uaagucacat t                                              21

<210> SEQ ID NO 271
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 271
ugugacuuaa cccaagaagt t                                              21

<210> SEQ ID NO 272
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 272
cuucuugggu uaagucacat t                                              21

<210> SEQ ID NO 273
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 273
uauugcuuug auugcuucat t                                              21

<210> SEQ ID NO 274
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 274
ugaagcaauc aaagcaauat t                                              21
```

```
<210> SEQ ID NO 275
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 275
uauugcuuug auugcuucat t                                              21

<210> SEQ ID NO 276
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 276
ugaagcaauc aaagcaauat t                                              21

<210> SEQ ID NO 277
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 277
uauugcuuug auugcuucat t                                              21

<210> SEQ ID NO 278
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 278
ugaagcaauc aaagcaauat t                                              21

<210> SEQ ID NO 279
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 279
uauugcuuug auugcuucat t                                              21
```

```
<210> SEQ ID NO 280
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 280
ugaagcaauc aaagcaauat t                                              21

<210> SEQ ID NO 281
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 281
auauccuguu gaauguuggt t                                              21

<210> SEQ ID NO 282
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 282
ccaacauuca acaggauaut t                                              21

<210> SEQ ID NO 283
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 283
uuuauugcaa ggaauggcct t                                              21

<210> SEQ ID NO 284
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 284
ggccauuccu ugcaauaaat t                                              21
```

```
<210> SEQ ID NO 285
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 285
uuuauugcaa ggaauggcct t                                          21

<210> SEQ ID NO 286
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 286
ggccauuccu ugcaauaaat t                                          21

<210> SEQ ID NO 287
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 287
uggaagaaac uacuugggct t                                          21

<210> SEQ ID NO 288
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 288
gcccaaguag uuucuuccat t                                          21

<210> SEQ ID NO 289
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 289
uggaagaaac uacuugggct t                                          21
```

```
<210> SEQ ID NO 290
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 290
gcccaaguag uuucuuccat t                                             21

<210> SEQ ID NO 291
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 291
uggaagaaac uacuugggct t                                             21

<210> SEQ ID NO 292
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 292
gcccaaguag uuucuuccat t                                             21

<210> SEQ ID NO 293
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 293
uggaagaaac uacuugggct t                                             21

<210> SEQ ID NO 294
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 294
gcccaaguag uuucuuccat t                                             21
```

```
<210> SEQ ID NO 295
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 295
aagacccuaa agacuuucct t                                            21

<210> SEQ ID NO 296
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 296
ggaaagucuu uagggucuut t                                            21

<210> SEQ ID NO 297
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 297
aagacccuaa agacuuucct t                                            21

<210> SEQ ID NO 298
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 298
ggaaagucuu uagggucuut t                                            21

<210> SEQ ID NO 299
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 299
aagacccuaa agacuuucct t                                            21
```

```
<210> SEQ ID NO 300
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 300
ggaaagucuu uagggucuut t                                              21

<210> SEQ ID NO 301
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 301
aagacccuaa agacuuucct t                                              21

<210> SEQ ID NO 302
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 302
ggaaagucuu uagggucuut t                                              21

<210> SEQ ID NO 303
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 303
uggauguugc cuuuacuuut t                                              21

<210> SEQ ID NO 304
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 304
aaaguaaagg caacauccat t                                              21
```

```
<210> SEQ ID NO 305
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 305
uggauguugc cuuuacuuut t                                              21

<210> SEQ ID NO 306
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 306
aaaguaaagg caacauccat t                                              21

<210> SEQ ID NO 307
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 307
uggauguugc cuuuacuuut t                                              21

<210> SEQ ID NO 308
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 308
aaaguaaagg caacauccat t                                              21

<210> SEQ ID NO 309
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 309
uggauguugc cuuuacuuut t                                              21
```

```
<210> SEQ ID NO 310
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 310
aaaguaaagg caacauccat t                                          21

<210> SEQ ID NO 311
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 311
uuugauugcu ucagacaaut t                                          21

<210> SEQ ID NO 312
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 312
auugucugaa gcaaucaaat t                                          21

<210> SEQ ID NO 313
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 313
uuugauugcu ucagacaaut t                                          21

<210> SEQ ID NO 314
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 314
auugucugaa gcaaucaaat t                                          21
```

```
<210> SEQ ID NO 315
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 315
aauagggagg aauccauggt t                                             21

<210> SEQ ID NO 316
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 316
ccauggauuc cucccuauut t                                             21

<210> SEQ ID NO 317
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 317
aauagggagg aauccauggt t                                             21

<210> SEQ ID NO 318
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 318
ccauggauuc cucccuauut t                                             21

<210> SEQ ID NO 319
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 319
ggacaaagug cugaauaggt t                                             21
```

```
<210> SEQ ID NO 320
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 320
ccuauucagc acuugucct t                                                    21

<210> SEQ ID NO 321
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 321
ggacaaagug cugaauaggt t                                                   21

<210> SEQ ID NO 322
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 322
ccuauucagc acuugucct t                                                    21

<210> SEQ ID NO 323
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 323
ggacaaagug cugaauaggt t                                                   21

<210> SEQ ID NO 324
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 324
ccuauucagc acuugucct t                                                    21
```

```
<210> SEQ ID NO 325
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 325
ggacaaagug cugaauaggt t                                              21

<210> SEQ ID NO 326
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 326
ccuauucagc acuuugucct t                                              21

<210> SEQ ID NO 327
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 327
uggacaaagu gcugaauagt t                                              21

<210> SEQ ID NO 328
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 328
cuauucagca cuuuguccat t                                              21

<210> SEQ ID NO 329
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 329
uggacaaagu gcugaauagt t                                              21
```

```
<210> SEQ ID NO 330
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 330
cuauucagca cuuuguccat t                                              21

<210> SEQ ID NO 331
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 331
aaauugcauc ccuugcuact t                                              21

<210> SEQ ID NO 332
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 332
guagcaaggg augcaauuut t                                              21

<210> SEQ ID NO 333
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 333
aaauugcauc ccuugcuact t                                              21

<210> SEQ ID NO 334
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 334
guagcaaggg augcaauuut t                                              21
```

```
<210> SEQ ID NO 335
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 335
gcaucccuug cuacuguagt t                                            21

<210> SEQ ID NO 336
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 336
cuacaguagc aagggaugct t                                            21

<210> SEQ ID NO 337
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 337
aaaaaaaggu agaagaccct t                                            21

<210> SEQ ID NO 338
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 338
gggucuucua ccuuuuuuut t                                            21

<210> SEQ ID NO 339
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 339
aaaaaaaggu agaagaccct t                                            21
```

```
<210> SEQ ID NO 340
<211> LENTGH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 340
gggucuucua ccuuuuuuut t                                               21

<210> SEQ ID NO 341
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 341
aaaaaaaggu agaagaccct t                                               21

<210> SEQ ID NO 342
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 342
gggucuucua ccuuuuuuut t                                               21

<210> SEQ ID NO 343
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 343
aaaaaaaggu agaagaccct t                                               21

<210> SEQ ID NO 344
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 344
gggucuucua ccuuuuuuut t                                               21
```

```
<210> SEQ ID NO 345
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 345
acagagcaca aggcguacct t                                             21

<210> SEQ ID NO 346
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 346
gguacgccuu gugcucugut t                                             21

<210> SEQ ID NO 347
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 347
acagagcaca aggcguacct t                                             21

<210> SEQ ID NO 348
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 348
gguacgccuu gugcucugut t                                             21

<210> SEQ ID NO 349
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 349 ugauuuggu acauggaaut t                                              21
```

```
<210> SEQ ID NO 350
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 350
auuccaugua ccaaaaucat t                                             21

<210> SEQ ID NO 351
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 351
ugauuuuggu acauggaaut t                                             21

<210> SEQ ID NO 352
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 352
auuccaugua ccaaaaucat t                                             21

<210> SEQ ID NO 353
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 353
ugauuuuggu acauggaaut t                                             21

<210> SEQ ID NO 354
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 354
auuccaugua ccaaaaucat t                                             21
```

```
<210> SEQ ID NO 355
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 355
ugauuuuggu acauggaaut t                                              21

<210> SEQ ID NO 356
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 356
auuccaugua ccaaaaucat t                                              21

<210> SEQ ID NO 357
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 357
ggguuguacg ggacuguaat t                                              21

<210> SEQ ID NO 358
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 358
uuacagaccc guacaaccct t                                              21

<210> SEQ ID NO 359
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 359
ggguuguacg ggacuguaat t                                              21
```

```
<210> SEQ ID NO 360
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 360
uuacaguccc guacaaccct t                                              21

<210> SEQ ID NO 361
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 361
gguuguacgg gacuguaact t                                              21

<210> SEQ ID NO 362
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 362
guuacagucc cguacaacct t                                              21

<210> SEQ ID NO 363
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 363
gguuguacgg gacuguaact t                                              21

<210> SEQ ID NO 364
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 364
guuacagucc cguacaacct t                                              21
```

```
<210> SEQ ID NO 365
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 365
gguuguacgg gacuguaact t                                              21

<210> SEQ ID NO 366
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 366
guuacagucc cguacaacct t                                              21

<210> SEQ ID NO 367
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 367
gguuguacgg gacuguaact t                                              21

<210> SEQ ID NO 368
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 368
guuacagucc cguacaacct t                                              21

<210> SEQ ID NO 369
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 369
acgggacugu aacaccugct t                                              21
```

```
<210> SEQ ID NO 370
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 370
gcagguguua cagucccgut t                                              21

<210> SEQ ID NO 371
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 371
gggacuguaa caccugcuct t                                              21

<210> SEQ ID NO 372
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 372
gagcaggugu uacaguccct t                                              21

<210> SEQ ID NO 373
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 373
gggacuguaa caccugcuct t                                              21

<210> SEQ ID NO 374
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 374
gagcaggugu uacaguccct t                                              21
```

```
<210> SEQ ID NO 375
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 375
gggacuguaa caccugcuct t                                              21

<210> SEQ ID NO 376
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 376
gagcaggugu uacaguccct t                                              21

<210> SEQ ID NO 377
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 377
gggacuguaa caccugcuct t                                              21

<210> SEQ ID NO 378
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 378
gagcaggugu uacaguccct t                                              21

<210> SEQ ID NO 379
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 379
acuccagaaa ugggugacct t                                              21
```

```
<210> SEQ ID NO 380
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 380
ggucacccau uucuggagut t                                           21

<210> SEQ ID NO 381
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 381
acuccagaaa ugggugacct t                                           21

<210> SEQ ID NO 382
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 382
ggucacccau uucuggagut t                                           21

<210> SEQ ID NO 383
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 383
ccugauuuug guacauggat t                                           21

<210> SEQ ID NO 384
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 384
uccauguacc aaaaucaggt t                                           21
```

```
<210> SEQ ID NO 385
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 385
ccugauuuug guacauggat t                                              21

<210> SEQ ID NO 386
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 386
uccauguacc aaaaucaggt t                                              21

<210> SEQ ID NO 387
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 387
caaagugcug aauagggagt t                                              21

<210> SEQ ID NO 388
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 388
cucccuauuc agcacuuugt t                                              21

<210> SEQ ID NO 389
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 389
caaagugcug aauagggagt t                                              21
```

```
<210> SEQ ID NO 390
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 390
cucccuauuc agcacuuugt t                                             21

<210> SEQ ID NO 391
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 391
caaagugcug aauagggagt t                                             21

<210> SEQ ID NO 392
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 392
cucccuauuc agcacuuugt t                                             21

<210> SEQ ID NO 393
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 393
caaagugcug aauagggagt t                                             21

<210> SEQ ID NO 394
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 394
cucccuauuc agcacuuugt t                                             21
```

```
<210> SEQ ID NO 395
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 395
ccagggaaau ucccuuguut t                                              21

<210> SEQ ID NO 396
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 396
aacaagggaa uucccuggt t                                               21

<210> SEQ ID NO 397
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 397
ccagggaaau ucccuuguut t                                              21

<210> SEQ ID NO 398
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 398
aacaagggaa uucccuggt t                                               21

<210> SEQ ID NO 399
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 399
aggccaggga aauucccuut t                                              21
```

```
<210> SEQ ID NO 400
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 400
aagggaauuu cccuggccut t                                          21

<210> SEQ ID NO 401
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 401
aggccaggga aauucccuut t                                          21

<210> SEQ ID NO 402
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 402
aagggaauuu cccuggccut t                                          21

<210> SEQ ID NO 403
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 403
aggccaggga aauucccuut t                                          21

<210> SEQ ID NO 404
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 404
aagggaauuu cccuggccut t                                          21
```

```
<210> SEQ ID NO 405
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 405
aggccaggga aauucccuut t                                          21

<210> SEQ ID NO 406
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 406
aagggaauuu cccuggccut t                                          21

<210> SEQ ID NO 407
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 407
uaguugcuac uguuucugat t                                          21

<210> SEQ ID NO 408
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 408
ucagaaacag uagcaacuat t                                          21

<210> SEQ ID NO 409
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 409
uaguugcuac uguuucugat t                                          21
```

<210> SEQ ID NO 410
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 410
ucagaaacag uagcaacuat t                                              21

<210> SEQ ID NO 411
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 411
cugcugcuac uauagaagut t                                              21

<210> SEQ ID NO 412
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 412
acuucuauag uagcagcagt t                                              21

<210> SEQ ID NO 413
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 413
cugcugcuac uauagaagut t                                              21

<210> SEQ ID NO 414
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 414
acuucuauag uagcagcagt t                                              21

```
<210> SEQ ID NO 415
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 415
ugcugcuacu auagaaguut t                                              21

<210> SEQ ID NO 416
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 416
aacuucuaua guagcagcat t                                              21

<210> SEQ ID NO 417
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 417
ugcugcuacu auagaaguut t                                              21

<210> SEQ ID NO 418
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 418
aacuucuaua guagcagcat t                                              21

<210> SEQ ID NO 419
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 419
ugcugcuacu auagaaguut t                                              21
```

```
<210> SEQ ID NO 420
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 420
aacuucuaua guagcagcat t                                             21

<210> SEQ ID NO 421
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 421
ugcugcuacu auagaaguut t                                             21

<210> SEQ ID NO 422
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 422
aacuucuaua guagcagcat t                                             21

<210> SEQ ID NO 423
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 423
gcugcuacua uagaaguugt t                                             21

<210> SEQ ID NO 424
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 424
caacuucuau aguagcagct t                                             21
```

```
<210> SEQ ID NO 425
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 425
gcugcuacua uagaaguugt t                                            21

<210> SEQ ID NO 426
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 426
caacuucuau aguagcagct t                                            21

<210> SEQ ID NO 427
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 427
cugcuacuau agaaguugat t                                            21

<210> SEQ ID NO 428
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 428
ucaacuucua uaguagcagt t                                            21

<210> SEQ ID NO 429
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 429
ugcuacuaua gaaguugaat t                                            21
```

```
<210> SEQ ID NO 430
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 430
uucaacuucu auaguagcat t                                           21

<210> SEQ ID NO 431
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 431
ugcuacuaua gaaguugaat t                                           21

<210> SEQ ID NO 432
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 432
uucaacuucu auaguagcat t                                           21

<210> SEQ ID NO 433
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 433
ugcuacuaua gaaguugaat t                                           21

<210> SEQ ID NO 434
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 434
uucaacuucu auaguagcat t                                           21
```

```
<210> SEQ ID NO 435
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 435
ugcuacuaua gaaguugaat t                                             21

<210> SEQ ID NO 436
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 436
uucaacuucu auaguagcat t                                             21

<210> SEQ ID NO 437
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 437
cagaagacua cuaugauaut t                                             21

<210> SEQ ID NO 438
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 438
auaucauagu agucuucgt t                                              21

<210> SEQ ID NO 439
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 439
cagaagacua cuaugauaut t                                             21
```

```
<210> SEQ ID NO 440
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 440
auaucauagu agucuucugt t                                              21

<210> SEQ ID NO 441
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 441
aaauuuuaua uaagaaacut t                                              21

<210> SEQ ID NO 442
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 442
aguuucuuau auaaaauuut t                                              21

<210> SEQ ID NO 443
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 443
aaauuuuaua uaagaaacut t                                              21

<210> SEQ ID NO 444
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 444
aguuucuuau auaaaauuut t                                              21
```

```
<210> SEQ ID NO 445
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 445
aaauuuuaua uagaaacut t                                              21

<210> SEQ ID NO 446
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 446 aguucuuau auaaaauuut t                                              21

<210> SEQ ID NO 447
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 447
aaauuuuaua uagaaacut t                                              21

<210> SEQ ID NO 448
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 448 aguucuuau auaaaauuut t                                              21

<210> SEQ ID NO 449
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 449
auggaauagu ucagagguut t                                             21
```

```
<210> SEQ ID NO 450
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 450
aaccucugaa cuauuccaut t                                              21

<210> SEQ ID NO 451
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 451
auggaauagu ucagagguut t                                              21

<210> SEQ ID NO 452
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 452
aaccucugaa cuauuccaut t                                              21

<210> SEQ ID NO 453
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 453
cauggaauag uucagaggut t                                              21

<210> SEQ ID NO 454
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 454
accucugaac uauuccaugt t                                              21
```

```
<210> SEQ ID NO 455
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 455
cauggaauag uucagaggut t                                          21

<210> SEQ ID NO 456
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 456
accucugaac uauuccaugt t                                          21

<210> SEQ ID NO 457
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 457
cauggaauag uucagaggut t                                          21

<210> SEQ ID NO 458
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 458
accucugaac uauuccaugt t                                          21

<210> SEQ ID NO 459
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 459
cauggaauag uucagaggut t                                          21
```

```
<210> SEQ ID NO 460
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 460
accucugaac uauuccaugt t                                           21

<210> SEQ ID NO 461
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 461
acauggaaua guucagaggt t                                           21

<210> SEQ ID NO 462
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 462
ccucugaacu auuccaugut t                                           21

<210> SEQ ID NO 463
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 463
acauggaaua guucagaggt t                                           21

<210> SEQ ID NO 464
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 464
ccucugaacu auuccaugut t                                           21
```

```
<210> SEQ ID NO 465
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 465
gguacaugga auaguucagt t                                              21

<210> SEQ ID NO 466
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 466
cugaacuauu ccauguacct t                                              21

<210> SEQ ID NO 467
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 467
gguacaugga auaguucagt t                                              21

<210> SEQ ID NO 468
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 468
cugaacuauu ccauguacct t                                              21

<210> SEQ ID NO 469
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 469
gguacaugga auaguucagt t                                              21
```

```
<210> SEQ ID NO 470
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 470
cugaacuauu ccauguacct t                                              21

<210> SEQ ID NO 471
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 471
gguacaugga auaguucagt t                                              21

<210> SEQ ID NO 472
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 472
cugaacuauu ccauguacct t                                              21

<210> SEQ ID NO 473
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 473
ugguacaugg aauaguucat t                                              21

<210> SEQ ID NO 474
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 474
ugaacuauuc cauguaccat t                                              21
```

```
<210> SEQ ID NO 475
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 475
ugguacaugg aauaguucat t                                                   21

<210> SEQ ID NO 476
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 476
ugaacuauuc cauguaccat t                                                   21

<210> SEQ ID NO 477
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 477
ugguacaugg aauaguucat t                                                   21

<210> SEQ ID NO 478
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 478
ugaacuauuc cauguaccat t                                                   21

<210> SEQ ID NO 479
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 479
ugguacaugg aauaguucat t                                                   21
```

-continued

```
<210> SEQ ID NO 480
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 480
ugaacuauuc cauguaccat t                                              21

<210> SEQ ID NO 481
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 481
cuuacuccug aaacauaugt t                                              21

<210> SEQ ID NO 482
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 482
cauauguuuc aggaguaagt t                                              21

<210> SEQ ID NO 483
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 483
cuuacuccug aaacauaugt t                                              21

<210> SEQ ID NO 484
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 484
cauauguuuc aggaguaagt t                                              21
```

```
<210> SEQ ID NO 485
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 485
auccagaaga cuacuaugat t                                               21

<210> SEQ ID NO 486
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 486
ucauaguagu cuucuggaut t                                               21

<210> SEQ ID NO 487
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 487
uuuuggaaga aacuacuugt t                                               21

<210> SEQ ID NO 488
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 488
caaguaguuu cuuccaaaat t                                               21

<210> SEQ ID NO 489
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 489
uuuuggaaga aacuacuugt t                                               21
```

```
<210> SEQ ID NO 490
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 490
caaguaguuu cuuccaaaat t                                              21

<210> SEQ ID NO 491
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 491
uuggaagaaa cuacuugggt t                                              21

<210> SEQ ID NO 492
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 492
cccaaguagu uucuuccaat t                                              21

<210> SEQ ID NO 493
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 493
uuggaagaaa cuacuugggt t                                              21

<210> SEQ ID NO 494
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 494
cccaaguagu uucuuccaat t                                              21
```

-continued

```
<210> SEQ ID NO 495
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 495
augaagaccu guuuugccat t                                             21

<210> SEQ ID NO 496
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 496
uggcaaaaca ggucuucaut t                                             21

<210> SEQ ID NO 497
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 497
augaagaccu guuuugccat t                                             21

<210> SEQ ID NO 498
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 498
uggcaaaaca ggucuucaut t                                             21

<210> SEQ ID NO 499
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 499
gaugaagacc uguuuugcct t                                             21
```

```
<210> SEQ ID NO 500
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 500
ggcaaaacag gucuucauct t                                              21

<210> SEQ ID NO 501
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 501
gaugaagacc uguuuugcct t                                              21

<210> SEQ ID NO 502
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 502
ggcaaaacag gucuucauct t                                              21

<210> SEQ ID NO 503
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 503
gaugaagacc uguuuugcct t                                              21

<210> SEQ ID NO 504
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 504
ggcaaaacag gucuucauct t                                              21
```

```
<210> SEQ ID NO 505
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 505
gaugaagacc uguuugcct t                                              21

<210> SEQ ID NO 506
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 506
ggcaaaacag gucuucauct t                                             21

<210> SEQ ID NO 507
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 507
gggaugaaga ccuguuugt t                                              21

<210> SEQ ID NO 508
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 508
caaaacaggu cuucauccct t                                             21

<210> SEQ ID NO 509
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 509
gggaugaaga ccuguuugt t                                              21
```

```
<210> SEQ ID NO 510
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 510
caaaacaggu cuucauccct t                                           21

<210> SEQ ID NO 511
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 511
gggaugaaga ccuguuuugt t                                           21

<210> SEQ ID NO 512
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 512
caaaacaggu cuucauccct t                                           21

<210> SEQ ID NO 513
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 513
gggaugaaga ccuguuuugt t                                           21

<210> SEQ ID NO 514
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 514
caaaacaggu cuucauccct t                                           21
```

```
<210> SEQ ID NO 515
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 515
cuuauaagag gaggaguagt t                                              21

<210> SEQ ID NO 516
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 516
cuacuccucc ucuuauaagt t                                              21

<210> SEQ ID NO 517
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 517
caugcuuccu uguuacagut t                                              21

<210> SEQ ID NO 518
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 518
acuguaacaa ggaagcaugt t                                              21

<210> SEQ ID NO 519
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 519
uacgggacug uaacccugt t                                               21
```

```
<210> SEQ ID NO 520
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 520
cagguguuac agucccguat t                                              21

<210> SEQ ID NO 521
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 521
ugcuuccuug uuacagugut t                                              21

<210> SEQ ID NO 522
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 522
acacuguaac aaggaagcat t                                              21

<210> SEQ ID NO 523
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 523
ccuguugaau guuggguuct t                                              21

<210> SEQ ID NO 524
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 524
gaacccaaca uucaacaggt t                                              21
```

```
<210> SEQ ID NO 525
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 525
guugaauguu ggguuccugt t                                              21

<210> SEQ ID NO 526
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 526
caggaaccca acauucaact t                                              21

<210> SEQ ID NO 527
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 527
aauguugggu uccugaucct t                                              21

<210> SEQ ID NO 528
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 528
ggaucaggaa cccaacauut t                                              21

<210> SEQ ID NO 529
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 529
acacuaacag gaggagaaat t                                              21
```

```
<210> SEQ ID NO 530
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 530
uuucuccucc uguuagugut t                                           21

<210> SEQ ID NO 531
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 531
uauaagagga ggaguagaat t                                           21

<210> SEQ ID NO 532
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 532
uucuacuccu ccucuuauat t                                           21

<210> SEQ ID NO 533
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 533
auaagaggag gaguagaagt t                                           21

<210> SEQ ID NO 534
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 534
cuucuacucc uccucuuaut t                                           21
```

```
<210> SEQ ID NO 535
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 535
acuguaacac cugcucuugt t                                              21

<210> SEQ ID NO 536
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 536
caagagcagg uguuacagut t                                              21

<210> SEQ ID NO 537
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 537
ggacaugcuu ccuuguuact t                                              21

<210> SEQ ID NO 538
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 538
guaacaagga agcaugucct t                                              21

<210> SEQ ID NO 539
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 539
acaugcuucc uuguuacagt t                                              21
```

-continued

```
<210> SEQ ID NO 540
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 540
cuguaacaag gaagcaugut t                                                  21

<210> SEQ ID NO 541
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 541
augcuuccuu guuacagugt t                                                  21

<210> SEQ ID NO 542
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 542
cacuguaaca aggaagcaut t                                                  21

<210> SEQ ID NO 543
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 543
cuguugaaug uuggguucct t                                                  21

<210> SEQ ID NO 544
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 544
ggaacccaac auucaacagt t                                                  21
```

```
<210> SEQ ID NO 545
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 545
gaauguuggg uuccugauct t                                              21

<210> SEQ ID NO 546
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 546
gaucaggaac ccaacauuct t                                              21

<210> SEQ ID NO 547
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 547
cgggacugua acaccugcut t                                              21

<210> SEQ ID NO 548
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 548
agcagguguu acagucccgt t                                              21

<210> SEQ ID NO 549
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 549
ggacuguaac accugcucut t                                              21
```

```
<210> SEQ ID NO 550
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 550
agagcaggug uuacagucct t                                            21

<210> SEQ ID NO 551
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 551
gacuguaaca ccugcucuut t                                            21

<210> SEQ ID NO 552
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 552
aagagcaggu guuacaguct t                                            21

<210> SEQ ID NO 553
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 553
cuccagaaau gggugaccct t                                            21

<210> SEQ ID NO 554
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 554
gggucaccca uuucuggagt t                                            21
```

```
<210> SEQ ID NO 555
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 555
uaagaggagg aguagaagut t                                              21

<210> SEQ ID NO 556
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 556
acuucuacuc cuccucuuat t                                              21

<210> SEQ ID NO 557
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 557
gaggcugcug cuacuauagt t                                              21

<210> SEQ ID NO 558
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 558
cuauaguagc agcagccuct t                                              21

<210> SEQ ID NO 559
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 559
auugcauccc uugcuacugt t                                              21
```

```
<210> SEQ ID NO 560
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 560
caguagcaag ggaugcaaut t                                              21

<210> SEQ ID NO 561
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 561
ugcaucccuu gcuacuguat t                                              21

<210> SEQ ID NO 562
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 562
uacaguagca agggaugcat t                                              21

<210> SEQ ID NO 563
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 563 uuuguuuuc agguucaugt t                                               21

<210> SEQ ID NO 564
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 564
caugaaccug aaaacacaat t                                              21
```

```
<210> SEQ ID NO 565
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 565
ggaccuaguu gcuacuguut t                                           21

<210> SEQ ID NO 566
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 566
aacaguagca acuaggucct t                                           21

<210> SEQ ID NO 567
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 567
cugccacagg auuuucagut t                                           21

<210> SEQ ID NO 568
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 568
acugaaaauc cuguggcagt t                                           21

<210> SEQ ID NO 569
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 569
gcuacuauag aaguugaaat t                                           21
```

```
<210> SEQ ID NO 570
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 570
uuucaacuuc uauaguagct t                                              21

<210> SEQ ID NO 571
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 571
aauugcaucc cuugcuacut t                                              21

<210> SEQ ID NO 572
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 572
aguagcaagg gaugcaauut t                                              21

<210> SEQ ID NO 573
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 573
accuaguugc uacuguuuct t                                              21

<210> SEQ ID NO 574
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 574
gaaacaguag caacuaggut t                                              21
```

```
<210> SEQ ID NO 575
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 575
cuacuauaga aguugaaaut t                                              21

<210> SEQ ID NO 576
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 576
auuucaacuu cuauaguagt t                                              21

<210> SEQ ID NO 577
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 577
aggccuuacu ccugaaacat t                                              21

<210> SEQ ID NO 578
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 578
uguuucagga guaaggccut t                                              21

<210> SEQ ID NO 579
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 579
ggccuuacuc cugaaacaut t                                              21
```

```
<210> SEQ ID NO 580
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 580
auguuucagg aguaaggcct t                                              21

<210> SEQ ID NO 581
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 581
guaaaaccug gaguggaact t                                              21

<210> SEQ ID NO 582
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 582
guuccacucc agguuuuact t                                              21

<210> SEQ ID NO 583
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 583
uguguuuuca gguucauggt t                                              21

<210> SEQ ID NO 584
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 584
ccaugaaccu gaaaacacat t                                              21
```

```
<210> SEQ ID NO 585
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 585
uguuuucagg uucaugggut t                                              21

<210> SEQ ID NO 586
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 586
acccaugaac cugaaaacat t                                              21

<210> SEQ ID NO 587
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 587
aucccuugcu acuguagagt t                                              21

<210> SEQ ID NO 588
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 588
cucuacagua gcaagggaut t                                              21

<210> SEQ ID NO 589
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 589
gaccuaguug cuacuguuut t                                              21
```

```
<210> SEQ ID NO 590
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 590
aaacaguagc aacuagguct t                                            21

<210> SEQ ID NO 591
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 591
ggauuacaag uaccucugat t                                            21

<210> SEQ ID NO 592
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 592
ucagagguac uuguaaucct t                                            21

<210> SEQ ID NO 593
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 593
uaggccuuac uccugaaact t                                            21

<210> SEQ ID NO 594
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 594
guuucaggag uaaggccuat t                                            21
```

```
<210> SEQ ID NO 595
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 595
uguuagaauu uuugcuggat t                                          21

<210> SEQ ID NO 596
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 596
uccagcaaaa auucuaacat t                                          21

<210> SEQ ID NO 597
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 597
ugcugccaca ggauuuucat t                                          21

<210> SEQ ID NO 598
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 598
ugaaaauccu guggcagcat t                                          21

<210> SEQ ID NO 599
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 599
ccacaggauu uucaguagct t                                          21
```

```
<210> SEQ ID NO 600
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 600
gcuacugaaa auccuguggt t                                                   21

<210> SEQ ID NO 601
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 601
aaguugaaau ugcaucccut t                                                   21

<210> SEQ ID NO 602
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 602
agggaugcaa uuucaacuut t                                                   21

<210> SEQ ID NO 603
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 603
aguugaaauu gcaucccuut t                                                   21

<210> SEQ ID NO 604
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 604
aagggaugca auucaacut t                                                    21
```

-continued

```
<210> SEQ ID NO 605
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 605
gcugcugcca caggauuuut t                                            21

<210> SEQ ID NO 606
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 606
aaaauccugu ggcagcagct t                                            21

<210> SEQ ID NO 607
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 607
aguaaaaccu ggaguggaat t                                            21

<210> SEQ ID NO 608
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 608
uuccacucca gguuuuacut t                                            21

<210> SEQ ID NO 609
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 609
uuuuguguuu ucagguucat t                                            21
```

```
<210> SEQ ID NO 610
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 610
ugaaccugaa aacacaaaat t                                             21

<210> SEQ ID NO 611
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 611
uuuguguuuu cagguucaut t                                             21

<210> SEQ ID NO 612
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 612
augaaccuga aacacaaaat t                                             21

<210> SEQ ID NO 613
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 613
guguuuucag guucaugggt t                                             21

<210> SEQ ID NO 614
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 614
cccaugaacc ugaaaacact t                                             21
```

```
<210> SEQ ID NO 615
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 615 guuucaggu ucauggugt t                                              21

<210> SEQ ID NO 616
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 616
cacccaugaa ccugaaaact t                                            21

<210> SEQ ID NO 617
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 617
uuuucagguu caugggugct t                                            21

<210> SEQ ID NO 618
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 618
gcacccauga accugaaaat t                                            21

<210> SEQ ID NO 619
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 619
uuucagguuc augggugcct t                                            21
```

```
<210> SEQ ID NO 620
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 620
ggcacccaug aaccugaaat t                                          21

<210> SEQ ID NO 621
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 621
aauugcugcu ggagaggcut t                                          21

<210> SEQ ID NO 622
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 622
agccucucca gcagcaauut t                                          21

<210> SEQ ID NO 623
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 623
uugcaucccu ugcuacugut t                                          21

<210> SEQ ID NO 624
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 624
acaguagcaa gggaugcaat t                                          21
```

```
<210> SEQ ID NO 625
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 625
gcuguagcug gguuugcugt t                                              21

<210> SEQ ID NO 626
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 626
cagcaaaccc agcuacagct t                                              21

<210> SEQ ID NO 627
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 627
uagaaguuga aauugcauct t                                              21

<210> SEQ ID NO 628
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 628
gaugcaauuu caacuucuat t                                              21

<210> SEQ ID NO 629
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 629
gaaguugaaa uugcauccct t                                              21
```

```
<210> SEQ ID NO 630
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 630
gggaugcaau uucaacuuct t                                              21

<210> SEQ ID NO 631
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 631
caucccuugc uacuguagat t                                              21

<210> SEQ ID NO 632
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 632
ucuacaguag caagggaugt t                                              21

<210> SEQ ID NO 633
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 633
uaguaaaacc uggaguggat t                                              21

<210> SEQ ID NO 634
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 634
uccacuccag guuuuacuat t                                              21
```

```
<210> SEQ ID NO 635
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 635
uuuuuuguua gaauuuuugt t                                              21

<210> SEQ ID NO 636
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 636
caaaaauucu aacaaaaaat t                                              21

<210> SEQ ID NO 637
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 637
uacuauagaa guugaaauut t                                              21

<210> SEQ ID NO 638
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 638
aauuucaacu ucuauaguat t                                              21

<210> SEQ ID NO 639
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 639
ccuaguugcu acuguuucut t                                              21
```

```
<210> SEQ ID NO 640
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 640
agaaacagua gcaacuaggt t                                            21

<210> SEQ ID NO 641
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 641
cuaguugcua cuguuucugt t                                            21

<210> SEQ ID NO 642
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 642
cagaaacagu agcaacuagt t                                            21

<210> SEQ ID NO 643
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 643
guugcuacug uuucugaggt t                                            21

<210> SEQ ID NO 644
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 644
ccucagaaac aguagcaact t                                            21
```

```
<210> SEQ ID NO 645
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 645
uggagaggcu gcugcuacut t                                            21

<210> SEQ ID NO 646
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 646
aguagcagca gccucuccat t                                            21

<210> SEQ ID NO 647
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 647
gagaggcugc ugcuacuaut t                                            21

<210> SEQ ID NO 648
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 648
auaguagcag cagccucuct t                                            21

<210> SEQ ID NO 649
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 649
agaggcugcu gcuacuauat t                                            21
```

```
<210> SEQ ID NO 650
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 650
uauaguagca gcagccucut t                                              21

<210> SEQ ID NO 651
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 651
gcugcugcua cuauagaagt t                                              21

<210> SEQ ID NO 652
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 652
cuucuauagu agcagcagct t                                              21

<210> SEQ ID NO 653
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 653
uuuuuugugu uuucagguut t                                              21

<210> SEQ ID NO 654
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 654
aaccugaaaa cacaaaaaat t                                              21
```

```
<210> SEQ ID NO 655
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 655
acuauagaag uugaaauugt t                                            21

<210> SEQ ID NO 656
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 656
caauuucaac uucuauagut t                                            21

<210> SEQ ID NO 657
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 657
uuaguaaaac cuggaguggt t                                            21

<210> SEQ ID NO 658
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 658
ccacuccagg uuuuacuaat t                                            21

<210> SEQ ID NO 659
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 659
gccuuacucc ugaaacauat t                                            21
```

```
<210> SEQ ID NO 660
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 660
uauguuucag gaguaaggct t                                              21

<210> SEQ ID NO 661
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 661
agaaguugaa auugcaucct t                                              21

<210> SEQ ID NO 662
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 662
ggaugcaauu ucaacuucut t                                              21

<210> SEQ ID NO 663
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 663
ugccacagga uuuucaguat t                                              21

<210> SEQ ID NO 664
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 664
uacugaaaau ccuguggcat t                                              21
```

```
<210> SEQ ID NO 665
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 665
gcugccacag gauuuucagt t                                             21

<210> SEQ ID NO 666
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 666
cugaaaaucc uguggcagct t                                             21

<210> SEQ ID NO 667
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 667
cagguucaug ggugccgcat t                                             21

<210> SEQ ID NO 668
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 668
ugcggcaccc augaaccugt t                                             21

<210> SEQ ID NO 669
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 669
aaauugcugc uggagaggct t                                             21
```

```
<210> SEQ ID NO 670
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 670
gccucuccag cagcaauuut t                                              21

<210> SEQ ID NO 671
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 671
auugcugcug gagaggcugt t                                              21

<210> SEQ ID NO 672
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 672
cagccucucc agcagcaaut t                                              21

<210> SEQ ID NO 673
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 673
ugaaauugca ucccuugcut t                                              21

<210> SEQ ID NO 674
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 674
agcaagggau gcaauuucat t                                              21
```

```
<210> SEQ ID NO 675
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 675 uuuguuaga auuuugcut t                                            21

<210> SEQ ID NO 676
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 676
agcaaaaauu cuaacaaat t                                           21

<210> SEQ ID NO 677
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 677
uuuguuagaa uuuuugcugt t                                          21

<210> SEQ ID NO 678
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 678
cagcaaaaau ucuaacaaat t                                          21

<210> SEQ ID NO 679
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 679
ggcugcugcu acuauagaat t                                          21
```

```
<210> SEQ ID NO 680
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 680
uucuauagua gcagcagcct t                                            21

<210> SEQ ID NO 681
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 681
uuguuagaau uuuugcuggt t                                            21

<210> SEQ ID NO 682
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 682
ccagcaaaaa uucuaacaat t                                            21

<210> SEQ ID NO 683
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 683
uuuuuuugug uuuucaggut t                                            21

<210> SEQ ID NO 684
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 684
accugaaaac acaaaaaaat t                                            21
```

```
<210> SEQ ID NO 685
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 685
gaaacuacuu gggcaauagt t                                            21

<210> SEQ ID NO 686
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 686
cuauugccca aguaguuuct t                                            21

<210> SEQ ID NO 687
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 687
aauggauguu gccuuuacut t                                            21

<210> SEQ ID NO 688
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 688
aguaaaggca acauccauut t                                            21

<210> SEQ ID NO 689
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 689
ccucaaugga uguugccuut t                                            21
```

```
<210> SEQ ID NO 690
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 690
aaggcaacau ccauugaggt t                                              21

<210> SEQ ID NO 691
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 691
uugccuuuac uuuuagggut t                                              21

<210> SEQ ID NO 692
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 692
acccuaaaag uaaaggcaat t                                              21

<210> SEQ ID NO 693
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 693
agaaacuacu ugggcaauat t                                              21

<210> SEQ ID NO 694
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 694
uauugcccaa guaguuucut t                                              21
```

```
<210> SEQ ID NO 695
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 695
aagaaacuac uugggcaaut t                                              21

<210> SEQ ID NO 696
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 696
auugcccaag uaguuucuut t                                              21

<210> SEQ ID NO 697
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 697
ugccuuuacu uuuaggguut t                                              21

<210> SEQ ID NO 698
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 698
aacccuaaaa guaaaggcat t                                              21

<210> SEQ ID NO 699
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 699
gccuuuacuu uuaggguugt t                                              21
```

```
<210> SEQ ID NO 700
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 700
caacccuaaa aguaaaggct t                                              21

<210> SEQ ID NO 701
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 701
cuuuacuuuu aggguuguat t                                              21

<210> SEQ ID NO 702
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 702
uacaacccua aaaguaaagt t                                              21

<210> SEQ ID NO 703
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 703
uuuacuuuua ggguuguact t                                              21

<210> SEQ ID NO 704
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 704
guacaacccu aaaaguaaat t                                              21
```

-continued

```
<210> SEQ ID NO 705
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 705
uacuuuuagg guuguacggt t                                             21

<210> SEQ ID NO 706
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 706
ccguacaacc cuaaaaguat t                                             21

<210> SEQ ID NO 707
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 707
ggaagaaacu acuugggcat t                                             21

<210> SEQ ID NO 708
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 708
ugcccaagua guuucuucct t                                             21

<210> SEQ ID NO 709
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 709
caauggaugu ugccuuuact t                                             21
```

```
<210> SEQ ID NO 710
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 710
guaaaggcaa cauccauugt t                                              21

<210> SEQ ID NO 711
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 711
ggauguugcc uuuacuuuut t                                              21

<210> SEQ ID NO 712
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 712
aaaaguaaag gcaacaucct t                                              21

<210> SEQ ID NO 713
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 713
uguugccuuu acuuuuaggt t                                              21

<210> SEQ ID NO 714
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 714
ccuaaaagua aaggcaacat t                                              21
```

```
<210> SEQ ID NO 715
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 715
gauguugccu uacuuuuat t                                              21

<210> SEQ ID NO 716
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 716
uaaaaguaaa ggcaacauct t                                             21

<210> SEQ ID NO 717
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 717
ccagaagacu acuaugauat t                                             21

<210> SEQ ID NO 718
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 718
uaucauagua gucuucuggt t                                             21

<210> SEQ ID NO 719
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 719
uccagaagac uacuaugaut t                                             21
```

```
<210> SEQ ID NO 720
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 720
aucauaguag ucuucuggat t                                             21

<210> SEQ ID NO 721
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 721
uuuggaagaa acuacuuggt t                                             21

<210> SEQ ID NO 722
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 722
ccaaguaguu ucuuccaaat t                                             21

<210> SEQ ID NO 723
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 723
cuccucaaug gauguugcct t                                             21

<210> SEQ ID NO 724
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 724
ggcaacaucc auugaggagt t                                             21
```

```
<210> SEQ ID NO 725
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 725
ccaaaugugc aaucggugt t                                                  21

<210> SEQ ID NO 726
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 726
caccagauug cacauuuggt t                                                 21

<210> SEQ ID NO 727
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 727
caaaugugca aucggugat t                                                  21

<210> SEQ ID NO 728
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 728
ucaccagauu gcacauuugt t                                                 21

<210> SEQ ID NO 729
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 729
agaucugcuc cucaauggat t                                                 21
```

```
<210> SEQ ID NO 730
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 730
uccauugagg agcagaucut t                                         21

<210> SEQ ID NO 731
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 731
cucaauggau guugccuuut t                                         21

<210> SEQ ID NO 732
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 732
aaaggcaaca uccauugagt t                                         21

<210> SEQ ID NO 733
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 733
gcucaaauuu uauauaagat t                                         21

<210> SEQ ID NO 734
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 734
ucuuauauaa aauuugagct t                                         21
```

```
<210> SEQ ID NO 735
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 735
agccugauuu ugguacaugt t                                             21

<210> SEQ ID NO 736
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 736
cauguaccaa aaucaggcut t                                             21

<210> SEQ ID NO 737
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 737
cucaaauuuu auauaagaat t                                             21

<210> SEQ ID NO 738
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 738
uucuuauaua aaauuugagt t                                             21

<210> SEQ ID NO 739
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 739
acaaagugcu gaauagggat t                                             21
```

```
<210> SEQ ID NO 740
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 740
ucccuauuca gcacuuugut t                                              21

<210> SEQ ID NO 741
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 741
cugauuuugg uacauggaat t                                              21

<210> SEQ ID NO 742
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 742
uuccauguac caaaaucagt t                                              21

<210> SEQ ID NO 743
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 743
gauuuuggua cauggaauat t                                              21

<210> SEQ ID NO 744
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 744
uauuccaugu accaaaauct t                                              21
```

```
<210> SEQ ID NO 745
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 745
cucaucagcc ugauuuggt t                                              21

<210> SEQ ID NO 746
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 746
ccaaaaucag gcugaugagt t                                             21

<210> SEQ ID NO 747
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 747
agcccacuug uuggauagt t                                              21

<210> SEQ ID NO 748
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 748
cuauccacac aagugggcut t                                             21

<210> SEQ ID NO 749
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 749
gugcugaaua gggaggaaut t                                             21
```

```
<210> SEQ ID NO 750
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 750
auuccucccu auucagcact t                                            21

<210> SEQ ID NO 751
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 751
aguaagggcg uggaggcuut t                                            21

<210> SEQ ID NO 752
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 752
aagccuccac gcccuuacut t                                            21

<210> SEQ ID NO 753
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 753
gugacuuaac ccaagaagct t                                            21

<210> SEQ ID NO 754
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 754
gcuucuuggg uuaagucact t                                            21
```

```
<210> SEQ ID NO 755
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 755
uaguaagggc guggaggcut t                                              21

<210> SEQ ID NO 756
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 756
agccuccacg cccuuacuat t                                              21

<210> SEQ ID NO 757
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 757
ucaucagccu gauuuuggut t                                              21

<210> SEQ ID NO 758
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 758
accaaaauca ggcugaugat t                                              21

<210> SEQ ID NO 759
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 759
guagaagacc cuaaagacut t                                              21
```

```
<210> SEQ ID NO 760
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 760
agucuuuagg gucuucuact t                                              21

<210> SEQ ID NO 761
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 761
agguagaaga cccuaaagat t                                              21

<210> SEQ ID NO 762
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 762
ucuuuagggu cuucuaccut t                                              21

<210> SEQ ID NO 763
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 763
aaaagguaga agacccuaat t                                              21

<210> SEQ ID NO 764
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 764
uuagggucuu cuaccuuuut t                                              21
```

```
<210> SEQ ID NO 765
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 765
aaagguagaa gacccuaaat t                                             21

<210> SEQ ID NO 766
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 766
uuuagggucu ucuaccuuut t                                             21

<210> SEQ ID NO 767
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 767
gauugugcag uggaaagaat t                                             21

<210> SEQ ID NO 768
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 768
uucuuuccac ugcacaauct t                                             21

<210> SEQ ID NO 769
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 769
ggauugugca guggaaagat t                                             21
```

```
<210> SEQ ID NO 770
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 770
ucuuuccacu gcacaaucct t                                                21

<210> SEQ ID NO 771
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 771
uguagacagc cauaugcagt t                                                21

<210> SEQ ID NO 772
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 772
cugcauaugg cugucuacat t                                                21

<210> SEQ ID NO 773
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 773
caugacuuua acccagaagt t                                                21

<210> SEQ ID NO 774
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 774
cuucuggguu aaagucaugt t                                                21
```

```
<210> SEQ ID NO 775
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 775
auagggagga auccauggat t                                              21

<210> SEQ ID NO 776
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 776
uccauggauu ccucccuaut t                                              21

<210> SEQ ID NO 777
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 777
cugaauaggg aggaauccat t                                              21

<210> SEQ ID NO 778
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 778
uggauuccuc ccuauucagt t                                              21

<210> SEQ ID NO 779
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 779
aaagugcuga auagggaggt t                                              21
```

```
<210> SEQ ID NO 780
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 780
ccucccuauu cagcacuuut t                                              21

<210> SEQ ID NO 781
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 781
ugacuuaacc caagaagcut t                                              21

<210> SEQ ID NO 782
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 782
agcuucuugg guuaagucat t                                              21

<210> SEQ ID NO 783
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 783
augacuuuaa cccagaagat t                                              21

<210> SEQ ID NO 784
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 784
ucuucugggu uaaagucaut t                                              21
```

```
<210> SEQ ID NO 785
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 785
gaagacccua aagacuuuct t                                            21

<210> SEQ ID NO 786
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 786
gaaagucuuu agggucuuct t                                            21

<210> SEQ ID NO 787
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 787
aaaaagcuca aauuuuauat t                                            21

<210> SEQ ID NO 788
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 788
uauaaaauuu gagcuuuuut t                                            21

<210> SEQ ID NO 789
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 789
aucagccuga uuuugguact t                                            21
```

-continued

```
<210> SEQ ID NO 790
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 790
guaccaaaau caggcugaut t                                             21

<210> SEQ ID NO 791
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 791
caucagccug auuuugguat t                                             21

<210> SEQ ID NO 792
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 792
uaccaaaauc aggcugaugt t                                             21

<210> SEQ ID NO 793
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 793
auggacaaag ugcugaauat t                                             21

<210> SEQ ID NO 794
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 794
uauucagcac uuuguccaut t                                             21
```

```
<210> SEQ ID NO 795
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 795
uagaagaccc uaaagacuut t                                               21

<210> SEQ ID NO 796
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 796
aagucuuuag ggucuucuat t                                               21

<210> SEQ ID NO 797
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 797
aagguagaag acccuaaagt t                                               21

<210> SEQ ID NO 798
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 798
cuuuaggguc uucuaccuut t                                               21

<210> SEQ ID NO 799
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 799
cagcccacuu guguggauat t                                               21
```

```
<210> SEQ ID NO 800
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 800
uauccacaca aguggggcugt t                                            21

<210> SEQ ID NO 801
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 801
uuuugguaca uggaauagut t                                             21

<210> SEQ ID NO 802
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 802
acuauuccau guaccaaaat t                                             21

<210> SEQ ID NO 803
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 803
ugaauaggga ggaauccaut t                                             21

<210> SEQ ID NO 804
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 804
auggauuccu cccuauucat t                                             21
```

```
<210> SEQ ID NO 805
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 805
gcugaauagg gaggaaucct t                                             21

<210> SEQ ID NO 806
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 806 ggauccucc cuauucagct t                                              21

<210> SEQ ID NO 807
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 807
ugcugaauag ggaggaauct t                                             21

<210> SEQ ID NO 808
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 808
gauuccuccc uauucagcat t                                             21

<210> SEQ ID NO 809
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 809
uguguagaca gccauaugct t                                             21
```

```
<210> SEQ ID NO 810
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 810
gcauauggcu gucuacacat t                                              21

<210> SEQ ID NO 811
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 811
ugcuuugauu gcuucagact t                                              21

<210> SEQ ID NO 812
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 812
gucugaagca aucaaagcat t                                              21

<210> SEQ ID NO 813
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 813
uugcuuugau ugcuucagat t                                              21

<210> SEQ ID NO 814
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 814
ucugaagcaa ucaaagcaat t                                              21
```

```
<210> SEQ ID NO 815
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 815
auugcuuuga uugcuucagt t                                             21

<210> SEQ ID NO 816
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 816
cugaagcaau caaagcaaut t                                             21

<210> SEQ ID NO 817
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 817
cuauugcuuu gauugcuuct t                                             21

<210> SEQ ID NO 818
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 818
gaagcaauca aagcaauagt t                                             21

<210> SEQ ID NO 819
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 819
auugcaagga auggccuaat t                                             21
```

```
<210> SEQ ID NO 820
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 820
uuaggccauu ccuugcaaut t                                           21

<210> SEQ ID NO 821
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 821
auuuuccucc uaauucugat t                                           21

<210> SEQ ID NO 822
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 822
ucagaauuag gaggaaaaut t                                           21

<210> SEQ ID NO 823
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 823
gcucaucagc cugauuuugt t                                           21

<210> SEQ ID NO 824
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 824
caaaaucagg cugaugagct t                                           21
```

```
<210> SEQ ID NO 825
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 825
ugcucaucag ccugauuuut t                                             21

<210> SEQ ID NO 826
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 826
aaaaucaggc ugaugagcat t                                             21

<210> SEQ ID NO 827
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 827
aguugcucau cagccugaut t                                             21

<210> SEQ ID NO 828
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 828
aucaggcuga ugagcaacut t                                             21

<210> SEQ ID NO 829
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 829
aagggcgugg aggcuuuuut t                                             21
```

```
<210> SEQ ID NO 830
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 830
aaaaagccuc cacgcccuut t                                              21

<210> SEQ ID NO 831
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 831
guaagggcgu ggaggcuuut t                                              21

<210> SEQ ID NO 832
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 832
aaagccucca cgcccuuact t                                              21

<210> SEQ ID NO 833
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 833
gacccuaaag acuuccugt t                                               21

<210> SEQ ID NO 834
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 834
caggaaaguc uuuaggguct t                                              21
```

```
<210> SEQ ID NO 835
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 835
aggagcauga cuuuaaccct t                                            21

<210> SEQ ID NO 836
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 836
ggguuaaagu caugcuccut t                                            21

<210> SEQ ID NO 837
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 837
ugugauuuuc cuccuaauut t                                            21

<210> SEQ ID NO 838
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 838
aauuaggagg aaaaucacat t                                            21

<210> SEQ ID NO 839
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 839
uugugauuuu ccuccuaaut t                                            21
```

```
<210> SEQ ID NO 840
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 840
auuaggagga aaaucacaat t                                            21

<210> SEQ ID NO 841
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 841
gacuuaaccc aagaagcuct t                                            21

<210> SEQ ID NO 842
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 842
gagcuucuug gguuaaguct t                                            21

<210> SEQ ID NO 843
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 843
gcuucagaca augguuggt t                                             21

<210> SEQ ID NO 844
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 844
ccaaaccauu gucugaagct t                                            21
```

```
<210> SEQ ID NO 845
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 845
uugcuucaga caaugguuut t                                              21

<210> SEQ ID NO 846
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 846
aaaccauugu cugaagcaat t                                              21

<210> SEQ ID NO 847
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 847
auugcuucag acaaugguut t                                              21

<210> SEQ ID NO 848
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 848
aaccauuguc ugaagcaaut t                                              21

<210> SEQ ID NO 849
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 849
uugauugcuu cagacaaugt t                                              21
```

```
<210> SEQ ID NO 850
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 850
cauugucuga agcaaucaat t                                              21

<210> SEQ ID NO 851
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 851
gacaaagugc ugaauagggt t                                              21

<210> SEQ ID NO 852
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 852
cccuauucag cacuuuguct t                                              21

<210> SEQ ID NO 853
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 853
aagaaaaagc ucaaauuuut t                                              21

<210> SEQ ID NO 854
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 854
aaaauuugag cuuuuucuut t                                              21
```

```
<210> SEQ ID NO 855
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 855
aaagaaaaag cucaaauuut t                                              21

<210> SEQ ID NO 856
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 856
aaauuugagc uuuuucuuut t                                              21

<210> SEQ ID NO 857
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 857
agaagacccu aaagacuuut t                                              21

<210> SEQ ID NO 858
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 858
aaagucuuua gggucuucut t                                              21

<210> SEQ ID NO 859
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 859
aaaaaaaagg uagaagacct t                                              21
```

```
<210> SEQ ID NO 860
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 860
ggucuucuac cuuuuuuut t                                           21

<210> SEQ ID NO 861
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 861
gguagaagac ccuaaagact t                                          21

<210> SEQ ID NO 862
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 862
gucuuuaggg ucuucuacct t                                          21

<210> SEQ ID NO 863
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 863
aaaaaaggua gaagacccut t                                          21

<210> SEQ ID NO 864
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 864
agggucuucu accuuuuuut t                                          21
```

```
<210> SEQ ID NO 865
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 865
aaaaagguag aagacccuat t                                            21

<210> SEQ ID NO 866
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 866
uagggucuuc uaccuuuuut t                                            21

<210> SEQ ID NO 867
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 867
uuaacccaag aagcucuuct t                                            21

<210> SEQ ID NO 868
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 868
gaagagcuuc uuggguuaat t                                            21

<210> SEQ ID NO 869
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 869
auuuugguac auggaauagt t                                            21
```

```
<210> SEQ ID NO 870
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 870
cuauuccaug uaccaaaaut t                                             21

<210> SEQ ID NO 871
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 871
agugcugaau agggaggaat t                                             21

<210> SEQ ID NO 872
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 872
uuccucccua uucagcacut t                                             21

<210> SEQ ID NO 873
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 873
gaggccaggg aaauucccut t                                             21

<210> SEQ ID NO 874
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 874
agggaauuuc ccuggccuct t                                             21
```

```
<210> SEQ ID NO 875
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 875
agcucaaauu uuauauaagt t                                               21

<210> SEQ ID NO 876
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 876
cuuauauaaa auuugagcut t                                               21

<210> SEQ ID NO 877
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 877
cagggaaauu cccuuguuut t                                               21

<210> SEQ ID NO 878
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 878
aaacaaggga auuucccugt t                                               21

<210> SEQ ID NO 879
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 879
uugugcagug gaaagaaagt t                                               21
```

```
<210> SEQ ID NO 880
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 880
cuuucuuucc acugcacaat t                                          21

<210> SEQ ID NO 881
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 881
uacauggaau aguucagagt t                                          21

<210> SEQ ID NO 882
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 882
cucugaacua uuccauguat t                                          21

<210> SEQ ID NO 883
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 883
guacauggaa uaguucagat t                                          21

<210> SEQ ID NO 884
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 884
ucugaacuau uccauguact t                                          21
```

```
<210> SEQ ID NO 885
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 885
agggaaauuc ccuuguuuut t                                              21

<210> SEQ ID NO 886
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 886
aaaacaaggg aauuucccut t                                              21

<210> SEQ ID NO 887
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 887
ggaggccagg gaaauuccct t                                              21

<210> SEQ ID NO 888
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 888
gggaauuucc cuggccucct t                                              21

<210> SEQ ID NO 889
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 889
guguagacag ccauaugcat t                                              21
```

```
<210> SEQ ID NO 890
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 890
ugcauauggc ugucuacact t                                              21

<210> SEQ ID NO 891
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 891
guagacagcc auaugcagut t                                              21

<210> SEQ ID NO 892
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 892
acugcauaug gcugucuact t                                              21

<210> SEQ ID NO 893
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 893
gaagaccugu uuugccaugt t                                              21

<210> SEQ ID NO 894
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 894
cauggcaaaa caggucuuct t                                              21
```

```
<210> SEQ ID NO 895
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 895
agugggauga agaccuguut t                                                  21

<210> SEQ ID NO 896
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 896
aacaggucuu caucccacut t                                                  21

<210> SEQ ID NO 897
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 897
ugaagaccug uuuugccaut t                                                  21

<210> SEQ ID NO 898
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 898
auggcaaaac aggucuucat t                                                  21

<210> SEQ ID NO 899
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 899
ugggaugaag accuguuuut t                                                  21
```

```
<210> SEQ ID NO 900
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 900
aaaacagguc uucaucccat t                                             21

<210> SEQ ID NO 901
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 901
cuuaacccaa gaagcucuut t                                             21

<210> SEQ ID NO 902
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 902
aagagcuucu uggguuaagt t                                             21

<210> SEQ ID NO 903
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 903
auugugcagu ggaaagaaat t                                             21

<210> SEQ ID NO 904
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 904
uuucuuucca cugcacaaut t                                             21
```

```
<210> SEQ ID NO 905
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 905
cuuuauugca aggaauggct t                                              21

<210> SEQ ID NO 906
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 906
gccauuccuu gcaauaaagt t                                              21

<210> SEQ ID NO 907
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 907
gagcaugacu uuaacccagt t                                              21

<210> SEQ ID NO 908
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 908
cuggguuaaa gucaugcuct t                                              21

<210> SEQ ID NO 909
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 909
gugauuuucc uccuaauuct t                                              21
```

```
<210> SEQ ID NO 910
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 910
gaauuaggag gaaaaucact t                                              21

<210> SEQ ID NO 911
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 911
ugauugcuuc agacaauggt t                                              21

<210> SEQ ID NO 912
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 912
ccauugucug aagcaaucat t                                              21

<210> SEQ ID NO 913
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 913
aagcucaaau uuuauauaat t                                              21

<210> SEQ ID NO 914
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 914
uuauauaaaa uuugagcuut t                                              21
```

```
<210> SEQ ID NO 915
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 915
cuggacaugg aucaagcact t                                             21

<210> SEQ ID NO 916
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 916
gugcuugauc cauguccagt t                                             21

<210> SEQ ID NO 917
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 917
ucaaauuuua uauaagaaat t                                             21

<210> SEQ ID NO 918
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 918
uuucuuauau aaaauuugat t                                             21

<210> SEQ ID NO 919
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 919
ugugcagugg aaagaaaggt t                                             21
```

```
<210> SEQ ID NO 920
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 920
ccuuucuuuc cacugcacat t                                              21

<210> SEQ ID NO 921
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 921
uugguacaug gaauaguuct t                                              21

<210> SEQ ID NO 922
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 922
gaacuauucc auguaccaat t                                              21

<210> SEQ ID NO 923
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 923
aagugggaug aagaccugut t                                              21

<210> SEQ ID NO 924
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 924 acagucuuc aucccacuut t                                               21
```

```
<210> SEQ ID NO 925
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 925
ggaugaagac cuguuuugct t                                              21

<210> SEQ ID NO 926
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 926
gcaaaacagg ucuucaucct t                                              21

<210> SEQ ID NO 927
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 927
ucuggacaug gaucaagcat t                                              21

<210> SEQ ID NO 928
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 928
ugcuugaucc auguccagat t                                              21

<210> SEQ ID NO 929
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 929
uuugguacau ggaauaguut t                                              21
```

```
<210> SEQ ID NO 930
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 930
aacuauucca uguaccaaat t                                              21

<210> SEQ ID NO 931
<211> LENGTH: 1202
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 931
ctcgagactt ttagggttgt acgggactgt aacacctgct cttgaagcat atgaagatgg     60
ccccaacaaa aagaaaagga gaaaggaagg accccgtgca agttccaaaa cttcttataa    120
gaggaggagt agaagttcta gaagttaaaa ctggggttga ctcaattaca gaggtagaat    180 gcttttaac  tccagaaatg ggtgacccag atgagcatct tagggttttt agtaagtcaa    240
tttctatatc agatacattt gaaagtgact ccccaaataa ggacatgctt ccttgttaca    300
gtgtggccag aattccacta cccaatctaa atgaggatct aacctgtgga aatatactaa    360
tgtgggaggc tgtgacctta aaaactgagg ttctaggggt gacaactttg atgaatgtgc    420
actctaatgg tcaagcaact catgacaatg gtgcaggaaa gccagtgcag ggcaccagct    480 ttcattttt  ttctgttggc ggggaggctt tagaattaca ggggtggtt  tttaattaca    540 gaacaaagta cccagatgga acaattttttc caaagaatgc aacagtgcaa tctcaagtaa    600
tgaacacaga gcacaaggcg tacctagata agaacaaagc atatcctgtt gaatgttggg    660
ttcctgatcc caccagaaat gaaaacacaa gatattttgg gacactaaca ggaggagaaa    720
atgttcctcc agttcttcat ataacaaaca ctgccacaac agtgctgctt gatgaatttg    780
gtgttgggcc actttgcaaa ggtgacaact tgtatttgtc agctgttgat gtttgtggaa    840
tgtttactaa cagatctggt tcccagcagt ggagaggact gtccagatat tttaaggttc    900
agctcagaaa aaggagggtt aaaaaccccct acccaatttc tttccttctt actgatttga    960
ttaacagaag  daccccctaga gttgatgggc aacctatgta tggtatggat gctcaggtag   1020
aggaggttag agttttttgag gggacagagg aacttccagg ggacccagac atgatgagat   1080
atgttgacag atatggacag ttgcaaacaa agatgctgta atcaaaatcc tttattgtaa   1140
tatgcagtac atttaataa agtataacca gctttacttt acagttgcag tcatgcggcc   1200
gc                                                                 1202

<210> SEQ ID NO 932
<211> LENGTH: 2479
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 932
ctcgagccgc ctccaagctt actcagaagt agtaagggcg tggaggcttt ttaggaggcc     60
```

```
agggaaattc ccttgttttt ccctttttg cagtaatttt ttgctgcaaa aagctaaaat      120
ggacaaagtg ctgaataggg aggaatccat ggagcttatg gatttattag gccttgatag     180
gtctgcatgg gggaacattc ctgtcatgag aaaagcttat ctgaaaaaat gcaaagaact     240
ccaccctgat aaaggtgggg acgaagacaa gatgaagaga atgaattttt tatataaaaa     300
aatggaacaa ggtgtaaaag ttgctcatca gcctgatttt ggtacatgga atagttcaga     360
ggttggttgt gattttcctc ctaattctga tacccttat tgcaaggaat ggcctaactg      420
tgccactaat ccttcagtgc attgcccctg tttaatgtgc atgctaaaat taaggcatag     480
aaacagaaaa ttttaagaa gcagcccact tgtgtggata gattgctatt gctttgattg      540
cttcagacaa tggtttgggt gtgacttaac ccaagaagct cttcattgct gggagaaagt     600
tcttggagac acccctaca gggatctaaa gctttaagtg ccaacctatg aacagatga      660
atgggaatcc tggtgaata catttaatga gaagtgggat gaagacctgt tttgccatga     720
agaaatgttt gccagtgatg atgaaaacac aggatcccaa cactctaccc cacctaaaaa     780
gaaaaaaag gtagaagacc ctaaagactt tcctgtagat ctgcatgcat tcctcagtca     840
agctgtgttt agtaatagaa ctgttgcttc tttgctgtg taccacta aagaaaaagc       900
tcaaatttta taagaaac ttatggaaaa atattctgta actttataa gtagacatgg        960
ttttgggggt cataatattt tgtttttctt aacaccacat agacatagag tgtcagcaat    1020
taataactac tgtcaaaaac tatgtacctt tagttttta atttgtaaag gtgtgaataa    1080
ggaatacttg ttttatagtg ccctgtgtag acagccatat gcagtagtgg aagaaagtat    1140
tcaggggggc cttaaggagc atgactttaa cccagaagaa ccagaagaaa ctaagcaggt    1200
ttcatggaaa ttagttacac agtatgcctt ggaaaccaag tgtgaggatg ttttttgct    1260
tatgggcatg tacttagact ttcaggaaaa cccacagcaa tgcaaaaaat gtgaaaaaaa    1320
ggatcagcca atcacttta accatcatga aaaacactat tataatgccc aaatttttgc     1380
agatagcaaa aatcaaaaaa gcatttgcca gcaggctgtt gatactgtag cagccaaaca    1440
aagggttgac agcatccaca tgaccagaga agaaatgtta gttgaaaggt ttaattctt    1500
gcttgataaa atggacttaa ttttgggc acatggcaat gctgttttag agcaatatat      1560
ggctgggtg gcctggattc attgcttgct gcctcaaatg gacactgtta tttatgactt     1620
tctaaaatgc attgtattaa acattccaaa aaaaggtac tggctattca agggccaat      1680
agacagtggc aaaactactt tagctgcagc tttacttgat ctctgtgggg gaaagtcatt    1740
aaatgttaat atgccattag aaagattaaa ctttgaatta ggagtgggta tagatcagtt    1800
tatggttgta tttgaggatg taaaaggcac tggtgcagag tcaagggatt taccttcagg    1860
gcatggcata agcaaccttg attgcttaag agattactta gatggaagtg taaaagttaa    1920
tttagagaga aaacaccaaa acaaaagaac acaggtgttt ccacctggaa ttgtaaccat    1980
gaatgaatat tcagtgccta gaactttaca ggccagattt gtaaggcaga tagattttag    2040
accaaaggcc tacctgagaa aatcactaag ctgctctgag tatttgctag aaaaaggat     2100
tttgcaaagt ggtatgactt tgcttttgct tttaatctgg tttaggccag ttgctgactt    2160
tgcagctgcc attcatgaga ggattgtgca gtggaagaa aggctggatt tagaaataag     2220
catgtataca ttttctacta tgaaagctaa tgttggtatg gggagaccca ttcttgactt    2280
tcctagagag gaagattctg aagcagaaga ctctggacat ggatcaagca ctgaatcaca    2340
atcacaatgc ttttccagg tctcagaagc ctctggtgca gacacacagg aaaactgcac     2400
ttttcacatc tgtaaaggct ttcaatgttt caaaaaacca aagacccctc ccccaaaata    2460
```
actgcaactg tgcggccgc 2479

<210> SEQ ID NO 933
<211> LENGTH: 708
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 933

| | | |
|---|---|---|
| ctcgagcagc taacagccag taaacaaagc acaaggggaa gtggaaagca gccaagggaa | 60 | |
| catgttttgc gagccagagc tgttttggct tgtcaccagc tggccatggt tcttcgccag | 120 | |
| ctgtcacgta aggcttctgt gaaagttagt aaaacctgga gtggaactaa aaaaagagct | 180 | |
| caaaggattt taattttttt gttagaattt ttgctggact tttgcacagg tgaagacagt | 240 | |
| gtagacggga aaaaaagaca gagacacagt ggtttgactg agcagacata cagtgctttg | 300 | |
| cctgaaccaa aagctacata ggtaagtaat gttttttttt gtgttttcag gttcatgggt | 360 | |
| gccgcacttg cacttttggg ggacctagtt gctactgttt ctgaggctgc tgctgccaca | 420 | |
| ggattttcag tagctgaaat tgctgctgga gaggctgctg ctactataga agttgaaatt | 480 | |
| gcatcccttg ctactgtaga ggggattaca agtacctctg aggctatagc tgctataggc | 540 | |
| cttactcctg aaacatatgc tgtaataact ggagctccgg gggctgtagc tgggtttgct | 600 | |
| gcattggttc aaactgtaac tggtggtagt gctattgctc agttgggata tagattttt | 660 | |
| gctgactggg atcataaagt ttcaacagtt gggcttttc gcggccgc | 708 | |

<210> SEQ ID NO 934
<211> LENGTH: 738
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 934

| | | |
|---|---|---|
| ctcgagagca gccagctatg gctttacaat tatttaatcc agaagactac tatgatattt | 60 | |
| tatttcctgg agtgaatgcc tttgttaaca atattcacta tttagatcct agacattggg | 120 | |
| gcccgtcctt gttctccaca atctcccagg cttttggaa tcttgttaga gatgatttgc | 180 | |
| cagccttaac ctctcaggaa attcagaaa gaacccaaaa actatttgtt gaaagtttag | 240 | |
| caaggttttt ggaagaaact acttgggcaa tagttaattc accagctaac ttatataatt | 300 | |
| atatttcaga ctattattct agattgtctc cagttaggcc ctctatggta aggcaagttg | 360 | |
| cccaaaggga gggaacctat atttcttttg gccactcata cacccaaagt atagatgatg | 420 | |
| cagacagcat tcaagaagtt acccaaaggc tagatttaaa aaccccaaat gtgcaatctg | 480 | |
| gtgaatttat agaagaagt attgcaccag gaggtgcaaa tcaaagatct gctcctcaat | 540 | |
| ggatgttgcc tttactttta gggttgtacg ggactgtaac acctgctctt gaagcatatg | 600 | |
| aagatggccc caacaaaaag aaaaggagaa aggaaggacc ccgtgcaagt tccaaaactt | 660 | |
| cttataagag gaggagtaga agttctagaa gttaaaactg gggttgactc aattacagag | 720 | |
| gtagaatgct gcggccgc | 738 | |

<210> SEQ ID NO 935
<211> LENGTH: 19
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 935
uguugaaugu uggguuccu                                                  19

<210> SEQ ID NO 936
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 936
uguugaaugu uggguuccut t                                               21

<210> SEQ ID NO 937
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 937
aggaacccaa cauucaacat t                                               21
```

COMPOSITIONS AND METHODS FOR INHIBITING EXPRESSION OF A GENE FROM THE JC VIRUS

RELATED APPLICATIONS

This application is a continuation of U.S. application Ser. No. 11/741,205, filed Apr. 27, 2007 (now U.S. Pat. No. 7,691,824) and claims the benefit of U.S. Provisional Application No. 60/795,765, filed Apr. 28, 2006; both applications are incorporated herein by reference in their entirety.

REFERENCE TO A SEQUENCE LISTING

The instant application contains a Sequence Listing which has been submitted via EFS-Web and is hereby incorporated by reference in its entirety. Said ASCII copy, created on May 3, 2011, is named 16408US_CRF_sequencelisting.txt and is 312,511 bytes in size.

FIELD OF THE INVENTION

This invention relates to double-stranded ribonucleic acid (dsRNA), and its use in mediating RNA interference to inhibit the expression of one of the genes of the JC virus and the use of the dsRNA to treat pathological processes mediated by JC virus infection, such as PML.

BACKGROUND OF THE INVENTION

Progressive multifocal leukoencephalopathy (PML) is a fatal demyelinating disease of the central nervous system which results from reactivation of the latent polyomavirus JC virus (JCV) and its productive replication in glial cells of the human brain (Berger, J. R. (1995) J. Neurovirol. 1:5-18). Once a rare disease primarily seen in patients with impaired immune systems due to lymphoproliferative and myeloproliferative disorders, PML has become one of the major neurologic problems among patients with AIDS (Cinque, P., (2003). J. Neurovirol. 9(Suppl. 1):88-92).

It has been reported that between 4 and 8% of AIDS patients exhibit signs of PML, and JCV has been detected in the cerebrospinal fluid of affected patients, suggesting that there is active replication of the virus in the brain (Berger, J. R. (1995) J. Neurovirol. 1:5-18, Clifford, D. B., (2001) J. Neurovirol. 4:279). In addition, PML has recently been seen in patients undergoing experimental treatment with Tsybari, an anti VLA4 antobody, in combination with interferon. The histological hallmarks of PML include multifocal demyelinated lesions with enlarged eosinophilic nuclei in oligodendrocytes and enlarged bizarre astrocytes with lobulated hyperchromatic nuclei within white matter tracts of the brain (Cinque, P., (2003). J. Neurovirol. 9(Suppl. 1):88-92), although in some instances atypical features that include a unifocal pattern of demyelination and involvement of the gray matter have been reported (Sweeney, B. J., (1994). J. Neurol. Neurosurg. Psychiatry 57:994-997). Earlier observations from in vitro cell culture studies and an in vivo evaluation of JCV in clinical samples led to early assumptions that oligodendrocytes and astrocytes are the only cells which support productive viral infections (Gordon, J. (1998) Int. J. Mol. Med. 1:647-655). Accordingly, molecular studies have provided evidence for cell-type-specific transcription of the viral early genome in cells derived from the central nervous system (Raj, G. V., (1995) Virology 10:283-291). However, subsequent studies have shown low, but detectable, levels of JCV gene expression in nonneural cells, including B cells, and noticeably high levels of production of the viral early protein in several neural and nonneural tumor cells in humans (Gordon, J. (1998) Int. J. Mol. Med. 1:647-655, Khalili, K., 2003. Oncogene 22:5181-5191).

Like the other polyomaviruses, JCV is a small DNA virus whose genome can be divided into three regions that encompass the transcription control region; the genes responsible for the expression of the viral early protein, T antigen; and the genes encoding the viral late proteins, VP1, VP2, and VP3. In addition, the late genome is also responsible for production of an auxiliary viral protein, agnoprotein. T-antigen expression is pivotal for initiation of the viral lytic cycle, as this protein stimulates transcription of the late genes and induces the process of viral DNA replication. Recent studies have ascribed an important role for agnoprotein in the transcription and replication of JCV, as inhibition of its production significantly reduced viral gene expression and replication (M. Safak et al., unpublished observations). Furthermore, the agnoprotein dysregulates the cell cycle by altering the expression of several cyclins and their associated kinases (Darbinyan, A., (2002) Oncogene 21:5574-5581).

Thus far, there are no effective therapies for the suppression of JCV replication and the treatment of PML. Cytosine arabinoside (AraC) has been tested for the treatment of PML patients, and the outcome in some instances revealed a remission of JCV-associated demyelination (Aksamit, A. (2001) J. Neurovirol. 7:386-390). Reports from the AIDS Clinical Trial Group Organized Trial 243, however, have suggested that there is no difference in the survival of human immunodeficiency virus type 1 (HIV-1)-infected patients with PML and that of the control population, although in other reports it has been suggested that the failure of AraC in the AIDS Clinical Trial Group trial may have been due to insufficient delivery of the AraC via the intravenous and intrathecal routes (Levy, R. M., (2001) J. Neurovirol. 7:382-385). Based on in vitro studies showing the ability of inhibitors of topoisomerase to suppress JCV DNA replication, the topoisomerase inhibitor topotecan was used for the treatment of AIDS-PML patients, and the results suggested that topotecan treatment may be associated with a decreased lesion size and prolonged survival (Royal, W., III, (2003) J. Neurovirol. 9:411-419).

Double-stranded RNA molecules (dsRNA) have been shown to block gene expression in a highly conserved regulatory mechanism known as RNA interference (RNAi). WO 99/32619 (Fire et al.) discloses the use of a dsRNA of at least 25 nucleotides in length to inhibit the expression of genes in *C. elegans*. dsRNA has also been shown to degrade target RNA in other organisms, including plants (see, e.g., WO 99/53050, Waterhouse et al.; and WO 99/61631, Heifetz et al.), *Drosophila* (see, e.g., Yang, D., et al., Curr. Biol. (2000) 10:1191-1200), and mammals (see WO 00/44895, Limmer; and DE 101 00 586.5, Kreutzer et al.). This natural mechanism has now become the focus for the development of a new class of pharmaceutical agents for treating disorders that are caused by the aberrant or unwanted regulation of a gene.

Recent reports have indicated that in vitro, RNAi may show some promise in reducing JC virus replication (Radhakrishnan, S. (2004) J. Vir. 78:7264-7269, Orba, Y. (2004) J. Vir. 78:7270-7273). However, the RNAi agents examined were not designed against all know JC Virus strains and were not selected for stability and other properties need for in vivo therapeutic RNAi agents. Accordingly, despite significant advances in the field of RNAi, there remains a need for an agent that can selectively and efficiently silence a gene in the JC virus using the cell's own RNAi machinery that has both high biological activity and in vivo stability, and that can

SUMMARY OF THE INVENTION

The invention provides double-stranded ribonucleic acid (dsRNA), as well as compositions and methods for inhibiting the expression of the JC virus in a cell or mammal using such dsRNA. The invention also provides compositions and methods for treating pathological conditions and diseases caused by JC viral infection, such as PML. The dsRNA of the invention comprises an RNA strand (the antisense strand) having a region which is less than 30 nucleotides in length, generally 19-24 nucleotides in length, and is substantially complementary to at least part of an mRNA transcript of a gene from the JC Virus.

In one embodiment, the invention provides double-stranded ribonucleic acid (dsRNA) molecules for inhibiting the expression one of the genes of the JC virus and viral replication. The dsRNA comprises at least two sequences that are complementary to each other. The dsRNA comprises a sense strand comprising a first sequence and an antisense strand comprising a second sequence. The antisense strand comprises a nucleotide sequence which is substantially complementary to at least part of an mRNA encoded by a gene from the JC Virus, and the region of complementarity is less than 30 nucleotides in length, generally 19-24 nucleotides in length. The dsRNA, upon contacting with a cell expressing infected with the JC virus, inhibits the expression of a gene from the JC Virus by at least 40%.

For example, the dsRNA molecules of the invention can be comprised of a first sequence of the dsRNA that is selected from the group consisting of the sense sequences of Tables 1a and b and the second sequence is selected from the group consisting of the antisense sequences of Tables 1a and b. The dsRNA molecules of the invention can be comprised of naturally occurring nucleotides or can be comprised of at least one modified nucleotide, such as a 2'-O-methyl modified nucleotide, a nucleotide comprising a 5'-phosphorothioate group, and a terminal nucleotide linked to a cholesteryl derivative. Alternatively, the modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Generally, such modified sequence will be based on a first sequence of said dsRNA selected from the group consisting of the sense sequences of Tables 1a and b and a second sequence selected from the group consisting of the antisense sequences of Tables 1a and 1b.

In another embodiment, the invention provides a cell comprising one of the dsRNAs of the invention. The cell is generally a mammalian cell, such as a human cell.

In another embodiment, the invention provides a pharmaceutical composition for inhibiting the replication of the JC virus in an organism, generally a human subject, comprising one or more of the dsRNA of the invention and a pharmaceutically acceptable carrier or delivery vehicle.

In another embodiment, the invention provides a method for inhibiting the expression of a gene in the JC Virus in a cell, comprising the following steps:

(a) introducing into the cell a double-stranded ribonucleic acid (dsRNA), wherein the dsRNA comprises at least two sequences that are complementary to each other. The dsRNA comprises a sense strand comprising a first sequence and an antisense strand comprising a second sequence. The antisense strand comprises a region of complementarity which is substantially complementary to at least a part of a mRNA encoded by the JC virus, and wherein the region of complementarity is less than 30 nucleotides in length, generally 19-24 nucleotides in length, and wherein the dsRNA, upon contact with a cell infected with the JC virus, inhibits expression of a gene from the JC Virus by at least 40%; and (b) maintaining the cell produced in step (a) for a time sufficient to obtain degradation of the mRNA transcript of a JC virus gene, thereby inhibiting expression of a gene from the JC Virus in the cell.

In another embodiment, the invention provides methods for treating, preventing or managing pathological processes mediated by JC virus infection, e.g. such as PML, comprising administering to a patient in need of such treatment, prevention or management a therapeutically or prophylactically effective amount of one or more of the dsRNAs of the invention.

In another embodiment, the invention provides vectors for inhibiting the expression of a gene of the JC virus in a cell, comprising a regulatory sequence operably linked to a nucleotide sequence that encodes at least one strand of one of the dsRNA of the invention.

In another embodiment, the invention provides a cell comprising a vector for inhibiting the expression of a gene of the JC virus in a cell. The vector comprises a regulatory sequence operably linked to a nucleotide sequence that encodes at least one strand of one of the dsRNA of the invention.

BRIEF DESCRIPTION OF THE FIGURES

No Figures are presented.

DETAILED DESCRIPTION OF THE INVENTION

The invention provides double-stranded ribonucleic acid (dsRNA), as well as compositions and methods for inhibiting the expression of a gene from the JC Virus in a cell or mammal using the dsRNA. The invention also provides compositions and methods for treating pathological conditions and diseases in a mammal caused by JC virus infection using dsRNA. dsRNA directs the sequence-specific degradation of mRNA through a process known as RNA interference (RNAi).

The dsRNA of the invention comprises an RNA strand (the antisense strand) having a region which is less than 30 nucleotides in length, generally 19-24 nucleotides in length, and is substantially complementary to at least part of an mRNA transcript of a gene from the JC Virus. The use of these dsRNAs enables the targeted degradation of mRNAs of genes that are implicated in replication and or maintenance of JC virus infection and the occurrence of PML in a subject infected with the JC virus. Using cell-based and animal assays, the present inventors have demonstrated that very low dosages of these dsRNA can specifically and efficiently mediate RNAi, resulting in significant inhibition of expression of a gene from the JC Virus. Thus, the methods and compositions of the invention comprising these dsRNAs are useful for treating pathological processes mediated by JC viral infection, e.g. cancer, by targeting a gene involved in JC virus replication and/or maintenance in a cell.

The following detailed description discloses how to make and use the dsRNA and compositions containing dsRNA to inhibit the expression of a gene from the JC virus, as well as compositions and methods for treating diseases and disorders caused by the infection with the JC virus, such as PML. The pharmaceutical compositions of the invention comprise a dsRNA having an antisense strand comprising a region of complementarity which is less than 30 nucleotides in length, generally 19-24 nucleotides in length, and is substantially complementary to at least part of an RNA transcript of a gene from the JC Virus, together with a pharmaceutically acceptable carrier.

Accordingly, certain aspects of the invention provide pharmaceutical compositions comprising the dsRNA of the invention together with a pharmaceutically acceptable carrier, methods of using the compositions to inhibit expression of a gene in a gene from the JC Virus, and methods of using the pharmaceutical compositions to treat diseases caused by infection with the JC virus.

I. Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A" and "U" each generally stand for a nucleotide that contains guanine, cytosine, adenine, and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

As used herein, "JC virus" refers to the latent polyomavirus JC Virus that has a reference sequence NC_001699. In addition, further accession numbers of various JC Virus sequences are AB038249.1-AB038255.1, AB048545.1-AB048582.1, AB074575.1-AB074591.1, AB077855.1-AB077879.1, AB081005.1-AB081030.1, AB081600.1-AB081618.1, AB081654.1, AB092578.1-AB092587.1, AB103387.1, AB103402.1-AB103423.1, AB104487.1, AB113118.1-AB113145.1, AB118651.1-AB118659.1, AB126981.1-AB127027.1, AB127342.1, AB127344.1, AB127346.1-AB127349.1, AB127352.1-AB127353.1, AB198940.1-AB198954.1, AB220939.1-AB220943.1, AF004349.1-AF004350.1, AF015526.1-AF015537.1, AF015684.1, AF030085.1, AF281599.1-AF281626.1, AF295731.1-AF295739.1, AF300945.1-AF300967.1, AF363830.1-AF363834.1, AF396422.1-AF396435.1, AY121907.1-AY121915.1, NC_001699.1, U61771.1, U73500.1-U73502.1.

As used herein, "target sequence" refers to a contiguous portion of the nucleotide sequence of an mRNA molecule formed during the transcription of a gene from the JC Virus, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes of the invention.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled.

The terms "complementary", "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide which is "substantially complementary to at least part of" a messenger RNA (mRNA) refers to a polynucleotide which is substantially complementary to a contiguous portion of the mRNA of interest (e.g., encoding JC virus). For example, a polynucleotide is complementary to at least a part of a JC virus mRNA if the sequence is substantially complementary to a non-interrupted portion of a mRNA encoding JC virus.

The term "double-stranded RNA" or "dsRNA", as used herein, refers to a complex of ribonucleic acid molecules, having a duplex structure comprising two anti-parallel and substantially complementary, as defined above, nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop". Where the two strands are connected covalently by means other than an uninterrupted chain of nucleotides between the 3'-end of one strand and the 5' end of the respective other strand forming the duplex structure, the connecting structure is referred to as a "linker". The RNA strands may have the same or a different number of nucleotides. The maximum number of base pairs is the number of nucleotides in the shortest strand of the dsRNA minus any overhangs that are present in the duplex. In addition to the duplex structure, a dsRNA may comprise one or more nucleotide overhangs.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

"Introducing into a cell", when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell", wherein the cell is part of a living organism. In such instance, introduction into the cell will include the delivery to the organism. For example, for in vivo delivery, dsRNA can be injected into a tissue site or administered systemically. In vitro introduction into a cell includes methods known in the art such as electroporation and lipofection.

The terms "silence" and "inhibit the expression of", in as far as they refer to a gene from the JC Virus, herein refer to the at least partial suppression of the expression of a gene from the JC Virus, as manifested by a reduction of the amount of mRNA transcribed from a gene from the JC Virus which may be isolated from a first cell or group of cells in which a gene from the JC Virus is transcribed and which has or have been treated such that the expression of a gene from the JC Virus is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to JC virus genome transcription, e.g. the amount of protein encoded by a gene from the JC Virus, or the number of cells displaying a certain phenotype, e.g infection with the JC Virus. In principle, JC virus genome silencing may be determined in any cell expressing the target, either constitutively or by genomic engineering, and by any appropriate assay. However, when a reference is needed in order to determine whether a given dsRNA inhibits the expression of a gene from the JC Virus by a certain degree and therefore is encompassed by the instant invention, the assay provided in the Examples below shall serve as such reference.

For example, in certain instances, expression of a gene from the JC Virus is suppressed by at least about 20%, 25%, 35%, or 50% by administration of the double-stranded oligonucleotide of the invention. In some embodiment, a gene from the JC Virus is suppressed by at least about 60%, 70%, or 80% by administration of the double-stranded oligonucleotide of the invention. In some embodiments, a gene from the JC Virus is suppressed by at least about 85%, 90%, or 95% by administration of the double-stranded oligonucleotide of the invention.

As used herein in the context of JC virus expression, the terms "treat", "treatment", and the like, refer to relief from or alleviation of pathological processes mediated by JC virus infection. In the context of the present invention insofar as it relates to any of the other conditions recited herein below (other than pathological processes mediated by JC virus expression), the terms "treat", "treatment", and the like mean to relieve or alleviate at least one symptom associated with such condition, or to slow or reverse the progression of such condition.

As used herein, the phrases "therapeutically effective amount" and "prophylactically effective amount" refer to an amount that provides a therapeutic benefit in the treatment, prevention, or management of pathological processes mediated by JC virus infection or an overt symptom of pathological processes mediated by JC virus expression. The specific amount that is therapeutically effective can be readily determined by ordinary medical practitioner, and may vary depending on factors known in the art, such as, e.g. the type of pathological processes mediated by JC virus infection, the patient's history and age, the stage of pathological processes mediated by JC virus infection, and the administration of other anti-pathological processes mediated by JC virus infection.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a vector has been introduced from which a dsRNA molecule may be expressed.

II. Double-Stranded Ribonucleic Acid (dsRNA)

In one embodiment, the invention provides double-stranded ribonucleic acid (dsRNA) molecules for inhibiting the expression of a gene from the JC Virus in a cell or mammal, wherein the dsRNA comprises an antisense strand comprising a region of complementarity which is complementary to at least a part of an mRNA formed in the expression of a gene from the JC Virus, and wherein the region of complementarity is less than 30 nucleotides in length, generally 19-24 nucleotides in length, and wherein said dsRNA, upon contact with a cell expressing the gene from the JC virus, inhibits the expression of the JC virus gene by at least 40%.

The dsRNA comprises two RNA strands that are sufficiently complementary to hybridize to form a duplex structure. One strand of the dsRNA (the antisense strand) comprises a region of complementarity that is substantially complementary, and generally fully complementary, to a target sequence, derived from the sequence of an mRNA formed during the expression of a gene from the JC Virus, the other strand (the sense strand) comprises a region which is complementary to the antisense strand, such that the two strands hybridize and form a duplex structure when combined under suitable conditions. Generally, the duplex structure is between 15 and 30, more generally between 18 and 25, yet more generally between 19 and 24, and most generally between 19 and 21 base pairs in length. Similarly, the region of complementarity to the target sequence is between 15 and 30, more generally between 18 and 25, yet more generally between 19 and 24, and most generally between 19 and 21 nucleotides in length. The dsRNA of the invention may further comprise one or more single-stranded nucleotide overhang(s).

The dsRNA can be synthesized by standard methods known in the art as further discussed below, e.g., by use of an automated DNA synthesizer, such as are commercially available from, for example, Biosearch, Applied Biosystems, Inc. In a preferred embodiment, a gene from the JC Virus is the human JC virus genome. In specific embodiments, the antisense strand of the dsRNA comprises the sense sequences of Tables 1a and b and the second sequence is selected from the group consisting of the antisense sequences of Tables 1a and b. Alternative antisense agents that target elsewhere in the target sequence provided in Tables 1a and b can readily be determined using the target sequence and the flanking JC virus sequence.

In further embodiments, the dsRNA comprises at least one nucleotide sequence selected from the groups of sequences provided in Tables 1a and b. In other embodiments, the dsRNA comprises at least two sequences selected from this group, wherein one of the at least two sequences is complementary to another of the at least two sequences, and one of the at least two sequences is substantially complementary to a sequence of an mRNA generated in the expression of a gene from the JC Virus. Generally, the dsRNA comprises two oligonucleotides, wherein one oligonucleotide is described as the sense strand in Tables 1a and b and the second oligonucleotide is described as the antisense strand in Tables 1a and b.

The skilled person is well aware that dsRNAs comprising a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well. In the embodiments described above, by virtue of the nature of the oligonucleotide sequences provided in Tables 1a and b, the dsRNAs of the invention can comprise at least one strand of a length of minimally 21 nt. It can be reasonably expected that shorter dsRNAs comprising one of the sequences of Tables 1a and b minus only a few nucleotides on one or both ends may be similarly effective as compared to the dsRNAs described above. Hence, dsRNAs comprising a partial sequence of at least 15, 16, 17, 18, 19, 20, or more contiguous nucleotides from one of the sequences of Tables 1a and b, and differing in their ability to inhibit the expression of a gene from the JC Virus in a FACS assay as described herein below by not more than 5, 10, 15, 20, 25, or 30% inhibition from a dsRNA comprising the full sequence, are contemplated by the invention. Further dsRNAs that cleave within the target sequence provided in Tables 1a and b can readily be made using the JC virus sequence and the target sequence provided.

In addition, the RNAi agents provided in Tables 1a and b identify a site in the JC virus mRNA that is susceptible to RNAi based cleavage. As such the present invention further includes RNAi agents that target within the sequence targeted by one of the agents of the present invention. As used herein a second RNAi agent is said to target within the sequence of a first RNAi agent if the second RNAi agent cleaves the message anywhere within the mRNA that is complementary to the antisense strand of the first RNAi agent. Such a second agent will generally consist of at least 15 contiguous nucleotides from one of the sequences provided in Tables 1a and b coupled to additional nucleotide sequences taken from the region contiguous to the selected sequence in a gene from the JC Virus. For example, the last 15 nucleotides of SEQ ID NO:1 combined with the next 6 nucleotides from the target JC virus genome produces a single strand agent of 21 nucleotides that is based on one of the sequences provided in Tables 1a and b.

The dsRNA of the invention can contain one or more mismatches to the target sequence. In a preferred embodiment, the dsRNA of the invention contains no more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide dsRNA strand which is complementary to a region of a gene from the JC Virus, the dsRNA generally does not contain any mismatch within the central 13 nucleotides. The methods described within the invention can be used to determine whether a dsRNA containing a mismatch to a target sequence is effective in inhibiting the expression of a gene from the JC Virus. Consideration of the efficacy of dsRNAs with mismatches in inhibiting expression of a gene from the JC Virus is important, especially if the particular region of complementarity in a gene from the JC Virus is known to have polymorphic sequence variation within the population.

In one embodiment, at least one end of the dsRNA has a single-stranded nucleotide overhang of 1 to 4, generally 1 or 2 nucleotides. dsRNAs having at least one nucleotide overhang have unexpectedly superior inhibitory properties than their blunt-ended counterparts. Moreover, the present inventors have discovered that the presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The dsRNA may also have a blunt end, generally located at the 5'-end of the antisense strand. Such dsRNAs have improved stability and inhibitory activity, thus allowing administration at low dosages, i.e., less than 5 mg/kg body weight of the recipient per day. Generally, the antisense strand of the dsRNA has a nucleotide overhang at the 3'-end, and the 5'-end is blunt. In another embodiment, one or more of the nucleotides in the overhang is replaced with a nucleoside thiophosphate.

In yet another embodiment, the dsRNA is chemically modified to enhance stability. The nucleic acids of the invention may be synthesized and/or modified by methods well established in the art, such as those described in "Current protocols in nucleic acid chemistry", Beaucage, S. L. et al. (Edrs.), John Wiley & Sons, Inc., New York, N.Y., USA, which is hereby incorporated herein by reference. Specific examples of preferred dsRNA compounds useful in this invention include dsRNAs containing modified backbones or no natural internucleoside linkages. As defined in this specification, dsRNAs having modified backbones include those that retain a phosphorus atom in the backbone and those that do not have a phosphorus atom in the backbone. For the purposes of this specification, and as sometimes referenced in the art, modified dsRNAs that do not have a phosphorus atom in their internucleoside backbone can also be considered to be oligonucleosides.

Preferred modified dsRNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476, 301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; and 5,625,050, each of which is herein incorporated by reference.

Preferred modified dsRNA backbones that do not include a phosphorus atom therein have backbones that are formed by short chain alkyl or cycloalkyl internucleoside linkages, mixed heteroatoms and alkyl or cycloalkyl internucleoside linkages, or ore or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other preferred dsRNA mimetics, both the sugar and the internucleoside linkage, i.e., the backbone, of the nucleotide units are replaced with novel groups. The base units are maintained for hybridization with an appropriate nucleic acid target compound. One such oligomeric compound, an dsRNA mimetic that has been shown to have excellent hybridization properties, is referred to as a peptide nucleic acid (PNA). In PNA compounds, the sugar backbone of an dsRNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Most preferred embodiments of the invention are dsRNAs with phosphorothioate backbones and oligonucleosides with heteroatom backbones, and in particular —$CH_2$—NH—$CH_2$-, —$CH_2$-N($CH_3$)-O—$CH_2$-[known as a methylene (methylimino) or MMI backbone], —$CH_2$-O—N($CH_3$)-$CH_2$-, —$CH_2$-N($CH_3$)-N($CH_3$)-$CH_2$- and —N($CH_3$)-$CH_2$-$CH_2$-[wherein the native phosphodiester backbone is represented as —O—P—O—$CH_2$-] of the above-referenced U.S. Pat. No. 5,489,677, and the amide backbones of the above-referenced U.S. Pat. No. 5,602,240. Also preferred are dsRNAs having morpholino backbone structures of the above-referenced U.S. Pat. No. 5,034,506.

Modified dsRNAs may also contain one or more substituted sugar moieties. Preferred dsRNAs comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$NH$_2$, O($CH_2$)$_n$$CH_3$, O($CH_2$)$_n$ONH$_2$, and O($CH_2$)$_n$ON[($CH_2$)$_n$$CH_3$)]$_2$, where n and m are from 1 to about 10. Other preferred dsRNAs comprise one of the following at the 2' position: $C_1$ to $C_{10}$ lower alkyl, substituted lower alkyl, alkaryl, aralkyl, O-alkaryl or O-aralkyl, SH, S$CH_3$, OCN, Cl, Br, CN, $CF_3$, OCF$_3$, SO$CH_3$, SO$_2$$CH_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an dsRNA, or a group for improving the pharmacodynamic properties of an dsRNA, and other substituents having similar properties. A preferred modification includes 2'-methoxyethoxy (2'-O—$CH_2$$CH_2$O$CH_3$, also known as 2'-O-(2-methoxyethyl) or 2'-MOE) (Martin et al., Helv. Chim. Acta, 1995, 78, 486-504) i.e., an alkoxy-alkoxy group. A further preferred modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—CH$_2$-O—CH$_2$-N(CH$_2$)$_2$, also described in examples hereinbelow.

Other preferred modifications include 2'-methoxy (2'-OCH$_3$), 2'-aminopropoxy (2'-OCH$_2$CH$_2$CH$_2$NH$_2$) and 2'-fluoro (2'-F). Similar modifications may also be made at other positions on the dsRNA, particularly the 3' position of the sugar on the 3' terminal nucleotide or in 2'-5' linked dsRNAs and the 5' position of 5' terminal nucleotide. DsRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

dsRNAs may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, DsRNA Research and Applications, pages 289-302, Crooke, S. T. and Lebleu, B., Ed., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., Eds., DsRNA Research and Applications, CRC Press, Boca Raton, 1993, pp. 276-278) and are presently preferred base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, each of which is herein incorporated by reference, and U.S. Pat. No. 5,750,692, also herein incorporated by reference.

Another modification of the dsRNAs of the invention involves chemically linking to the dsRNA one or more moieties or conjugates which enhance the activity, cellular distribution or cellular uptake of the dsRNA. Such moieties include but are not limited to lipid moieties such as a cholesterol moiety (Letsinger et al., Proc. Natl. Acid. Sci. USA, 199, 86, 6553-6556), cholic acid (Manoharan et al., Biorg. Med. Chem. Let., 1994 4 1053-1060), a thioether, e.g., beryl-S-tritylthiol (Manoharan et al., Ann. N.Y. Acad. Sci., 1992, 660, 306-309; Manoharan et al., Biorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-Hphosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyloxycholesterol moiety (Crooke et al., J. Pharmacol. Exp. Ther., 1996, 277, 923-937).

Representative U.S. patents that teach the preparation of such dsRNA conjugates include, but are not limited to, U.S. Pat. Nos. 4,828,979; 4,948,882; 5,218,105; 5,525,465; 5,541, 313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an dsRNA. The present invention also includes dsRNA compounds which are chimeric compounds. "Chimeric" dsRNA compounds or "chimeras," in the context of this invention, are dsRNA compounds, particularly dsRNAs, which contain two or more chemically distinct regions, each made up of at least one monomer unit, i.e., a nucleotide in the case of an dsRNA compound. These dsRNAs typically contain at least one region wherein the dsRNA is modified so as to confer upon the dsRNA increased resistance to nuclease degradation, increased cellular uptake, and/or increased binding affinity for the target nucleic acid. An additional region of the dsRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of dsRNA inhibition of gene expression. Consequently, comparable results can often be obtained with shorter dsRNAs when chimeric dsRNAs are used, compared to phosphorothioate deoxydsRNAs hybridizing to the same target region. Cleavage of the RNA target can be routinely detected by gel electrophoresis and, if necessary, associated nucleic acid hybridization techniques known in the art.

In certain instances, the dsRNA may be modified by a non-ligand group. A number of non-ligand molecules have been conjugated to dsRNAs in order to enhance the activity, cellular distribution or cellular uptake of the dsRNA, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-S-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such dsRNA conjugates have been listed above. Typical conjugation protocols involve the synthesis of dsRNAs bearing an aminolinker at one or more positions of the sequence. The amino group is then reacted with the molecule being conjugated using appropriate coupling or activating reagents. The conjugation reaction may be performed either with the dsRNA still bound to the solid support or following cleavage of the dsRNA in solution phase. Purification of the dsRNA conjugate by HPLC typically affords the pure conjugate.

Vector Encoded RNAi Agents

The dsRNA of the invention can also be expressed from recombinant viral vectors intracellularly in vivo. The recombinant viral vectors of the invention comprise sequences encoding the dsRNA of the invention and any suitable promoter for expressing the dsRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the dsRNA in a particular tissue or in a particular intracellular environment. The use of recombinant viral vectors to deliver dsRNA of the invention to cells in vivo is discussed in more detail below.

dsRNA of the invention can be expressed from a recombinant viral vector either as two separate, complementary RNA molecules, or as a single RNA molecule with two complementary regions.

Any viral vector capable of accepting the coding sequences for the dsRNA molecule(s) to be expressed can be used, for example vectors derived from adenovirus (AV); adeno-associated virus (AAV); retroviruses (e.g, lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J E et al. (2002), J Virol 76:791-801, the entire disclosure of which is herein incorporated by reference.

Selection of recombinant viral vectors suitable for use in the invention, methods for inserting nucleic acid sequences for expressing the dsRNA into the vector, and methods of delivering the viral vector to the cells of interest are within the skill in the art. See, for example, Dornburg R (1995), Gene Therap. 2: 301-310; Eglitis M A (1988), Biotechniques 6: 608-614; Miller A D (1990), Hum Gene Therap. 1: 5-14; Anderson W F (1998), Nature 392: 25-30; and Rubinson D A et al., Nat. Genet. 33: 401-406, the entire disclosures of which are herein incorporated by reference.

Preferred viral vectors are those derived from AV and AAV. In a particularly preferred embodiment, the dsRNA of the invention is expressed as two separate, complementary single-stranded RNA molecules from a recombinant AAV vector comprising, for example, either the U6 or H1 RNA promoters, or the cytomegalovirus (CMV) promoter.

A suitable AV vector for expressing the dsRNA of the invention, a method for constructing the recombinant AV vector, and a method for delivering the vector into target cells, are described in Xia H et al. (2002), Nat. Biotech. 20: 1006-1010.

Suitable AAV vectors for expressing the dsRNA of the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

III. Pharmaceutical Compositions Comprising dsRNA

In one embodiment, the invention provides pharmaceutical compositions comprising a dsRNA, as described herein, and a pharmaceutically acceptable carrier. The pharmaceutical composition comprising the dsRNA is useful for treating a disease or disorder associated with the expression or activity of a gene from the JC Virus and/or viral infection, such as PML. Such pharmaceutical compositions are formulated based on the mode of delivery. One example is compositions that are formulated for systemic administration via parenteral delivery.

The pharmaceutical compositions of the invention are administered in dosages sufficient to inhibit expression of a gene from the JC Virus. The present inventors have found that, because of their improved efficiency, compositions comprising the dsRNA of the invention can be administered at surprisingly low dosages. A maximum dosage of 5 mg dsRNA per kilogram body weight of recipient per day is sufficient to inhibit or completely suppress expression of a gene from the JC Virus.

In general, a suitable dose of dsRNA will be in the range of 0.01 to 5.0 milligrams per kilogram body weight of the recipient per day, generally in the range of 1 microgram to 1 mg per kilogram body weight per day. The pharmaceutical composition may be administered once daily, or the dsRNA may be administered as two, three, or more sub-doses at appropriate intervals throughout the day or even using continuous infusion or delivery through a controlled release formulation. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases, such as pathological processes mediated by JC virus expression. Such models are used for in vivo testing of dsRNA, as well as for determining a therapeutically effective dose.

The present invention also includes pharmaceutical compositions and formulations which include the dsRNA compounds of the invention. The pharmaceutical compositions of the present invention may be administered in a number of ways depending upon whether local or systemic treatment is desired and upon the area to be treated. Administration may be topical, pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term “liposome” means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P.Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside G.sub.M1, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside G.sub.M1, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside G.sub.M1 or a galactocerebroside sulfate ester. U.S. Pat. No. 5,543,152 (Webb et al.) discloses liposomes comprising sphingomyelin. Liposomes comprising 1,2-sn-dimyristoylphosphat-idylcholine are disclosed in WO 97/13499 (Lim et al).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, 2C.sub.1215G, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556, 948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an dsRNA RNA. U.S. Pat. No. 5,665,710 to Rahman et al. describes certain methods of encapsulating oligodeoxynucleotides in liposomes. WO 97/04787 to Love et al. discloses liposomes comprising dsRNA dsRNAs targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Agents that enhance uptake of dsRNAs at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, The Merck Manual of Diagnosis and Therapy, 15th Ed., Berkow et al., eds., 1987, Rahway, N.J., pages 2499-2506 and 46-49, respectively). Other non-antisense chemotherapeutic agents are also within the scope of this invention. Two or more combined compounds may be used together or sequentially.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the invention lies generally within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the dsRNAs of the invention can be administered in combination with other known agents effective in treatment of pathological processes mediated by JC virus expression. In any event, the administering physician can adjust the amount and timing of dsRNA administration on the basis of results observed using standard measures of efficacy known in the art or described herein.

Methods for Treating Diseases Caused by Expression of a Gene from the JC Virus

The invention relates in particular to the use of a dsRNA or a pharmaceutical composition prepared therefrom for the treatment or prevention of pathological conditions associated with JC Virus infection, e.g., PML. Owing to the inhibitory effect on JC virus expression, an dsRNA according to the invention or a pharmaceutical composition prepared therefrom can enhance the quality of life, particularly in a patient being treated with an anti-VLA4 antibody as part of treatment for MS.

The invention furthermore relates to the use of an dsRNA or a pharmaceutical composition thereof for treating PML in combination with other pharmaceuticals and/or other therapeutic methods, e.g., with known pharmaceuticals and/or known therapeutic methods, such as, for example, those which are currently employed for treating cancer and/or for preventing tumor metastasis. Preference is given to a combination with radiation therapy and chemotherapeutic agents, such as cisplatin, cyclophosphamide, 5-fluorouracil, adriamycin, daunorubicin or tamoxifen.

The invention can also be practiced by including with a specific RNAi agent, in combination with another anti-cancer chemotherapeutic agent, such as any conventional chemotherapeutic agent. The combination of a specific binding agent with such other agents can potentiate the chemotherapeutic protocol. Numerous chemotherapeutic protocols will present themselves in the mind of the skilled practitioner as being capable of incorporation into the method of the invention. Any chemotherapeutic agent can be used, including alkylating agents, antimetabolites, hormones and antagonists, radioisotopes, as well as natural products. For example, the compound of the invention can be administered with antibiotics such as doxorubicin and other anthracycline analogs, nitrogen mustards such as cyclophosphamide, pyrimidine analogs such as 5-fluorouracil, cisplatin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of a tetracycline compound with another treatment modality, e.g., surgery, radiation, etc., also referred to herein as "adjunct antineoplastic modalities." Thus, the method of the invention can be employed with such conventional regimens with the benefit of reducing side effects and enhancing efficacy.

Methods for Inhibiting Expression of a Gene from the JC Virus

In yet another aspect, the invention provides a method for inhibiting the expression of a gene from the JC Virus in a mammal. The method comprises administering a composition of the invention to the mammal such that expression of the target JC virus genome is silenced. Because of their high specificity, the dsRNAs of the invention specifically target RNAs (primary or processed) of the target JC virus gene. Compositions and methods for inhibiting the expression of these JC virus genes using dsRNAs can be performed as described elsewhere herein.

In one embodiment, the method comprises administering a composition comprising a dsRNA, wherein the dsRNA comprises a nucleotide sequence which is complementary to at least a part of an RNA transcript of a gene from the JC Virus, to the mammal to be treated. When the organism to be treated is a mammal such as a human, the composition may be administered by any means known in the art including, but not limited to oral or parenteral routes, including intravenous, intramuscular, subcutaneous, transdermal, airway (aerosol), nasal, administration. In preferred embodiments, the compositions are administered by intravenous infusion or injection.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Design of JCV siRNAs

Full-length genome sequences to JC virus available on Apr. 10, 2006, were obtained, resulting in a target pool of 388 sequences (accession numbers: AB038249.1-AB038255.1; AB048545.1-AB048582.1; AB074575.1-AB074591.1; AB077855.1-AB077879.1; AB081005.1-AB081030.1; AB081600.1-AB081618.1; AB081654.1; AB092578.1-AB092587.1; AB103387.1; AB103402.1-AB103423.1; AB104487.1; AB113118.1-AB113145.1; AB118651.1-AB118659.1; AB126981.1-AB127027.1; AB127342.1; AB127344.1; AB127346.1-AB127349.1; AB127352.1-AB127353.1; AB198940.1-AB198954.1; AB220939.1-AB220943.1; AF004349.1-AF004350.1; AF015526.1-AF015537.1; AF015684.1; AF030085.1; AF281599.1-AF281626.1; AF295731.1-AF295739.1; AF300901.1-AF300967.1; AF363830.1-AF363834.1; AF396422.1-AF396435.1; AY121907.1-AY121915.1; NC_001699.1; U61771.1; U73500.1-U73502.1). NC_001699 was defined as reference sequence.

The siRNA selection process was run as follows: ClustalW multiple alignment was used to generate a global alignment of all sequences from the target pool. An IUPAC consensus sequence was then generated.

All conserved 19mer target sequences from the IUPAC consensus represented by stretches containing only A, T, C or G bases, which are therefore present in all sequences of the target pool were selected. In order to only select siRNAs that target transcribed sequence parts of the JC virus, candidate target sequences were selected out of the pool of conserved 19mer target sequences. For this, candidate target sequences covering regions between nucleotide 163-2594 and between 2527-5115 relative to reference sequence were extracted for late and early genes, respectively. Further, as sequences for early genes are in reverse complement orientation compared with genomic sequences, candidate target sequences of these genes were transferred to reverse complement sequences and replaced the former pool of candidate target sequences.

In order to rank candidate target sequences and their respective siRNAs and select appropriate ones, their predicted potential for interacting with irrelevant targets (off-target potential) was taken as a ranking parameter. siRNAs with low off-target potential were defined as preferable and assumed to be more specific in vivo.

For predicting siRNA-specific off-target potential, the following assumptions were made:
1) positions 2 to 9 (counting 5' to 3') of a strand (seed region) may contribute more to off-target potential than rest of sequence (non-seed and cleavage site region)
2) positions 10 and 11 (counting 5' to 3') of a strand (cleavage site region) may contribute more to off-target potential than non-seed region
3) an off-target score can be calculated for each hit, based on identity to siRNA sequence and position of mismatches
4) assuming potential abortion of sense strand activity by internal modifications introduced, only off-target potential of antisense strand will be relevant To identify potential off-target genes, 19mer input sequences were subjected to a homology search against publically available human mRNA sequences.

To this purpose, fastA (version 3.4) searches were performed with all 19mer candidate target sequences against a human RefSeq database (downloaded available version from ftp://ftp.ncbi.nih.gov/refseq/ on Nov. 7, 2006). FastA searches were executed with parameters-values-pairs −f 50 −g 50 in order to take into account the homology over the full length of the 19mer without any gaps. In order to ensure the listing of all relevant off-target hits in the fastA output file the parameter −E 30000 was used in addition. A scoring matrix was applied for the run that assessed every nucleotide match with a score of 13 and every mismatch with a score of −7. The search resulted in a list of potential off-targets for each candidate siRNA.

To sort the resulting list of potential off-targets for each siRNA, fastA output files were analyzed to identify the best off-target and its off-target score. The following off-target properties for each 19mer input sequence were extracted for each off-target to calculate the off-target score:
Number of mismatches in non-seed region
Number of mismatches in seed region
Number of mismatches in cleavage site region The off-target score was calculated for considering assumption 1 to 3 as follows:

$$\text{Off-target score} = \text{number of seed mismatches} * 10 + \\ \text{number of cleavage site mismatches} * 1.2 + \\ \text{number of non-seed mismatches} * 1$$

The most relevant off-target gene for input each 19mer input sequences was defined as the gene with the lowest off-target score. Accordingly, the lowest off-target score was defined as the relevant off-target score for the corresponding siRNA.

In order to generate a ranking for siRNAs, calculated relevant off-target scores were transferred into a result table. All siRNAs were sorted according to the off-target score (descending).

An off-target score of 2.2 was defined as cut-off for siRNA selection (specificity criterion). In addition, all sequences with only one mismatch in the seed region were eliminated from the screening set. The selection procedure resulted in a set of 93 JCV specific siRNAs (Table 1a).

An expanded screening was generated by re-calculating the predicted specificity based on the newly available human RefSeq database (Human mRNA sequences in RefSeq release version 21 (downloaded Jan. 12, 2007)) and selecting only 208 siRNAs that did not contain more than 3 G's in a row and had an off-target score of at least 2 for the antisense strand (Table 1b).

Synthesis of JCV siRNAs

All siRNAs were synthesized in 0.2 µmole synthesis scale on an ABI3900 DNA synthesizer according to standard procedures.

For the initial screening set (93 different siRNA sequences), 4 different strategies of chemical modification were used:

a) exo/endo light (EEL):
sense strand: 2'-O-methyl @ all pyrimidines, PTO between nucleotides 20 and 21 (counting from 5'-end), dTdT at 3'-end (nucleotides 20 and 21)
antisense strand: 2'-O-methyl at pyrimidines in 5'-UA-3' and 5'-CA-3' motives, PTO between nucleotides 20 and 21 (counting from 5'-end), dTdT at 3'-end (nucleotides 20 and 21)

b) EEL plus 2'-O-methyl in position 2 of antisense strand (only if no 5'-UA-3' and 5'-CA-3' at 5'-end, otherwise already covered by EEL)

c) EEL plus 2'-O-methyl in position 2 of sense strand (only if no pyrimidine in position 2, otherwise already covered by EEL)

d) EEL plus 2'-O-methyl in position 2 of sense and antisense strand (only if not already covered by a, b, and c) (Table 1a)

For the expanded screening set (208 different siRNA sequences), siRNAs were composed of unmodified RNA oligonucleotides with dT/dT overhangs (dTdT at 3'-end (nucleotides 20 and 21) of antisense and sense strands) (Table 1b).

Screening of JCV siRNAs

Construction of Reporter-Systems Encoding JCV Transcripts

The sequence of the early JCV transcript (E) was synthesized at GENEART (Regensburg, Germany) and cloned into GENEART standard vectors. The sequence of the late JCV transcript was subdivided in a first approach into two fragments: L1, including the transcript sequence of the VP1 protein, and LA23, including the sequences of VP2, VP3 and the Agnoprotein. Due to cloning problems with fragment LA23, this sequence was subdivided in a second approach into two fragments (LA23 1-700 and LA23 701-1438). All sequences were synthesized at GENEART and cloned into GENEART standard vectors. All fragments (E, L1, LA23 1-700 and LA23 701-1438) were subcloned into psiCheck-2 (Promega, Mannheim, Germany) via XhoI and NotI (both NEB, Frankfurt, Germany), resulting in constructs with the JCV sequences between the stop-codon and the polyA-signal of Renilla luciferase.

L1
(SEQ ID NO: 931)
CTCGAGACTTTTAGGGTTGTACGGGACTGTAACACCTGCTCTTGAAGCAT

ATGAAGATGGCCCCAACAAAAAGAAAAGGAGAAAGGAAGGACCCCGTGCA

AGTTCCAAAACTTCTTATAAGAGGAGGAGTAGAAGTTCTAGAAGTTAAAA

CTGGGGTTGACTCAATTACAGAGGTAGAATGCTTTTTAACTCCAGAAATG

GGTGACCCAGATGAGCATCTTAGGGGTTTTAGTAAGTCAATTTCTATATC

AGATACATTTGAAAGTGACTCCCCAAATAAGGACATGCTTCCTTGTTACA

GTGTGGCCAGAATTCCACTACCCAATCTAAATGAGGATCTAACCTGTGGA

AATATACTAATGTGGGAGGCTGTGACCTTAAAAACTGAGGTTCTAGGGGT

GACAACTTTGATGAATGTGCACTCTAATGGTCAAGCAACTCATGACAATG

GTGCAGGAAAGCCAGTGCAGGGCACCAGCTTTCATTTTTTTCTGTTGGC

GGGGAGGCTTTAGAATTACAGGGGGTGGTTTTTAATTACAGAACAAAGTA

CCCAGATGGAACAATTTTTCCAAAGAATGCAACAGTGCAATCTCAAGTAA

TGAACACAGAGCACAAGGCGTACCTAGATAAGAACAAAGCATATCCTGTT

GAATGTTGGGTTCCTGATCCCACCAGAAATGAAAACACAAGATATTTTGG

GACACTAACAGGAGGAGAAAATGTTCCTCCAGTTCTTCATATAACAAACA

CTGCCACAACAGTGCTGCTTGATGAATTTGGTGTTGGGCCACTTTGCAAA

GGTGACAACTTGTATTTGTCAGCTGTTGATGTTTGTGGAATGTTTACTAA

CAGATCTGGTTCCCAGCAGTGGAGAGGACTGTCCAGATATTTTAAGGTTC

AGCTCAGAAAAAGGAGGGTTAAAAACCCCTACCCAATTTCTTTCCTTCTT

ACTGATTTGATTAACAGAAGGACCCCTAGAGTTGATGGGCAACCTATGTA

TGGTATGGATGCTCAGGTAGAGGAGGTTAGAGTTTTTGAGGGGACAGAGG

AACTTCCAGGGGACCCAGACATGATGAGATATGTTGACAGATATGGACAG

TTGCAAACAAAGATGCTGTAATCAAAATCCTTTATTGTAATATGCAGTAC

ATTTTAATAAAGTATAACCAGCTTTACTTTACAGTTGCAGTCATGCGGCC

GC

E
(SEQ ID NO: 932)
CTCGAGCCGCCTCCAAGCTTACTCAGAAGTAGTAAGGGCGTGGAGGCTTT

TTAGGAGGCCAGGGAAATTCCCTTGTTTTTCCCTTTTTTGCAGTAATTTT

TTGCTGCAAAAAGCTAAAATGGACAAAGTGCTGAATAGGGAGGAATCCAT

GGAGCTTATGGATTTATTAGGCCTTGATAGGTCTGCATGGGGGAACATTC

CTGTCATGAGAAAAGCTTATCTGAAAAAATGCAAAGAACTCCACCCTGAT

AAAGGTGGGACGAAGACAAGATGAAGAGAATGAATTTTTTATATAAAAA

AATGGAACAAGGTGTAAAAGTTGCTCATCAGCCTGATTTTGGTACATGGA

ATAGTTCAGAGGTTGGTTGTGATTTTCCTCCTAATTCTGATACCCTTTAT

TGCAAGGAATGGCCTAACTGTGCCACTAATCCTTCAGTGCATTGCCCCTG

TTTAATGTGCATGCTAAAATTAAGGCATAGAAACAGAAAATTTTTAAGAA

GCAGCCCACTTGTGTGGATAGATTGCTATTGCTTTGATTGCTTCAGACAA

TGGTTTGGGTGTGACTTAACCCAAGAAGCTCTTCATTGCTGGGAGAAAGT

TCTTGGAGACACCCCCTACAGGGATCTAAAGCTTTAAGTGCCAACCTATG

GAACAGATGAATGGGAATCCTGGTGGAATACATTTAATGAGAAGTGGGAT

-continued

```
GAAGACCTGTTTTGCCATGAAGAAATGTTTGCCAGTGATGATGAAAACAC

AGGATCCCAACACTCTACCCCACCTAAAAAGAAAAAAAAGGTAGAAGACC

CTAAAGACTTTCCTGTAGATCTGCATGCATTCCTCAGTCAAGCTGTGTTT

AGTAATAGAACTGTTGCTTCTTTTGCTGTGTATACCACTAAAGAAAAAGC

TCAAATTTTATATAAGAAACTTATGGAAAAATATTCTGTAACTTTTATAA

GTAGACATGGTTTGGGGGTCATAATATTTTGTTTTTCTTAACACCACAT

AGACATAGAGTGTCAGCAATTAATAACTACTGTCAAAAACTATGTACCTT

TAGTTTTTTAATTTGTAAAGGTGTGAATAAGGAATACTTGTTTTATAGTG

CCCTGTGTAGACAGCCATATGCAGTAGTGGAAGAAAGTATTCAGGGGGGC

CTTAAGGAGCATGACTTTAACCCAGAAGAACCAGAAGAAACTAAGCAGGT

TTCATGGAAATTAGTTACACAGTATGCCTTGGAAACCAAGTGTGAGGATG

TTTTTTTGCTTATGGGCATGTACTTAGACTTTCAGGAAAACCCACAGCAA

TGCAAAAAATGTGAAAAAAAGGATCAGCCAAATCACTTTAACCATCATGA

AAAACACTATTATAATGCCCAAATTTTTGCAGATAGCAAAAATCAAAAAA

GCATTTGCCAGCAGGCTGTTGATACTGTAGCAGCCAAACAAAGGGTTGAC

AGCATCCACATGACCAGAGAAGAAATGTTAGTTGAAAGGTTTAATTTCTT

GCTTGATAAAATGGACTTAATTTTTGGGGCACATGGCAATGCTGTTTTAG

AGCAATATATGGCTGGGGTGGCCTGGATTCATTGCTTGCTGCCTCAAATG

GACACTGTTATTTATGACTTTCTAAAATGCATTGTATTAAACATTCCAAA

AAAAAGGTACTGGCTATTCAAGGGGCCAATAGACAGTGGCAAAACTACTT

TAGCTGCAGCTTTACTTGATCTCTGTGGGGAAAGTCATTAAATGTTAAT

ATGCCATTAGAAAGATTAAACTTTGAATTAGGAGTGGGTATAGATCAGTT

TATGGTTGTATTTGAGGATGTAAAAGGCACTGGTGCAGAGTCAAGGGATT

TACCTTCAGGGCATGGCATAAGCAACCTTGATTGCTTAAGAGATTACTTA

GATGGAAGTGTAAAAGTTAATTTAGAGAGAAAACACCAAAACAAAAGAAC

ACAGGTGTTTCCACCTGGAATTGTAACCATGAATGAATATTCAGTGCCTA

GAACTTTACAGGCCAGATTTGTAAGGCAGATAGATTTTAGACCAAAGGCC

TACCTGAGAAAATCACTAAGCTGCTCTGAGTATTTGCTAGAAAAAAGGAT

TTTGCAAAGTGGTATGACTTTGCTTTTGCTTTTAATCTGGTTTAGGCCAG

GTTGCTGACTTTGCAGCTGCCATTCATGAGAGGATTGTGCAGTGGAAAGA

AAGGCTGGATTTAGAAATAAGCATGTATACATTTTCTACTATGAAAGCTA

ATGTTGGTATGGGGAGACCCATTCTTGACTTTCCTAGAGAGGAAGATTCT

GAAGCAGAAGACTCTGGACATGGATCAAGCACGTAATCACAATCACAATG

CTTTTCCCAGGTCTCAGAAGCCTCTGGTGCAGACACACAGGAAAACTGCA

CTTTTCACATCTGTAAAGGCTTTCAATGTTTCAAAAAACCAAAGACCCCT

CCCCCAAAATAACTGCAACTGTGCGGCCGC

LA23 1-700
                                        (SEQ ID NO: 933)
CTCGAGCAGCTAACAGCCAGTAAACAAAGCACAAGGGGAAGTTGAAAGCA

GCCAAGGGAACATGTTTTGCGAGCCAGAGCTGTTTTGGCTTGTCACCAGC

TGGCCATGGTTCTTCGCCAGCTGTCACGTAAGGCTTCTGTGAAAGTTAGT
```

```
AAAACCTGGAGTGGAACTAAAAAAAGAGCTCAAAGGATTTTAATTTTTTT

GTTAGAATTTTTGCTGGACTTTTGCACAGGTGAAGACAGTGTAGACGGGA

AAAAAAGACAGAGACACAGTGGTTTGACTGAGCAGACATACAGTGCTTTG

CCTGAACCAAAAGCTACATAGGTAAGTAATGTTTTTTTTTGTGTTTTCAG

GTTCATGGGTGCCGCACTTGCACTTTTGGGGGACCTAGTTGCTACTGTTT

CTGAGGCTGCTGCTGCCACAGGATTTTCAGTAGCTGAAATTGCTGCTGGA

GAGGCTGCTGCTACTATAGAAGTTGAAATTGCATCCCTTGCTACTGTAGA

GGGGATTACAAGTACCTCTGAGGCTATAGCTGCTATAGGCCTTACTCCTG

AAACATATGCTGTAATAACTGGAGCTCCGGGGGCTGTAGCTGGGTTTGCT

GCATTGGTTCAAACTGTAACTGGTGGTAGTGCTATTGCTCAGTTGGGATA

TAGATTTTTTGCTGACTGGGATCATAAAGTTTCAACAGTTGGGCTTTTTC

GCGGCCGC
```

LA23 701-1438
                                        (SEQ ID NO: 934)
```
CTCGAGAGCAGCCAGCTATGGCTTTACAATTATTTAATCCAGAAGACTAC

TATGATATTTTATTTCCTGGAGTGAATGCCTTTGTTAACAATATTCACTA

TTTAGATCCTAGACATTGGGGCCCGTCCTTGTTCTCCACAATCTCCCAGG

CTTTTTGGAATCTTGTTAGAGATGATTTGCCAGCCTTAACCTCTCAGGAA

ATTCAGAGAAGAACCCAAAAACTATTTGTTGAAAGTTTAGCAAGGTTTTT

GGAAGAAACTACTTGGGCAATAGTTAATTCACCAGCTAACTTATATAATT

ATATTTCAGACTATTATTCTAGATTGTCTCCAGTTAGGCCCTCTATGGTA

AGGCAAGTTGCCCAAAGGGAGGGAACCTATATTTCTTTTGGCCACTCATA

CACCCAAAGTATAGATGATGCAGACAGCATTCAAGAAGTTACCCAAAGGC

TAGATTTAAAAACCCCAAATGTGCAATCTGGTGAATTTATAGAAAGAAGT

ATTGCACCAGGAGGTGCAAATCAAAGATCTGCTCCTCAATGGATGTTGCC

TTTACTTTTAGGGTTGTACGGGACTGTAACACCTGCTCTTGAAGCATATG

AAGATGCCCCAACAAAAAGAAAAGGAGAAAGGAAGGACCCCGTGCAAGT

TCCAAAACTTCTTATAAGAGGAGGAGTAGAAGTTCTAGAAGTTAAAACTG

GGGTTGACTCAATTACAGAGGTAGAATGCTGCGGCCGC
```

Screen of JCV siRNAs in Transfected Cells

Cos-7 cells (DSMZ, Braunschweig, Germany, #ACC-60) were seeded at $1.5 \times 10^4$ cells/well on white 96-well plates with clear bottoms (Greiner Bio-One GmbH, Frickenhausen, Germany) in 75 µl of growth medium. Directly after seeding the cells, 50 ng of the corresponding reporter-plasmid per well was transfected with Lipofectamine™ 2000 (Invitrogen GmbH, Karlsruhe, Germany), with the plasmid diluted in Opti-MEM to a final volume of 12.5 µl per well, prepared as a mastermix for the whole plate.

4 h after plasmid transfection, growth medium was removed from cells and replaced by 100 µl/well of fresh medium. siRNA transfections were performed using Lipofectamine™ 2000 (Invitrogen GmbH, Karlsruhe, Germany) as described by the manufacturer. Cells were incubated for 24 h at 37° C. and 5% $CO_2$ in a humidified incubator (Heraeus GmbH, Hanau, Germany). For the primary screen, all siRNAs were screened at a final concentration of 30 nM. Selected sequences were rescreened at a siRNA concentration of 300 pM. Each siRNA was tested in quadruplicate for each concentration.

Cells were lysed by removing growth medium and application of 150 μl of a 1:1 mixture consisting of medium and substrate from the Dual-Glo Luciferase Assay System (Promega, Mannheim, Germany). The luciferase assay was performed according to the manufacturer's protocol for Dual-Glo Luciferase assay and luminescence was measured in a Victor-Light 1420 Luminescence Counter (Perkin Elmer, Rodgau-Jügesheim, Germany). Values obtained with Renilla luciferase were normalized to the respective values obtained with Firefly luciferase in order to correct for transfection efficacy. Renilla/Firefly luciferase activities obtained after transfection with siRNAs directed against a JCV gene were normalized to Renilla/Firefly luciferase activities obtained after transfection of an unrelated control siRNA set to 100%. Tables 1a and b provides the results where the siRNAs, the sequences of which are given in Tables 1a and b, were tested at a single dose of 30 nM. The percentage inhibition±standard deviation, compared to the unrelated control siRNA, is indicated in the column 'Remaining luciferase activity (% of control)'. A number of JCV siRNAs at 30 nM were effective at reducing levels of the targeted mRNA by more than 70% in Cos-7 cells (i.e. remaining luciferase activity was less than 30%).

Selected JCV siRNAs from the single dose screen were further characterized by dose response curves. Transfections of JCV siRNAs for generation of dose response curves were performed with the following siRNA concentrations according to the above protocol:

from 33 nM in 3-fold dilutions down to 0.005 nM (for fragment L1)

from 24 nM in 4-fold dilutions down to 0.001 nM (for fragment E and fragments LA23 1-700 and LA23 701-1438).

IC50 values were determined by parameterized curve fitting using the program XLfit (IDBS, Guildford, Great Britain). Table 2 provides the results from two independent experiments for 32 selected JCV siRNAs. The mean 1050 from these two independent experiments is shown. Several JCV siRNAs (AD-12622, AD-12677, AD-12709, AD-12710, AD-12722, AD-12724, AD-12728, AD-12763, AD-12767, AD-12768, AD-12769, AD-12771, AD-12774, AD-12775, AD-12777, AD-12781, AD-12784, AD-12795, AD-12813, AD-12821, AD-12823, AD-12824, AD-12825, AD-12827, AD-12829, AD-12842) were particularly potent in this experimental paradigm, and exhibited 1050 values between 70 pM and 1 nM.

TABLE 2

IC50s

| Duplex name | Mean IC50 [nM] |
|---|---|
| AD-12599 | 2.37 |
| AD-12622 | 0.57 |
| AD-12666 | 3.7 |
| AD-12677 | 0.49 |
| AD-12709 | 0.19 |
| AD-12710 | 0.47 |
| AD-12712 | 2.33 |
| AD-12722 | 0.12 |
| AD-12724 | 0.26 |
| AD-12728 | 0.8 |
| AD-12761 | 1.2 |
| AD-12763 | 0.95 |
| AD-12767 | 0.09 |
| AD-12768 | 0.19 |
| AD-12769 | 0.35 |
| AD-12771 | 0.35 |
| AD-12774 | 0.13 |

TABLE 2-continued

IC50s

| Duplex name | Mean IC50 [nM] |
|---|---|
| AD-12775 | 0.18 |
| AD-12777 | 0.17 |
| AD-12778 | 12.65 |
| AD-12781 | 0.18 |
| AD-12784 | 0.44 |
| AD-12795 | 0.65 |
| AD-12813 | 0.2 |
| AD-12818 | 1.88 |
| AD-12821 | 0.07 |
| AD-12823 | 0.46 |
| AD-12824 | 0.25 |
| AD-12825 | 0.52 |
| AD-12827 | 0.15 |
| AD-12829 | 0.14 |
| AD-12842 | 0.44 |

Screen of JCV siRNAs Against Live JC Virus in SVG-A Cells

Cells and Virus

SVG-A cells (human fetal glial cells transformed by SV40 T antigen) obtained from Walter Atwood at Brown University were cultured in Eagle's Minimum Essential Media (ATCC, Manassas, Va.) supplemented to contain 10% fetal bovine serum (FBS) (Omega Scientific, Tarzana, Calif.), Penicillin 100 U/ml, Streptomycin 100 ug/ml (Invitrogen, Carlsbad Calif.) at 37° C. in an atmosphere with 5% $CO_2$ in a humidified incubator (Heraeus HERAcell, Thermo Electron Corporation, Ashville, N.C.). The Mad-1-SVEΔ strain of JCV obtained from Walter Atwood at Brown University was used in all experiments; viral stocks were prepared using SVG-A cells according to standard published methods (Liu and Atwood, Propagation and assay of the JC Virus, Methods Mol Biol. 2001; 165:9-17).

Prophylaxis Assay

SVG-A cells were seeded on glass coverslips in 6-well dishes 24 hours prior to transfection in the media described above minus antibiotics. Cells were transfected with the indicated concentration of siRNA (10 nM, 50 nM, or 100 nM) using Lipofectamine™ 2000 according to the manufacturer's instructions (Invitrogen, Carlsbad, Calif.). Twenty-four hours post-transfection cells were washed with media containing 2% FBS and then infected with a 1:25 dilution of JCV virus stock (Mad-1-SVEΔ strain) diluted in 2% FBS media. Cells were rocked every 15 minutes by hand several times to get equal virus binding across the entire coverslip for one hour and then additional 10% FBS media was added and the infection was allowed to proceed for 72 hours. Seventy two hours post-infection, cells were fixed in acetone and stained for late viral protein (VP1) by standard immunofluoresence methods using hybridoma supernatant PAB597 recognizing JCV VP1 (obtained from Walter Atwood at Brown University) with goat anti-mouse Alexa Fluor 488 secondary antibody (Invitrogen, Carlsbad, Calif.). Infected cells were scored by counting VP1-immunoreactive cells using a fluorescence microscope (Zeiss, Imager.Z1, Thornwood, N.J.) and data were expressed as the percentage of infected cells counted for the control coverslips transfected with Luciferase siRNA. Table 3 shows the results of the prophylaxis assays at different siRNA concentrations (10 nM, 50 nM or 100 nM). The VP1 siRNAs were the most potent as a group, followed by the T antigen siRNAs, with the VP2/3 siRNAs being the least potent. The VP1 siRNAs most effective in reducing virus were consistently AD-12622, AD-12728, AD-12795, and AD-12842. The most potent T antigen siRNA was AD-12813.

TABLE 3

Prophylaxis Assay

| Duplex Number | Targeted JCV Transcript | Remaining Virus (% of Luciferase Control) | | |
|---|---|---|---|---|
| | | 50 nM | 10 nM | 100 nM |
| AD-12599 | VP1 | 79.9 | ND | ND |
| AD-12709 | VP1 | 46.0 | ND | ND |
| AD-12710 | VP1 | 25.9 | ND | ND |
| AD-12784 | VP1 | 30.9 | ND | ND |
| AD-12712 | VP1 | 29.7 | ND | ND |
| AD-12724 | VP1 | 30.5 | 38.9 | 25.8 |
| AD-12622 | VP1 | 22.9 | 28.2 | 9.1 |
| AD-12728 | VP1 | 21.1 | 22.2 | ND |
| AD-12795 | VP1 | 13.6 | 16.9 | 8.5 |
| AD-12842 | VP1 | 16.0 | 23.4 | 12.7 |
| AD-12761 | VP1 | 26.4 | 52.3 | ND |
| AD-12818 | VP1 | 24.0 | 50.2 | 28.0 |
| AD-12666 | VP1 | 54.1 | ND | ND |
| AD-12763 | VP1 | 39.5 | ND | ND |
| AD-12722 | T Antigen | 43.6 | 82.1 | ND |
| AD-12813 | T Antigen | 21.5 | 48.8 | 19.4 |
| AD-12767 | T Antigen | 37.6 | 52.2 | 30.9 |
| AD-12821 | T Antigen | 33.0 | 51.2 | 30.8 |
| AD-12774 | T Antigen | 74.0 | 89.2 | ND |
| AD-12827 | T Antigen | 77.0 | 92.0 | ND |
| AD-12775 | T Antigen | 81.6 | 95.4 | ND |
| AD-12777 | T Antigen | 73.3 | 93.9 | ND |
| AD-12829 | T Antigen | 78.6 | 93.6 | ND |
| AD-12781 | T Antigen | 38.8 | 62.6 | 34.4 |
| AD-12768 | VP2/3 | 73.9 | 92.4 | ND |
| AD-12771 | VP2/3 | 51.6 | 83.6 | ND |
| AD-12824 | VP2/3 | 42.1 | 79.0 | 43.7 |
| AD-12769 | VP2/3 | 35.2 | 78.0 | 39.7 |
| AD-12823 | VP2/3 | 38.1 | 78.1 | 42.0 |
| AD-12677 | VP2/3 | 99.1 | 102.1 | ND |
| AD-12825 | VP2/3 | 100.8 | 99.1 | ND |

ND indicates no data.

Post-Infection Treatment Assay

SVG-A cells were seeded on glass coverslips in 6-well dishes 24 hours prior to infection in 10% FBS media. Cells were washed with media containing 2% FBS and then infected with a 1:25 dilution of JCV virus stock diluted in 2% FBS media. Cells were rocked by hand approximately 8-10 times to get equal virus binding across the entire coverslip every 15 minutes for one hour and then additional 10% FBS media was added. Twenty-four and forty-eight hours postinfection, cells were washed with 10% FBS media containing no antibiotics and then transfected with 50 nM of the indicated siRNA using Lipofectamine™ 2000 according to the manufacturer's instructions (Invitrogen, Carlsbad, Calif.). Seventy-two hours postinfection, cells were fixed in acetone and stained for late viral protein (VP1) by standard immunofluoresence methods using hybridoma supernatant PAB597 recognizing JCV VP1 (obtained from Walter Atwood at Brown University) with goat anti-mouse Alexa Fluor 488 secondary antibody (Molecular Probes, Eugene, Oreg.). Infected cells were scored by counting VP1-immunoreactive cells using a fluorescence microscope (Zeiss, Imager.Z1, Thornwood, N.J.) and data were expressed as the percentage of infected cells counted for control coverslips transfected with Luciferase siRNA. Table 4 shows the results of the post-infection treatment experiments. All of the siRNAs tested in the treatment assay showed significant antiviral activity against JCV, such that the remaining virus was significantly less than that in the luciferase siRNA control.

TABLE 4

Treatment Assay

| Duplex Number | Targeted JCV Transcript | Remaining Virus (% of Luciferase Control) |
|---|---|---|
| AD-12724 | VP1 | 38.9 |
| AD-12622 | VP1 | 28.2 |
| AD-12795 | VP1 | 16.9 |
| AD-12842 | VP1 | 23.4 |
| AD-12818 | VP1 | ND |
| AD-12813 | T Antigen | 48 |
| AD-12767 | T Antigen | 56.9 |
| AD-12821 | T Antigen | 75.8 |
| AD-12781 | T Antigen | 75.8 |
| AD-12824 | VP2/3 | 60.4 |
| AD-12769 | VP2/3 | 70.7 |
| AD-12823 | VP2/3 | 72.4 |

ND indicates no data.

Prophylaxis Administration of JCV siRNAs Inhibits the Production of Active Progeny JC Virus SVG-A cells were seeded in 6-well dishes 24 hours prior to transfection in the media described above minus antibiotics. Cells were transfected with 10 nM of the indicated siRNA using Lipofectamine™ 2000 according to the manufacturer's instructions (Invitrogen, Carlsbad, Calif.). Twenty-four hours post-transfection cells were washed with media containing 2% FBS and then infected with a 1:25 dilution of JCV virus stock (Mad-1-SVEΔ strain) diluted in 2% FBS media. Cells were rocked every 15 minutes by hand several times to get equal virus binding across the entire coverslip for one hour and then additional 10% FBS media was added and the infection was allowed to proceed for 6 days. Six days post-infection, progeny virus was collected either by removal of overlay media from infected cells or by scraping cells and performing virus preparations. The virus preparations consisted of scraping cells into the supernatant media, vortexing, freeze-thawing the re-suspended cells 2 times with vortexing in between, then spinning down the cell debris and taking the supernatant. Fresh SVG-A cells seeded on glass coverslips were infected secondarily with virus collected by either method using the same procedure done with the initial infection to determine the amount of infectious virus produced by cells transfected with the various siRNAs. At 72 hours post-infection of coverslips, cells were fixed in acetone and stained for late viral protein (VP1) by standard immunofluoresence methods using hybridoma supernatant PAB597 recognizing JCV VP1 (obtained from Walter Atwood at Brown University) with goat anti-mouse Alexa Fluor 488 secondary antibody (Invitrogen, Carlsbad, Calif.). Infected cells were scored by counting VP1-immunoreactive cells using a fluorescence microscope (Zeiss, Imager.Z1, Thornwood, N.J.) and data were expressed as the percentage of infected cells counted for the control coverslips transfected with Luciferase siRNA. Table 5 shows the results for selected siRNAs, demonstrating the ability of prophylaxis siRNA treatment to inhibit active progeny virus production by either method of virus collection. Transfection with siRNAs targeting VP1 (AD-12622 and AD-12842) had the greatest effect on inhibiting the production of active progeny virus regardless of whether virus was collected from media or from infected cell preparations. The T antigen siRNA AD-12813 had the next strongest inhibitory effect, whereas the VP2/3 siRNAs AD-12824 and AD-12769 still showed some albeit a lesser ability to inhibit active progeny JCV production.

TABLE 5

Prophylaxis administration of JCV siRNAs inhibits the production of active progeny JC virus capable of secondary infection

| Duplex Name | Targeted Transcript | Remaining Virus (% of Luciferase Control) | |
|---|---|---|---|
| | | Media | Virus Preparation |
| AD-12622 | VP1 | 30.8 | 24.9 |
| AD-12842 | VP1 | 33.3 | 26.9 |
| AD-12813 | T Antigen | 57.8 | 38.7 |
| AD-12824 | VP2/3 | 83.6 | 57.6 |
| AD-12769 | VP2/3 | 79.1 | 52.2 |

Stability in Cerebrospinal Fluid (CSF) of Selected siRNAs Targeting JCV

Eleven selected JCV siRNAs were tested for stability at 5 uM over 48 h at 37° C. in human CSF, as well as in PBS for comparison. 30 μl of human cerebrospinal fluid (CSF) was mixed with 3 μl of 50 μM duplex (siRNA) solution (150 pmole/well) in a 96-well plate, sealed to avoid evaporation and incubated for the indicated time at 37° C. Incubation of the siRNA in 30 ul PBS for 48 h served as a control for non-specific degradation. Reactions were stopped by the addition of 4 ul proteinase K (20 mg/ml) and 25 ul of proteinase K buffer, and an incubation for 20' at 42° C. Samples were then spin filtered through a 0.2 μm 96 well filter plate at 3000 rpm for 20'. Incubation wells were washed with 50 ul Millipore water twice and the combined washing solutions were spin filtered also.

Samples were analyzed by ion exchange HPLC under denaturing conditions. Samples were transferred to single autosampler vials. IEX-HPLC analysis was performed under the following conditions: Dionex DNAPac PA200 (4×250 mm analytical column), temperature of 45° C. (denaturing conditions by pH=11), flow rate of 1 ml/min, injection volume of 50 ul, and detection wavelength of 260 nm with 1 nm bandwidth (reference wavelength 600 nm). In addition, the gradient conditions were as follows with HPLC Eluent A: 20 mM $Na_3PO_4$ in 10% ACN; pH=11 and HPLC Eluent B: 1 M NaBr in HPLC Eluent A:

| Time | % A | % B |
|---|---|---|
| 0.00 min | 75 | 25 |
| 1.00 min | 75 | 25 |
| 19.0 min | 38 | 62 |
| 19.5 min | 0 | 100 |
| 21.5 min | 0 | 100 |
| 22.0 min | 75 | 25 |
| 24.0 min | 75 | 25 |

Under the above denaturing IEX-HPLC conditions, the duplexes eluted as two separated single strands. All chromatograms were integrated automatically by the Dionex Chromeleon 6.60 HPLC software, and were adjusted manually as necessary. The area under the peak for each strand was calculated and the %-values for each intact full length product (FLP) for each time points were calculated by the following equation:

$$\%\text{-FLP}_{(s/as;\ t=x)}=(\text{PeakArea}_{(s/as);\ t=x}/\text{Peak Area}_{(s/as);\ t=0\ min})*100\%$$

All values were normalized to FLP at t=0 min. Table 6 provides the results after 48 hours of incubation in human CSF at 37° C. At least 75% of both antisense and sense strands of ten JCV siRNAs (AD-12622, AD-12724, AD-12767, AD-12769, AD-12795, AD-12813, AD-12818, AD-12823, AD-12824, AD-12842) were recovered, demonstrating that these siRNAs are highly stable in human CSF at 37° C. For AD-12821, 59% of the antisense and 97% of the sense strand was recovered after 48 h of incubation in human CSF at 37° C., showing that this siRNA has a half-life of greater than 48 h in human CSF at 37° C.

TABLE 6

| Stability in human CSF | | |
|---|---|---|
| Duplex | % full length material after 48 hours | |
| name | antisense | sense |
| AD-12622 | 93 | 105 |
| AD-12724 | 90 | 106 |
| AD-12767 | 85 | 104 |
| AD-12769 | 100 | 104 |
| AD-12795 | 86 | 109 |
| AD-12813 | 94 | 98 |
| AD-12818 | 75 | 99 |
| AD-12821 | 59 | 97 |
| AD-12823 | 98 | 98 |
| AD-12824 | 84 | 98 |
| AD-12842 | 87 | 102 | dsRNA Expression Vectors

In another aspect of the invention, JC virus specific dsRNA molecules that modulate JC virus genome expression activity are expressed from transcription units inserted into DNA or RNA vectors (see, e.g., Couture, A, et al., *TIG*. (1996), 12:5-10; Skillern, A., et al., International PCT Publication No. WO 00/22113, Conrad, International PCT Publication No. WO 00/22114, and Conrad, U.S. Pat. No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann, et al., *Proc. Natl. Acad. Sci. USA* (1995) 92:1292).

The individual strands of a dsRNA can be transcribed by promoters on two separate expression vectors and co-transfected into a target cell. Alternatively each individual strand of the dsRNA can be transcribed by promoters both of which are located on the same expression plasmid. In a preferred embodiment, a dsRNA is expressed as an inverted repeat joined by a linker polynucleotide sequence such that the dsRNA has a stem and loop structure.

The recombinant dsRNA expression vectors are generally DNA plasmids or viral vectors. dsRNA expressing viral vectors can be constructed based on, but not limited to, adeno-associated virus (for a review, see Muzyczka, et al., *Curr. Topics Micro. Immunol*. (1992) 158:97-129)); adenovirus (see, for example, Berkner, et al., BioTechniques (1998) 6:616), Rosenfeld et al. (1991, Science 252:431-434), and Rosenfeld et al. (1992), Cell 68:143-155)); or alphavirus as well as others known in the art. Retroviruses have been used to introduce a variety of genes into many different cell types, including epithelial cells, in vitro and/or in vivo (see, e.g., Eglitis, et al., *Science* (1985) 230:1395-1398; Danos and Mulligan, *Proc. Natl. Acad. Sci. USA* (1998) 85:6460-6464; Wilson et al., 1988, Proc. Natl. Acad. Sci. USA 85:3014-3018; Armentano et al., 1990, Proc. Natl. Acad. Sci. USA 87:6141-6145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Natl. Acad. Sci.

USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

The promoter driving dsRNA expression in either a DNA plasmid or viral vector of the invention may be a eukaryotic RNA polymerase I (e.g. ribosomal RNA promoter), RNA polymerase II (e.g. CMV early promoter or actin promoter or U1 snRNA promoter) or generally RNA polymerase III promoter (e.g. U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g. the insulin regulatory sequence for pancreas (Bucchini et al., 1986, Proc. Natl. Acad. Sci. USA 83:2511-2515)).

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D1-thiogalactopyranoside (EPTG). A person skilled in the art would be able to choose the appropriate regulatory/promoter sequence based on the intended use of the dsRNA transgene.

Generally, recombinant vectors capable of expressing dsRNA molecules are delivered as described below, and persist in target cells. Alternatively, viral vectors can be used that provide for transient expression of dsRNA molecules. Such vectors can be repeatedly administered as necessary. Once expressed, the dsRNAs bind to target RNA and modulate its function or expression. Delivery of dsRNA expressing vectors can be systemic, such as by intravenous or intramuscular administration, by administration to target cells ex-planted from the patient followed by reintroduction into the patient, or by any other means that allows for introduction into a desired target cell.

dsRNA expression DNA plasmids are typically transfected into target cells as a complex with cationic lipid carriers (e.g. Oligofectamine) or non-cationic lipid-based carriers (e.g. Transit-TKO™). Multiple lipid transfections for dsRNA-mediated knockdowns targeting different regions of a single JC virus genome or multiple JC virus genomes over a period of a week or more are also contemplated by the invention. Successful introduction of the vectors of the invention into host cells can be monitored using various known methods. For example, transient transfection can be signaled with a reporter, such as a fluorescent marker, such as Green Fluorescent Protein (GFP). Stable transfection of ex vivo cells can be ensured using markers that provide the transfected cell with resistance to specific environmental factors (e.g., antibiotics and drugs), such as hygromycin B resistance.

The JC virus specific dsRNA molecules can also be inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Tables 1a-1 and 1a-2

TABLE 1a

JCV Gene Walk; siRNAs targeting >95% of all stransins (> = out of 388); Human specific pan-JCV: 208 siRNAs; all siRNAs double overhang design; dTdT, no modifications. 1 a-1: sequences; 1 a-2: assay results

| Table 1a-1 duplex name | position in consensus | SEQ ID NO: | sense strand sequence (5'-3') | SEQ ID NO: | antisense strand sequence (5'-3') |
|---|---|---|---|---|---|
| AD-14742 | 1533-1551 | 515 | CUUAUAAGAGGAGGAGUAGTT | 516 | CUACUCCUCCUCUUAUAAGTT |
| AD-14743 | 1703-1721 | 517 | CAUGCUUCCUUGUUACAGUTT | 518 | ACUGUAACAAGGAAGCAUGTT |
| AD-14744 | 1439-1457 | 519 | UACGGGACUGUAACACCUGTT | 520 | CAGGUGUUACAGUCCCGUATT |
| AD-14745 | 1705-1723 | 521 | UGCUUCCUUGUUACAGUGUTT | 522 | ACACUGUAACAAGGAAGCATT |
| AD-14746 | 2064-2082 | 523 | CCUGUUGAAUGUUGGGUUCTT | 524 | GAACCCAACAUUCAACAGGTT |
| AD-14747 | 2067-2085 | 525 | GUUGAAUGUUGGGUUCCUGTT | 526 | CAGGAACCCAACAUUCAACTT |
| AD-14748 | 2071-2089 | 527 | AAUGUUGGGUUCCUGAUCCTT | 528 | GGAUCAGGAACCCAACAUUTT |
| AD-14749 | 2121-2139 | 529 | ACACUAACAGGAGGAGAAATT | 530 | UUUCUCCUCCUGUUAGUGUTT |
| AD-14750 | 1535-1553 | 531 | UAUAAGAGGAGGAGUAGAATT | 532 | UUCUACUCCUCCUCUUAUATT |

TABLE 1a-continued

JCV Gene Walk; siRNAs targeting >95% of all stransins
(> = out of 388); Human specific pan-JCV: 208 siRNAs;
all siRNAs double overhang design; dTdT, no
modifications. 1 a-1: sequences; 1 a-2: assay results

| Table 1a-1 duplex name | position in consensus | SEQ ID NO: sense strand sequence (5'-3') | SEQ ID NO: antisense strand sequence (5'-3') |
|---|---|---|---|
| AD-14751 | 1536-1554 | 533 AUAAGAGGAGGAGUAGAAGUU | 534 CUUCUACUCCUCCUCUUAUTT |
| AD-14752 | 1445-1463 | 535 ACUGUAACACCUGCUCUUGTT | 536 CAAGAGCAGGUGUUACAGUTT |
| AD-14753 | 1700-1718 | 537 GGACAUGCUUCCUUGUUACTT | 538 GUAACAAGGAAGCAUGUCCTT |
| AD-14754 | 1702-1720 | 539 ACAUGCUUCCUUGUUACAGTT | 540 CUGUAACAAGGAAGCAUGUTT |
| AD-14755 | 1704-1722 | 541 AUGCUUCCUUGUUACAGUGTT | 542 CACUGUAACAAGGAAGCAUTT |
| AD-14756 | 2065-2083 | 543 CUGUUGAAUGUUGGGUUCCTT | 544 GGAACCCAACAUUCAACAGTT |
| AD-14757 | 2070-2088 | 545 GAAUGUUGGGUUCCUGAUCTT | 546 GAUCAGGAACCCAACAUUCTT |
| AD-14758 | 1441-1459 | 547 CGGGACUGUAACACCUGCUTT | 548 AGCAGGUGUUACAGUCCCGTT |
| AD-14759 | 1443-1461 | 549 GGACUGUAACACCUGCUCUTT | 550 AGAGCAGGUGUUACAGUCCTT |
| AD-14760 | 1444-1462 | 551 GACUGUAACACCUGCUCUUTT | 552 AAGAGCAGGUGUUACAGUCTT |
| AD-14761 | 1609-1627 | 553 CUCCAGAAAUGGGUGACCCTT | 554 GGGUCACCCAUUUCUGGAGTT |
| AD-14762 | 1537-1555 | 555 UAAGAGGAGGAGUAGAAGUUT | 556 ACUUCUACUCCUCCUCUUATT |
| AD-14763 | 629-647 | 557 GAGGCUGCUGCUACUAUAGTT | 558 CUAUAGUAGCAGCAGCCUCTT |
| AD-14764 | 656-674 | 559 AUUGCAUCCCUUGCUACUGTT | 560 CAGUAGCAAGGGAUGCAAUTT |
| AD-14765 | 658-676 | 561 UGCAUCCCUUGCUACUGUATT | 562 UACAGUAGCAAGGGAUGCATT |
| AD-14766 | 517-535 | 563 UUGUGUUUUCAGGUUCAUGTT | 564 CAUGAACCUGAAAACACAATT |
| AD-14767 | 559-577 | 565 GGACCUAGUUGCUACUGUUTT | 566 AACAGUAGCAACUAGGUCCTT |
| AD-14768 | 591-609 | 567 CUGCCACAGGAUUUUCAGTT | 568 ACUGAAAAUCCUGUGGCAGTT |
| AD-14769 | 638-656 | 569 GCUACUAUAGAAGUUGAAATT | 570 UUUCAACUUCUAUAGUAGCTT |
| AD-14770 | 655-673 | 571 AAUUGCAUCCCUUGCUACUTT | 572 AGUAGCAAGGGAUGCAAUUTT |
| AD-14771 | 561-579 | 573 ACCUAGUUGCUACUGUUUCTT | 574 GAAACAGUAGCAACUAGGUTT |
| AD-14772 | 639-657 | 575 CUACUAUAGAAGUUGAAAUTT | 576 AUUUCAACUUCUAUAGUAGTT |
| AD-14773 | 715-733 | 577 AGGCCUUACUCCUGAAACATT | 578 UGUUUCAGGAGUAAGGCCUTT |
| AD-14774 | 716-734 | 579 GGCCUUACUCCUGAAACAUTT | 580 AUGUUUCAGGAGUAAGGCCTT |
| AD-14775 | 326-344 | 581 GUAAAACCUGGAGUGGAACTT | 582 GUUCCACUCCAGGUUUUACTT |
| AD-14776 | 518-536 | 583 UGUGUUUUCAGGUUCAUGGTT | 584 CCAUGAACCUGAAAACACATT |
| AD-14777 | 520-538 | 585 UGUUUUCAGGUUCAUGGGUTT | 586 ACCCAUGAACCUGAAAACATT |
| AD-14778 | 661-679 | 587 AUCCCUUGCUACUGUAGAGTT | 588 CUCUACAGUAGCAAGGGAUTT |
| AD-14779 | 560-578 | 589 GACCUAGUUGCUACUGUUUTT | 590 AAACAGUAGCAACUAGGUCTT |
| AD-14780 | 681-699 | 591 GGAUUACAAGUACCUCUGATT | 592 UCAGAGGUACUUGUAAUCCTT |
| AD-14781 | 714-732 | 593 UAGGCCUUACUCCUGAAACTT | 594 GUUUCAGGAGUAAGGCCUATT |
| AD-14782 | 377-395 | 595 UGUUAGAAUUUUUGCUGGATT | 596 UCCAGCAAAAAUUCUAACATT |
| AD-14783 | 589-607 | 597 UGCUGCCACAGGAUUUUCATT | 598 UGAAAAUCCUGUGGCAGCATT |
| AD-14784 | 594-612 | 599 CCACAGGAUUUUCAGUAGCTT | 600 GCUACUGAAAAUCCUGUGGTT |
| AD-14785 | 648-666 | 601 AAGUUGAAAUUGCAUCCCUTT | 602 AGGGAUGCAAUUUCAACUUTT |
| AD-14786 | 649-667 | 603 AGUUGAAAUUGCAUCCCUUTT | 604 AAGGGAUGCAAUUUCAACUTT |

TABLE 1a-continued

JCV Gene Walk; siRNAs targeting >95% of all stransins
(> = out of 388); Human specific pan-JCV: 208 siRNAs;
all siRNAs double overhang design; dTdT, no
modifications. 1 a-1: sequences; 1 a-2: assay results

| Table 1a-1 duplex name | position in consensus | SEQ ID NO: sense strand sequence (5'-3') | SEQ ID NO: antisense strand sequence (5'-3') |
|---|---|---|---|
| AD-14787 | 587-605 | 605 GCUGCUGCCACAGGAUUUUTT | 606 AAAAUCCUGUGGCAGCAGCTT |
| AD-14788 | 325-343 | 607 AGUAAAACCUGGAGUGGAATT | 608 UUCCACUCCAGGUUUUACUTT |
| AD-14789 | 515-533 | 609 UUUUGUGUUUUCAGGUUCATT | 610 UGAACCUGAAAACACAAATT |
| AD-14790 | 516-534 | 611 UUUGUGUUUUCAGGUUCAUTT | 612 AUGAACCUGAAAACACAAATT |
| AD-14791 | 519-537 | 613 GUGUUUUCAGGUUCAUGGGTT | 614 CCCAUGAACCUGAAAACACTT |
| AD-14792 | 521-539 | 615 GUUUUCAGGUUCAUGGGUGTT | 616 CACCCAUGAACCUGAAAACTT |
| AD-14793 | 522-540 | 617 UUUUCAGGUUCAUGGGUGCTT | 618 GCACCCAUGAACCUGAAAATT |
| AD-14794 | 523-541 | 619 UUUCAGGUUCAUGGGUGCCTT | 620 GGCACCCAUGAACCUGAAATT |
| AD-14795 | 616-634 | 621 AAUUGCUGCUGGAGAGGCUTT | 622 AGCCUCUCCAGCAGCAAUUTT |
| AD-14796 | 657-675 | 623 UUGCAUCCCUUGCUACUGUTT | 624 ACAGUAGCAAGGGAUGCAATT |
| AD-14797 | 761-779 | 625 GCUGUAGCUGGGUUUGCUGTT | 626 CAGCAAACCCAGCUACAGCTT |
| AD-14798 | 645-663 | 627 UAGAAGUUGAAAUUGCAUCTT | 628 GAUGCAAUUUCAACUUCUATT |
| AD-14799 | 647-665 | 629 GAAGUUGAAAUUGCAUCCCTT | 630 GGGAUGCAAUUUCAACUUCTT |
| AD-14800 | 660-678 | 631 CAUCCCUUGCUACUGUAGATT | 632 UCUACAGUAGCAAGGGAUGTT |
| AD-14801 | 324-342 | 633 UAGUAAAACCUGGAGUGGATT | 634 UCCACUCCAGGUUUUACUATT |
| AD-14802 | 372-390 | 635 UUUUUUGUUAGAAUUUUUGTT | 636 CAAAAAUUCUAACAAAAAATT |
| AD-14803 | 640-658 | 637 UACUAUAGAAGUUGAAAUUTT | 638 AAUUUCAACUUCUAUAGUATT |
| AD-14804 | 562-580 | 639 CCUAGUUGCUACUGUUUCUTT | 640 AGAAACAGUAGCAACUAGGTT |
| AD-14805 | 563-581 | 641 CUAGUUGCUACUGUUUCUGTT | 642 CAGAAACAGUAGCAACUAGTT |
| AD-14806 | 566-584 | 643 GUUGCUACUGUUUCUGAGGTT | 644 CCUCAGAAACAGUAGCAACTT |
| AD-14807 | 625-643 | 645 UGGAGAGGCUGCUGCUACUTT | 646 AGUAGCAGCAGCCUCUCCATT |
| AD-14808 | 627-645 | 647 GAGAGGCUGCUGCUACUAUTT | 648 AUAGUAGCAGCAGCCUCUCTT |
| AD-14809 | 628-646 | 649 AGAGGCUGCUGCUACUAUATT | 650 UAUAGUAGCAGCAGCCUCUTT |
| AD-14810 | 632-650 | 651 GCUGCUGCUACUAUAGAAGTT | 652 CUUCUAUAGUAGCAGCAGCTT |
| AD-14811 | 513-531 | 653 UUUUUUGUGUUUUCAGGUUTT | 654 AACCUGAAAACACAAAAAATT |
| AD-14812 | 641-659 | 655 ACUAUAGAAGUUGAAAUUGTT | 656 CAAUUUCAACUUCUAUAGUTT |
| AD-14813 | 323-341 | 657 UUAGUAAAACCUGGAGUGGTT | 658 CCACUCCAGGUUUUACUAATT |
| AD-14814 | 717-735 | 659 GCCUUACUCCUGAAACAUATT | 660 UAUGUUUCAGGAGUAAGGCTT |
| AD-14815 | 646-664 | 661 AGAAGUUGAAAUUGCAUCCTT | 662 GGAUGCAAUUUCAACUUCUTT |
| AD-14816 | 592-610 | 663 UGCCACAGGAUUUUCAGUATT | 664 UACUGAAAAUCCUGUGGCATT |
| AD-14817 | 590-608 | 665 GCUGCCACAGGAUUUUCAGTT | 666 CUGAAAAUCCUGUGGCAGCTT |
| AD-14818 | 526-544 | 667 CAGGUUCAUGGGUGCCGCATT | 668 UGCGGCACCCAUGAACCUGTT |
| AD-14819 | 615-633 | 669 AAAUUGCUGCUGGAGAGGCTT | 670 GCCUCUCCAGCAGCAAUUUTT |
| AD-14820 | 617-635 | 671 AUUGCUGCUGGAGAGGCUGTT | 672 CAGCCUCUCCAGCAGCAAUTT |
| AD-14821 | 652-670 | 673 UGAAAUUGCAUCCCUUGCUTT | 674 AGCAAGGGAUGCAAUUUCATT |

TABLE 1a-continued

JCV Gene Walk; siRNAs targeting >95% of all stransins
(> = out of 388); Human specific pan-J TABLE 1a-continued JCV Gene Walk; siRNAs targeting >95% of all stransins
(> = out of 388); Human specific pan-JCV: 208 siRNAs;
all siRNAs double overhang design; dTdT, no
modifications. 1 a-1: sequences; 1 a-2: assay results

| Table 1a-1 duplex name | position in consensus | SEQ ID NO: | sense strand sequence (5'-3') | SEQ ID NO: | antisense strand sequence (5'-3') |
|---|---|---|---|---|---|
| AD-14858 | 4622-4640 | 747 | AGCCCACUUGUGUGGAUAGUU | 748 | CUAUCCACACAAGUGGGCUTT |
| AD-14859 | 4997-5015 | 749 | GUGCUGAAUAGGGAGGAAUTT | 750 | AUUCCUCCCUAUUCAGCACTT |
| AD-14860 | 5094-5112 | 751 | AGUAAGGGCGUGGAGGCUUTT | 752 | AAGCCUCCACGCCCUUACTT |
| AD-14861 | 4564-4582 | 753 | GUGACUUAACCCAAGAAGCTT | 754 | GCUUCUUGGGUUAAGUCACTT |
| AD-14862 | 5095-5113 | 755 | UAGUAAGGGCGUGGAGGCUTT | 756 | AGCCUCCACGCCCUUACUATT |
| AD-14863 | 4800-4818 | 757 | UCAUCAGCCUGAUUUUGGUTT | 758 | ACCAAAAUCAGGCUGAUGATT |
| AD-14864 | 4265-4283 | 759 | GUAGAAGACCCUAAAGACUTT | 760 | AGUCUUUAGGGUCUUCUACTT |
| AD-14865 | 4267-4285 | 761 | AGGUAGAAGACCCUAAAGATT | 762 | UCUUUAGGGUCUUCUACCUTT |
| AD-14866 | 4270-4288 | 763 | AAAAGGUAGAAGACCCUAATT | 764 | UUAGGGUCUUCUACCUUUTT |
| AD-14867 | 4269-4287 | 765 | AAAGGUAGAAGACCCUAAATT | 766 | UUUAGGGUCUUCUACCUUTT |
| AD-14868 | 2874-2892 | 767 | GAUUGUGCAGUGGAAAGAATT | 768 | UUCUUUCCACUGCACAAUCTT |
| AD-14869 | 2875-2893 | 769 | GGAUUGUGCAGUGGAAAGATT | 770 | UCUUUCCACUGCACAAUCCTT |
| AD-14870 | 3950-3968 | 771 | UGUAGACAGCCAUAUGCAGTT | 772 | CUGCAUAUGGCUGUCUACATT |
| AD-14871 | 3896-3914 | 773 | CAUGACUUUAACCCAGAAGTT | 774 | CUUCUGGGUUAAAGUCAUGTT |
| AD-14872 | 4990-5008 | 775 | AUAGGGAGGAAUCCAUGGATT | 776 | UCCAUGGAUUCCUCCCUAUTT |
| AD-14873 | 4994-5012 | 777 | CUGAAUAGGGAGGAAUCCATT | 778 | UGGAUUCCUCCCUAUUCAGTT |
| AD-14874 | 5000-5018 | 779 | AAAGUGCUGAAUAGGGAGGTT | 780 | CCUCCCUAUUCAGCACUUTT |
| AD-14875 | 4563-4581 | 781 | UGACUUAACCCAAGAAGCUTT | 782 | AGCUUCUUGGGUUAAGUCATT |
| AD-14876 | 3895-3913 | 783 | AUGACUUUAACCCAGAAGATT | 784 | UCUUCUGGGUUAAAGUCAUTT |
| AD-14877 | 4262-4280 | 785 | GAAGACCCUAAAGACUUUCTT | 786 | GAAAGUCUUUAGGGUCUUCTT |
| AD-14878 | 4162-4180 | 787 | AAAAGCUCAAAUUUUAUAUTT | 788 | UAUAAAAUUUGAGCUUUUTT |
| AD-14879 | 4798-4816 | 789 | AUCAGCCUGAUUUUGGUACTT | 790 | GUACCAAAAUCAGGCUGAUTT |
| AD-14880 | 4799-4817 | 791 | CAUCAGCCUGAUUUUGGUATT | 792 | UACCAAAAUCAGGCUGAUGTT |
| AD-14881 | 5006-5024 | 793 | AUGGACAAAGUGCUGAAUATT | 794 | UAUUCAGCACUUUGUCCAUTT |
| AD-14882 | 4264-4282 | 795 | UAGAAGACCCUAAAGACUUTT | 796 | AAGUCUUUAGGGUCUUCUATT |
| AD-14883 | 4268-4286 | 797 | AAGGUAGAAGACCCUAAAGTT | 798 | CUUUAGGGUCUUCUACCUTT |
| AD-14884 | 4623-4641 | 799 | CAGCCCACUUGUGUGGAUATT | 800 | UAUCCACACAAGUGGGCUGTT |
| AD-14885 | 4788-4806 | 801 | UUUUGGUACAUGGAAUAGUTT | 802 | ACUAUUCCAUGUACCAAAATT |
| AD-14886 | 4993-5011 | 803 | UGAAUAGGGAGGAAUCCAUTT | 804 | AUGGAUUCCUCCCUAUUCATT |
| AD-14887 | 4995-5013 | 805 | GCUGAAUAGGGAGGAAUCCTT | 806 | GGAUUCCUCCCUAUUCAGCTT |
| AD-14888 | 4996-5014 | 807 | UGCUGAAUAGGGAGGAAUCTT | 808 | GAUUCCUCCCUAUUCAGCATT |
| AD-14889 | 3952-3970 | 809 | UGUGUAGACAGCCAUAUGCTT | 810 | GCAUAUGGCUGUCUACACATT |
| AD-14890 | 4595-4613 | 811 | UGCUUUGAUUGCUUCAGACTT | 812 | GUCUGAAGCAAUCAAAGCATT |
| AD-14891 | 4596-4614 | 813 | UUGCUUUGAUUGCUUCAGATT | 814 | UCUGAAGCAAUCAAAGCAATT |
| AD-14892 | 4597-4615 | 815 | AUUGCUUUGAUUGCUUCAGTT | 816 | CUGAAGCAAUCAAAGCAAUTT |

TABLE 1a-continued

JCV Gene Walk; siRNAs targeting >95% of all stransins
(> = out of 388); Human specific pan-JCV: 208 siRNAs;
all siRNAs double overhang design; dTdT, no
modifications. 1 a-1: sequences; 1 a-2: assay results

| Table 1a-1 duplex name | position in consensus | SEQ ID NO: sense strand sequence (5'-3') | SEQ ID NO: antisense strand sequence (5'-3') |
|---|---|---|---|
| AD-14893 | 4599-4617 | 817 CUAUUGCUUUGAUUGCUUCUU | 818 GAAGCAAUCAAAGCAAUAGTT |
| AD-14894 | 4726-4744 | 819 AUUGCAAGGAAUGGCCUAAUU | 820 UUAGGCCAUUCCUUGCAAUTT |
| AD-14895 | 4753-4771 | 821 AUUUCCUCCUAAUUCUGAUU | 822 UCAGAAUUAGGAGGAAAAUTT |
| AD-14896 | 4802-4820 | 823 GCUCAUCAGCCUGAUUUUGUU | 824 CAAAAUCAGGCUGAUGAGCTT |
| AD-14897 | 4803-4821 | 825 UGCUCAUCAGCCUGAUUUUU | 826 AAAAUCAGGCUGAUGAGCATT |
| AD-14898 | 4806-4824 | 827 AGUUGCUCAUCAGCCUGAUU | 828 AUCAGGCUGAUGAGCAACUTT |
| AD-14899 | 5091-5109 | 829 AAGGGCGUGGAGGCUUUUUU | 830 AAAAAGCCUCCACGCCCUUTT |
| AD-14900 | 5093-5111 | 831 GUAAGGGCGUGGAGGCUUUU | 832 AAAGCCUCCACGCCCUUACTT |
| AD-14901 | 4259-4277 | 833 GACCCUAAAGACUUUCCUGUU | 834 CAGGAAAGUCUUUAGGGUCTT |
| AD-14902 | 3901-3919 | 835 AGGAGCAUGACUUUAACCCUU | 836 GGGUUAAAGUCAUGCUCCUTT |
| AD-14903 | 4757-4775 | 837 UGUGAUUUUCCUCCUAAUUUU | 838 AAUUAGGAGGAAAAUCACATT |
| AD-14904 | 4758-4776 | 839 UUGUGAUUUUCCUCCUAAUU | 840 AUUAGGAGGAAAAUCACAATT |
| AD-14905 | 4562-4580 | 841 GACUUAACCCAAGAAGCUCUU | 842 GAGCUUCUUGGGUUAAGUCTT |
| AD-14906 | 4585-4603 | 843 GCUUCAGACAAUGGUUUGGUU | 844 CCAAACCAUUGUCUGAAGCTT |
| AD-14907 | 4587-4605 | 845 UUGCUUCAGACAAUGGUUUUU | 846 AAACCAUUGUCUGAAGCAATT |
| AD-14908 | 4588-4606 | 847 AUUGCUUCAGACAAUGGUUU | 848 AACCAUUGUCUGAAGCAAUTT |
| AD-14909 | 4591-4609 | 849 UUGAUUGCUUCAGACAAUGUU | 850 CAUUGUCUGAAGCAAUCAATT |
| AD-14910 | 5003-5021 | 851 GACAAAGUGCUGAAUAGGGUU | 852 CCCUAUUCAGCACUUUGUCTT |
| AD-14911 | 4165-4183 | 853 AAGAAAAAGCUCAAAUUUUUU | 854 AAAAUUUGAGCUUUUUCUUTT |
| AD-14912 | 4166-4184 | 855 AAAGAAAAAGCUCAAAUUUUU | 856 AAAUUUGAGCUUUUUCUUUTT |
| AD-14913 | 4263-4281 | 857 AGAAGACCCUAAAGACUUUUU | 858 AAAGUCUUUAGGGUCUUCUTT |
| AD-14914 | 4274-4292 | 859 AAAAAAAGGUAGAAGACCUU | 860 GGUCUUCUACCUUUUUUUUTT |
| AD-14915 | 4266-4284 | 861 GGUAGAAGACCCUAAAGACUU | 862 GUCUUUAGGGUCUUCUACCTT |
| AD-14916 | 4272-4290 | 863 AAAAAGGUAGAAGACCCUUU | 864 AGGGUCUUCUACCUUUUUUTT |
| AD-14917 | 4271-4289 | 865 AAAAAGGUAGAAGACCCUAUU | 866 UAGGGUCUUCUACCUUUUUTT |
| AD-14918 | 4559-4577 | 867 UUAACCCAAGAAGCUCUUCUU | 868 GAAGAGCUUCUUGGGUUAATT |
| AD-14919 | 4789-4807 | 869 AUUUUGGUACAUGGAAUAGUU | 870 CUAUUCCAUGUACCAAAAUTT |
| AD-14920 | 4998-5016 | 871 AGUGCUGAAUAGGGAGGAAUU | 872 UUCCUCCCUAUUCAGCACUTT |
| AD-14921 | 5070-5088 | 873 GAGGCCAGGGAAAUUCCCUUU | 874 AGGGAAUUUCCCUGGCCUCTT |
| AD-14922 | 4158-4176 | 875 AGCUCAAAUUUUAUAUAAGUU | 876 CUUAUAUAAAAUUUGAGCUTT |
| AD-14923 | 5065-5083 | 877 CAGGGAAAUUCCCUUGUUUUU | 878 AAACAAGGGAAUUUCCCUGTT |
| AD-14924 | 2872-2890 | 879 UUGUGCAGUGGAAAGAAAGUU | 880 CUUUCUUUCCACUGCACAATT |
| AD-14925 | 4782-4800 | 881 UACAUGGAAUAGUUCAGAGUU | 882 CUCUGAACUAUUCCAUGUATT |
| AD-14926 | 4783-4801 | 883 GUACAUGGAAUAGUUCAGAUU | 884 UCUGAACUAUUCCAUGUACTT |
| AD-14927 | 5064-5082 | 885 AGGGAAAUUCCCUUGUUUUUU | 886 AAAACAAGGGAAUUUCCCUTT |
| AD-14928 | 5071-5089 | 887 GGAGGCCAGGGAAAUUCCCUU | 888 GGGAAUUUCCCUGGCCUCCTT |

TABLE 1a-continued

JCV Gene Walk; siRNAs targeting >95% of all stransins (> = out of 388); Human specific pan-JCV: 208 siRNAs; all siRNAs double overhang design; dTdT, no modifications. 1 a-1: sequences; 1 a-2: assay results

| Table 1a-1 duplex name | position in consensus | SEQ ID NO: | sense strand sequence (5'-3') | SEQ ID NO: | antisense strand sequence (5'-3') |
|---|---|---|---|---|---|
| AD-14929 | 3951-3969 | 889 | GUGUAGACAGCCAUAUGCATT | 890 | UGCAUAUGGCUGUCUACACTT |
| AD-14930 | 3949-3967 | 891 | GUAGACAGCCAUAUGCAGUTT | 892 | ACUGCAUAUGGCUGUCUACTT |
| AD-14931 | 4355-4373 | 893 | GAAGACCUGUUUUGCCAUGTT | 894 | CAUGGCAAAACAGGUCUUCTT |
| AD-14932 | 4363-4381 | 895 | AGUGGGAUGAAGACCUGUUTT | 896 | AACAGGUCUUCAUCCCACUTT |
| AD-14933 | 4356-4374 | 897 | UGAAGACCUGUUUUGCCAUTT | 898 | AUGGCAAAACAGGUCUUCATT |
| AD-14934 | 4361-4379 | 899 | UGGGAUGAAGACCUGUUUUTT | 900 | AAAACAGGUCUUCAUCCCATT |
| AD-14935 | 4560-4578 | 901 | CUUAACCCAAGAAGCUCUUTT | 902 | AAGAGCUUCUUGGGUUAAGTT |
| AD-14936 | 2873-2891 | 903 | AUUGUGCAGUGGAAAGAAATT | 904 | UUUCUUUCCACUGCACAAUTT |
| AD-14937 | 4730-4748 | 905 | CUUUAUUGCAAGGAAUGGCTT | 906 | GCCAUUCCUUGCAAUAAAGTT |
| AD-14938 | 3899-3917 | 907 | GAGCAUGACUUUAACCCAGTT | 908 | CUGGGUUAAAGUCAUGCUCTT |
| AD-14939 | 4756-4774 | 909 | GUGAUUUUCCUCCUAAUUCTT | 910 | GAAUUAGGAGGAAAAUCACTT |
| AD-14940 | 4590-4608 | 911 | UGAUUGCUUCAGACAAUGGTT | 912 | CCAUUGUCUGAAGCAAUCATT |
| AD-14941 | 4159-4177 | 913 | AAGCUCAAAUUUUAUAUAATT | 914 | UUAUAUAAAAUUUGAGCUUTT |
| AD-14942 | 2743-2761 | 915 | CUGGACAUGGAUCAAGCACTT | 916 | GUGCUUGAUCCAUGUCCAGTT |
| AD-14943 | 4155-4173 | 917 | UCAAAUUUUAUAUAAGAAATT | 918 | UUUCUUAUAUAAAAUUUGATT |
| AD-14944 | 2871-2889 | 919 | UGUGCAGUGGAAAGAAAGGTT | 920 | CCUUUCUUUCCACUGCACATT |
| AD-14945 | 4786-4804 | 921 | UUGGUACAUGGAAUAGUUCTT | 922 | GAACUAUUCCAUGUACCAATT |
| AD-14946 | 4364-4382 | 923 | AAGUGGGAUGAAGACCUGUTT | 924 | ACAGGUCUUCAUCCCACUUTT |
| AD-14947 | 4359-4377 | 925 | GGAUGAAGACCUGUUUUGCTT | 926 | GCAAAACAGGUCUUCAUCCTT |
| AD-14948 | 2744-2762 | 927 | UCUGGACAUGGAUCAAGCATT | 928 | UGCUUGAUCCAUGUCCAGATT |
| AD-14949 | 4787-4805 | 929 | UUUGGUACAUGGAAUAGUUTT | 930 | AACUAUUCCAUGUACCAAATT |

| Table 1a-2 duplex name | Residual luciferase activity (relative to control siRNA treated cells) | SD of residual luciferase activity | Residual luciferase activity +/- SD | Relative siRNA activity (normalized to positive control luc-siRNA) | SD of relative siRNA activity | Relative siRNA activity +/- SD |
|---|---|---|---|---|---|---|
| AD-14742 | 40.85 | 4.38 | 41 ± 4% | 82.24 | 8.83 | 82 ± 9% |
| AD-14743 | 20.92 | 4.10 | 21 ± 4% | 109.97 | 21.56 | 110 ± 22% |
| AD-14744 | 62.20 | 4.47 | 62 ± 4% | 52.56 | 3.78 | 53 ± 4% |
| AD-14745 | 43.97 | 2.60 | 44 ± 3% | 77.91 | 4.60 | 78 ± 5% |
| AD-14746 | 24.52 | 1.96 | 25 ± 2% | 104.96 | 8.38 | 105 ± 8% |
| AD-14747 | 32.67 | 4.51 | 33 ± 5% | 93.62 | 12.94 | 94 ± 13% |
| AD-14748 | 93.99 | 3.23 | 94 ± 3% | 8.36 | 0.29 | 8 ± 0% |
| AD-14749 | 55.16 | 2.81 | 55 ± 3% | 62.35 | 3.18 | 62 ± 3% |

-continued

| Table 1a-2 duplex name | Residual luciferase activity (relative to control siRNA treated cells) | SD of residual luciferase activity | Residual luciferase activity +/- SD | Relative siRNA activity (normalized to positive control luc-siRNA) | SD of relative siRNA activity | Relative siRNA activity +/- SD |
|---|---|---|---|---|---|---|
| AD-14750 | 30.86 | 3.11 | 31 ± 3% | 96.14 | 9.70 | 96 ± 10% |
| AD-14751 | 54.44 | 4.03 | 54 ± 4% | 63.35 | 4.69 | 63 ± 5% |
| AD-14752 | 53.88 | 7.58 | 54 ± 8% | 64.13 | 9.02 | 64 ± 9% |
| AD-14753 | 35.24 | 7.45 | 35 ± 7% | 90.05 | 19.03 | 90 ± 19% |
| AD-14754 | 70.39 | 2.80 | 70 ± 3% | 41.17 | 1.64 | 41 ± 2% |
| AD-14755 | 41.80 | 1.60 | 42 ± 2% | 80.93 | 3.10 | 81 ± 3% |
| AD-14756 | 56.69 | 3.05 | 57 ± 3% | 60.22 | 3.24 | 60 ± 3% |
| AD-14757 | 39.16 | 2.16 | 39 ± 2% | 84.60 | 4.67 | 85 ± 5% |
| AD-14758 | 39.79 | 2.95 | 40 ± 3% | 83.72 | 6.22 | 84 ± 6% |
| AD-14759 | 30.62 | 1.01 | 31 ± 1% | 96.48 | 3.20 | 96 ± 3% |
| AD-14760 | 28.14 | 2.74 | 28 ± 3% | 99.93 | 9.72 | 100 ± 10% |
| AD-14761 | 67.42 | 2.83 | 67 ± 3% | 45.30 | 1.90 | 45 ± 2% |
| AD-14762 | 36.10 | 1.30 | 36 ± 1% | 88.85 | 3.21 | 89 ± 3% |
| AD-14763 | 49.39 | 6.77 | 49 ± 7% | 78.14 | 10.71 | 78 ± 11% |
| AD-14764 | 74.04 | 5.32 | 74 ± 5% | 40.09 | 2.88 | 40 ± 3% |
| AD-14765 | 50.84 | 10.47 | 51 ± 10% | 75.91 | 15.63 | 76 ± 16% |
| AD-14766 | 72.59 | 3.55 | 73 ± 4% | 42.32 | 2.07 | 42 ± 2% |
| AD-14767 | 34.82 | 7.41 | 35 ± 7% | 100.63 | 21.40 | 101 ± 21% |
| AD-14768 | 48.68 | 6.31 | 49 ± 6% | 79.24 | 10.27 | 79 ± 10% |
| AD-14769 | 39.07 | 5.53 | 39 ± 6% | 94.08 | 13.31 | 94 ± 13% |
| AD-14770 | 45.59 | 5.89 | 46 ± 6% | 84.01 | 10.85 | 84 ± 11% |
| AD-14771 | 45.57 | 4.10 | 46 ± 4% | 84.04 | 7.56 | 84 ± 8% |
| AD-14772 | 33.12 | 3.64 | 33 ± 4% | 103.26 | 11.36 | 103 ± 11% |
| AD-14773 | 37.38 | 5.72 | 37 ± 6% | 96.69 | 14.78 | 97 ± 15% |
| AD-14774 | 42.38 | 4.41 | 42 ± 4% | 88.96 | 9.26 | 89 ± 9% |
| AD-14775 | 46.59 | 3.00 | 47 ± 3% | 82.47 | 5.31 | 82 ± 5% |
| AD-14776 | 71.28 | 8.67 | 71 ± 9% | 44.35 | 5.40 | 44 ± 5% |
| AD-14777 | 64.55 | 6.21 | 65 ± 6% | 54.74 | 5.26 | 55 ± 5% |
| AD-14778 | 60.45 | 8.91 | 60 ± 9% | 61.07 | 9.00 | 61 ± 9% |
| AD-14779 | 32.46 | 0.82 | 32 ± 1% | 104.27 | 2.63 | 104 ± 3% |
| AD-14780 | 22.96 | 2.86 | 23 ± 3% | 118.94 | 14.81 | 119 ± 15% |
| AD-14781 | 56.99 | 9.43 | 57 ± 9% | 66.41 | 10.99 | 66 ± 11% |
| AD-14782 | 29.90 | 8.74 | 30 ± 9% | 108.24 | 31.65 | 108 ± 32% |
| AD-14783 | 42.63 | 6.57 | 43 ± 7% | 88.58 | 13.66 | 89 ± 14% |
| AD-14784 | 67.06 | 1.35 | 67 ± 1% | 50.86 | 1.03 | 51 ± 1% |
| AD-14785 | 48.90 | 3.32 | 49 ± 3% | 78.89 | 5.35 | 79 ± 5% |

-continued

| Table 1a-2 duplex name | Residual luciferase activity (relative to control siRNA treated cells) | SD of residual luciferase activity | Residual luciferase activity +/- SD | Relative siRNA activity (normalized to positive control luc-siRNA) | SD of relative siRNA activity | Relative siRNA activity +/- SD |
|---|---|---|---|---|---|---|
| AD-14786 | 27.74 | 2.06 | 28 ± 2% | 111.57 | 8.29 | 112 ± 8% |
| AD-14787 | 38.77 | 6.24 | 39 ± 6% | 94.53 | 15.22 | 95 ± 15% |
| AD-14788 | 32.84 | 8.60 | 33 ± 9% | 103.70 | 27.17 | 104 ± 27% |
| AD-14789 | 46.96 | 1.70 | 47 ± 2% | 81.89 | 2.96 | 82 ± 3% |
| AD-14790 | 43.61 | 4.90 | 44 ± 5% | 87.06 | 9.79 | 87 ± 10% |
| AD-14791 | 35.55 | 4.34 | 36 ± 4% | 99.51 | 12.15 | 100 ± 12% |
| AD-14792 | 38.22 | 3.51 | 38 ± 4% | 95.38 | 8.75 | 95 ± 9% |
| AD-14793 | 90.85 | 5.92 | 91 ± 6% | 14.13 | 0.92 | 14 ± 1% |
| AD-14794 | 83.37 | 3.27 | 83 ± 3% | 25.68 | 1.01 | 26 ± 1% |
| AD-14795 | 55.06 | 3.61 | 55 ± 4% | 69.38 | 4.55 | 69 ± 5% |
| AD-14796 | 30.98 | 5.78 | 31 ± 6% | 106.56 | 19.89 | 107 ± 20% |
| AD-14797 | 28.95 | 3.15 | 29 ± 3% | 109.70 | 11.95 | 110 ± 12% |
| AD-14798 | 67.39 | 3.70 | 67 ± 4% | 50.35 | 2.76 | 50 ± 3% |
| AD-14799 | 66.83 | 4.72 | 67 ± 5% | 51.21 | 3.61 | 51 ± 4% |
| AD-14800 | 33.26 | 5.72 | 33 ± 6% | 103.04 | 17.71 | 103 ± 18% |
| AD-14801 | 39.15 | 4.57 | 39 ± 5% | 93.96 | 10.97 | 94 ± 11% |
| AD-14802 | 91.20 | 5.35 | 91 ± 5% | 13.58 | 0.80 | 14 ± 1% |
| AD-14803 | 34.15 | 7.94 | 34 ± 8% | 101.67 | 23.64 | 102 ± 24% |
| AD-14804 | 30.08 | 6.54 | 30 ± 7% | 107.96 | 23.48 | 108 ± 23% |
| AD-14805 | 32.44 | 4.27 | 32 ± 4% | 104.31 | 13.73 | 104 ± 14% |
| AD-14806 | 35.62 | 3.11 | 36 ± 3% | 99.41 | 8.67 | 99 ± 9% |
| AD-14807 | 28.27 | 7.28 | 28 ± 7% | 110.76 | 28.52 | 111 ± 29% |
| AD-14808 | 30.29 | 3.96 | 30 ± 4% | 107.63 | 14.08 | 108 ± 14% |
| AD-14809 | 31.59 | 4.46 | 32 ± 4% | 105.63 | 14.91 | 106 ± 15% |
| AD-14810 | 30.11 | 5.71 | 30 ± 6% | 107.91 | 20.46 | 108 ± 20% |
| AD-14811 | 55.27 | 6.82 | 55 ± 7% | 69.06 | 8.52 | 69 ± 9% |
| AD-14812 | 45.27 | 5.99 | 45 ± 6% | 84.51 | 11.19 | 85 ± 11% |
| AD-14813 | 77.97 | 7.01 | 78 ± 7% | 34.01 | 3.06 | 34 ± 3% |
| AD-14814 | 29.54 | 3.56 | 30 ± 4% | 108.78 | 13.09 | 109 ± 13% |
| AD-14815 | 65.04 | 3.18 | 65 ± 3% | 53.97 | 2.64 | 54 ± 3% |
| AD-14816 | 64.03 | 4.63 | 64 ± 5% | 55.53 | 4.02 | 56 ± 4% |
| AD-14817 | 37.83 | 2.89 | 38 ± 3% | 95.99 | 7.33 | 96 ± 7% |
| AD-14818 | 28.88 | 5.60 | 29 ± 6% | 109.82 | 21.30 | 110 ± 21% |
| AD-14819 | 92.90 | 4.87 | 93 ± 5% | 10.97 | 0.58 | 11 ± 1% |
| AD-14820 | 75.41 | 3.69 | 75 ± 4% | 37.97 | 1.86 | 38 ± 2% |
| AD-14821 | 73.08 | 6.22 | 73 ± 6% | 41.57 | 3.54 | 42 ± 4% |

-continued

| Table 1a-2 duplex name | Residual luciferase activity (relative to control siRNA treated cells) | SD of residual luciferase activity | Residual luciferase activity +/- SD | Relative siRNA activity (normalized to positive control luc-siRNA) | SD of relative siRNA activity | Relative siRNA activity +/- SD |
|---|---|---|---|---|---|---|
| AD-14822 | 86.39 | 9.34 | 86 ± 9% | 21.02 | 2.27 | 21 ± 2% |
| AD-14823 | 96.50 | 10.46 | 97 ± 10% | 5.40 | 0.59 | 5 ± 1% |
| AD-14824 | 32.62 | 3.41 | 33 ± 3% | 104.03 | 10.89 | 104 ± 11% |
| AD-14825 | 102.71 | 7.66 | 103 ± 8% | -4.18 | 0.31 | -4 ± 0% |
| AD-14826 | 92.45 | 5.66 | 92 ± 6% | 11.66 | 0.71 | 12 ± 1% |
| AD-14827 | 63.46 | 16.38 | 63 ± 16% | 46.00 | 11.88 | 46 ± 12% |
| AD-14828 | 45.99 | 15.21 | 46 ± 15% | 67.99 | 22.49 | 68 ± 22% |
| AD-14829 | 40.54 | 16.03 | 41 ± 16% | 74.86 | 29.60 | 75 ± 30% |
| AD-14830 | 117.10 | 3.66 | 117 ± 4% | -21.52 | 0.67 | -22 ± 1% |
| AD-14831 | 54.78 | 21.12 | 55 ± 21% | 56.93 | 21.95 | 57 ± 22% |
| AD-14832 | 67.07 | 10.81 | 67 ± 11% | 41.46 | 6.68 | 41 ± 7% |
| AD-14833 | 71.52 | 11.90 | 72 ± 12% | 35.85 | 5.97 | 36 ± 6% |
| AD-14834 | 58.05 | 16.37 | 58 ± 16% | 52.81 | 14.89 | 53 ± 15% |
| AD-14835 | 93.36 | 5.43 | 93 ± 5% | 8.36 | 0.49 | 8 ± 0% |
| AD-14836 | 108.84 | 4.85 | 109 ± 5% | -11.13 | 0.50 | -11 ± 0% |
| AD-14837 | 106.68 | 10.06 | 107 ± 10% | -8.41 | 0.79 | -8 ± 1% |
| AD-14838 | 37.06 | 6.68 | 37 ± 7% | 79.23 | 14.28 | 79 ± 14% |
| AD-14839 | 36.03 | 7.54 | 36 ± 8% | 80.53 | 16.84 | 81 ± 17% |
| AD-14840 | 38.51 | 5.90 | 39 ± 6% | 77.40 | 11.86 | 77 ± 12% |
| AD-14841 | 110.86 | 8.91 | 111 ± 9% | -13.67 | 1.10 | -14 ± 1% |
| AD-14842 | 34.83 | 5.51 | 35 ± 6% | 82.04 | 12.98 | 82 ± 13% |
| AD-14843 | 23.75 | 6.04 | 24 ± 6% | 95.99 | 24.41 | 96 ± 24% |
| AD-14844 | 27.47 | 5.29 | 27 ± 5% | 91.30 | 17.57 | 91 ± 18% |
| AD-14845 | 93.12 | 4.70 | 93 ± 5% | 8.67 | 0.44 | 9 ± 0% |
| AD-14846 | 81.72 | 8.26 | 82 ± 8% | 23.01 | 2.33 | 23 ± 2% |
| AD-14847 | 77.89 | 5.29 | 78 ± 5% | 27.83 | 1.89 | 28 ± 2% |
| AD-14848 | 44.40 | 4.95 | 44 ± 5% | 69.99 | 7.81 | 70 ± 8% |
| AD-14849 | 46.41 | 5.08 | 46 ± 5% | 67.46 | 7.38 | 67 ± 7% |
| AD-14850 | 35.52 | 6.70 | 36 ± 7% | 81.17 | 15.31 | 81 ± 15% |
| AD-14851 | 36.07 | 1.13 | 36 ± 1% | 102.63 | 3.22 | 103 ± 3% |
| AD-14852 | 67.98 | 6.75 | 68 ± 7% | 51.41 | 5.11 | 51 ± 5% |
| AD-14853 | 69.44 | 3.07 | 69 ± 3% | 49.05 | 2.17 | 49 ± 2% |
| AD-14854 | 29.12 | 6.88 | 29 ± 7% | 113.79 | 26.89 | 114 ± 27% |
| AD-14855 | 36.04 | 7.07 | 36 ± 7% | 102.68 | 20.14 | 103 ± 20% |
| AD-14856 | 33.61 | 7.93 | 34 ± 8% | 106.57 | 25.15 | 107 ± 25% |
| AD-14857 | 50.76 | 8.76 | 51 ± 9% | 79.04 | 13.64 | 79 ± 14% |

-continued

| Table 1a-2 duplex name | Residual luciferase activity (relative to control siRNA treated cells) | SD of residual luciferase activity | Residual luciferase activity +/- SD | Relative siRNA activity (normalized to positive control luc-siRNA) | SD of relative siRNA activity | Relative siRNA activity +/- SD |
|---|---|---|---|---|---|---|
| AD-14858 | 53.60 | 7.26 | 54 ± 7% | 74.49 | 10.09 | 74 ± 10% |
| AD-14859 | 39.07 | 9.34 | 39 ± 9% | 97.82 | 23.38 | 98 ± 23% |
| AD-14860 | 62.78 | 6.85 | 63 ± 7% | 59.75 | 6.52 | 60 ± 7% |
| AD-14861 | 87.47 | 1.86 | 87 ± 2% | 20.12 | 0.43 | 20 ± 0% |
| AD-14862 | 79.95 | 4.02 | 80 ± 4% | 32.19 | 1.62 | 32 ± 2% |
| AD-14863 | 30.46 | 4.49 | 30 ± 4% | 111.64 | 16.46 | 112 ± 16% |
| AD-14864 | 33.18 | 5.07 | 33 ± 5% | 107.26 | 16.38 | 107 ± 16% |
| AD-14865 | 26.25 | 3.98 | 26 ± 4% | 118.39 | 17.96 | 118 ± 18% |
| AD-14866 | 36.73 | 1.24 | 37 ± 1% | 101.57 | 3.44 | 102 ± 3% |
| AD-14867 | 33.16 | 3.13 | 33 ± 3% | 107.30 | 10.12 | 107 ± 10% |
| AD-14868 | 29.91 | 4.56 | 30 ± 5% | 112.52 | 17.16 | 113 ± 17% |
| AD-14869 | 28.24 | 3.66 | 28 ± 4% | 115.20 | 14.91 | 115 ± 15% |
| AD-14870 | 50.37 | 3.04 | 50 ± 3% | 79.67 | 4.81 | 80 ± 5% |
| AD-14871 | 39.37 | 5.11 | 39 ± 5% | 97.32 | 12.63 | 97 ± 13% |
| AD-14872 | 34.71 | 4.12 | 35 ± 4% | 104.82 | 12.43 | 105 ± 12% |
| AD-14873 | 32.14 | 1.79 | 32 ± 2% | 108.93 | 6.07 | 109 ± 6% |
| AD-14874 | 101.77 | 4.87 | 102 ± 5% | -2.85 | 0.14 | <3 ± 0% |
| AD-14875 | 80.81 | 4.39 | 81 ± 4% | 30.80 | 1.67 | 31 ± 2% |
| AD-14876 | 30.74 | 1.88 | 31 ± 2% | 111.18 | 6.81 | 111 ± 7% |
| AD-14877 | 57.38 | 2.84 | 57 ± 3% | 68.42 | 3.39 | 68 ± 3% |
| AD-14878 | 70.23 | 3.35 | 70 ± 3% | 47.79 | 2.28 | 48 ± 2% |
| AD-14879 | 79.03 | 7.72 | 79 ± 8% | 33.66 | 3.29 | 34 ± 3% |
| AD-14880 | 21.65 | 2.46 | 22 ± 2% | 125.78 | 14.28 | 126 ± 14% |
| AD-14881 | 27.66 | 1.71 | 28 ± 2% | 116.13 | 7.17 | 116 ± 7% |
| AD-14882 | 34.01 | 2.94 | 34 ± 3% | 105.93 | 9.16 | 106 ± 9% |
| AD-14883 | 40.62 | 3.22 | 41 ± 3% | 95.33 | 7.56 | 95 ± 8% |
| AD-14884 | 35.73 | 5.94 | 36 ± 6% | 103.18 | 17.14 | 103 ± 17% |
| AD-14885 | 47.40 | 7.65 | 47 ± 8% | 84.45 | 13.63 | 84 ± 14% |
| AD-14886 | 37.23 | 3.94 | 37 ± 4% | 100.76 | 10.67 | 101 ± 11% |
| AD-14887 | 42.94 | 7.26 | 43 ± 7% | 91.61 | 15.50 | 92 ± 15% |
| AD-14888 | 32.58 | 4.06 | 33 ± 4% | 108.24 | 13.50 | 108 ± 14% |
| AD-14889 | 83.09 | 2.98 | 83 ± 3% | 27.15 | 0.97 | 27 ± 1% |
| AD-14890 | 59.49 | 2.94 | 59 ± 3% | 65.04 | 3.22 | 65 ± 3% |
| AD-14891 | 21.93 | 5.52 | 22 ± 6% | 125.32 | 31.52 | 125 ± 32% |
| AD-14892 | 72.69 | 2.19 | 73 ± 2% | 43.84 | 1.32 | 44 ± 1% |
| AD-14893 | 24.43 | 7.07 | 24 ± 7% | 121.32 | 35.11 | 121 ± 35% |

-continued

| Table 1a-2 duplex name | Residual luciferase activity (relative to control siRNA treated cells) | SD of residual luciferase activity | Residual luciferase activity +/- SD | Relative siRNA activity (normalized to positive control luc-siRNA) | SD of relative siRNA activity | Relative siRNA activity +/- SD |
|---|---|---|---|---|---|---|
| AD-14894 | 33.84 | 5.08 | 34 ± 5% | 106.20 | 15.95 | 106 ± 16% |
| AD-14895 | 21.68 | 4.46 | 22 ± 4% | 125.73 | 25.84 | 126 ± 26% |
| AD-14896 | 26.99 | 5.01 | 27 ± 5% | 117.20 | 21.73 | 117 ± 22% |
| AD-14897 | 29.04 | 2.72 | 29 ± 3% | 113.92 | 10.67 | 114 ± 11% |
| AD-14898 | 32.64 | 4.87 | 33 ± 5% | 108.14 | 16.13 | 108 ± 16% |
| AD-14899 | 61.71 | 4.59 | 62 ± 5% | 61.47 | 4.57 | 61 ± 5% |
| AD-14900 | 31.01 | 2.84 | 31 ± 3% | 110.75 | 10.14 | 111 ± 10% |
| AD-14901 | 31.47 | 1.57 | 31 ± 2% | 110.01 | 5.49 | 110 ± 5% |
| AD-14902 | 76.99 | 0.55 | 77 ± 1% | 36.95 | 0.26 | 37 ± 0% |
| AD-14903 | 20.55 | 3.55 | 21 ± 4% | 127.55 | 22.05 | 128 ± 22% |
| AD-14904 | 22.65 | 6.87 | 23 ± 7% | 124.18 | 37.68 | 124 ± 38% |
| AD-14905 | 56.98 | 4.94 | 57 ± 5% | 69.07 | 5.99 | 69 ± 6% |
| AD-14906 | 34.20 | 3.66 | 34 ± 4% | 105.63 | 11.29 | 106 ± 11% |
| AD-14907 | 28.59 | 8.12 | 29 ± 8% | 114.64 | 32.56 | 115 ± 33% |
| AD-14908 | 34.08 | 3.36 | 34 ± 3% | 105.82 | 10.44 | 106 ± 10% |
| AD-14909 | 76.57 | 2.33 | 77 ± 2% | 37.61 | 1.15 | 38 ± 1% |
| AD-14910 | 46.50 | 4.14 | 46 ± 4% | 85.89 | 7.64 | 86 ± 8% |
| AD-14911 | 29.62 | 2.02 | 30 ± 2% | 112.99 | 7.69 | 113 ± 8% |
| AD-14912 | 22.27 | 0.48 | 22 ± 0% | 124.78 | 2.69 | 125 ± 3% |
| AD-14913 | 59.80 | 2.85 | 60 ± 3% | 64.53 | 3.08 | 65 ± 3% |
| AD-14914 | 93.21 | 5.10 | 93 ± 5% | 10.90 | 0.60 | 11 ± 1% |
| AD-14915 | 25.99 | 4.45 | 26 ± 4% | 118.82 | 20.34 | 119 ± 20% |
| AD-14916 | 48.20 | 1.46 | 48 ± 1% | 83.16 | 2.51 | 83 ± 3% |
| AD-14917 | 41.03 | 3.07 | 41 ± 3% | 94.67 | 7.08 | 95 ± 7% |
| AD-14918 | 110.62 | 6.34 | 111 ± 6% | -17.04 | 0.98 | -17 ± 1% |
| AD-14919 | 73.66 | 3.68 | 74 ± 4% | 42.29 | 2.11 | 42 ± 2% |
| AD-14920 | 19.80 | 1.72 | 20 ± 2% | 128.75 | 11.20 | 129 ± 11% |
| AD-14921 | 33.13 | 1.14 | 33 ± 1% | 107.34 | 3.71 | 107 ± 4% |
| AD-14922 | 52.94 | 6.99 | 53 ± 7% | 63.41 | 8.37 | 63 ± 8% |
| AD-14923 | 33.77 | 8.92 | 34 ± 9% | 89.23 | 23.56 | 89 ± 24% |
| AD-14924 | 64.47 | 10.96 | 64 ± 11% | 47.86 | 8.13 | 48 ± 8% |
| AD-14925 | 97.16 | 7.57 | 97 ± 8% | 3.83 | 0.30 | 4 ± 0% |
| AD-14926 | 27.29 | 8.79 | 27 ± 9% | 97.96 | 31.56 | 98 ± 32% |
| AD-14927 | 27.02 | 10.01 | 27 ± 10% | 98.33 | 36.42 | 98 ± 36% |
| AD-14928 | 76.75 | 4.78 | 77 ± 5% | 31.32 | 1.95 | 31 ± 2% |
| AD-14929 | 32.92 | 9.44 | 33 ± 9% | 90.38 | 25.93 | 90 ± 26% |

-continued

| Table 1a-2 duplex name | Residual luciferase activity (relative to control siRNA treated cells) | SD of residual luciferase activity | Residual luciferase activity +/- SD | Relative siRNA activity (normalized to positive control luc-siRNA) | SD of relative siRNA activity | Relative siRNA activity +/- SD |
|---|---|---|---|---|---|---|
| AD-14930 | 31.00 | 9.40 | 31 ± 9% | 92.97 | 28.21 | 93 ± 28% |
| AD-14931 | 31.36 | 8.73 | 31 ± 9% | 92.48 | 25.74 | 92 ± 26% |
| AD-14932 | 32.42 | 9.01 | 32 ± 9% | 91.05 | 25.29 | 91 ± 25% |
| AD-14933 | 39.94 | 6.96 | 40 ± 7% | 80.92 | 14.10 | 81 ± 14% |
| AD-14934 | 42.94 | 7.66 | 43 ± 8% | 76.88 | 13.71 | 77 ± 14% |
| AD-14935 | 47.74 | 8.48 | 48 ± 8% | 70.41 | 12.51 | 70 ± 13% |
| AD-14936 | 35.21 | 4.02 | 35 ± 4% | 87.29 | 9.97 | 87 ± 10% |
| AD-14937 | 89.25 | 3.53 | 89 ± 4% | 14.48 | 0.57 | 14 ± 1% |
| AD-14938 | 29.38 | 6.46 | 29 ± 6% | 95.15 | 20.91 | 95 ± 21% |
| AD-14939 | 26.45 | 8.33 | 26 ± 8% | 99.09 | 31.21 | 99 ± 31% |
| AD-14940 | 77.50 | 6.51 | 78 ± 7% | 30.31 | 2.55 | 30 ± 3% |
| AD-14941 | 36.40 | 10.76 | 36 ± 11% | 85.68 | 25.32 | 86 ± 25% |
| AD-14942 | 65.11 | 5.84 | 65 ± 6% | 47.01 | 4.22 | 47 ± 4% |
| AD-14943 | 89.96 | 4.69 | 90 ± 5% | 13.52 | 0.71 | 14 ± 1% |
| AD-14944 | 48.98 | 5.85 | 49 ± 6% | 68.74 | 8.21 | 69 ± 8% |
| AD-14945 | 43.45 | 3.29 | 43 ± 3% | 76.18 | 5.77 | 76 ± 6% |
| AD-14946 | 41.25 | 1.26 | 41 ± 1% | 79.15 | 2.43 | 79 ± 2% |
| AD-14947 | 42.10 | 7.34 | 42 ± 7% | 78.01 | 13.60 | 78 ± 14% |
| AD-14948 | 42.39 | 5.75 | 42 ± 6% | 77.62 | 10.54 | 78 ± 11% |
| AD-14949 | 27.68 | 5.79 | 28 ± 6% | 97.44 | 20.39 | 97 ± 20% |

Tables 1b-1 and 1b-2

TABLE 1b siRNAs targeting JCV transcripts for primary screen; 1b-1: sequences; 1b-2: assay results.
C* column describes chemistries as follows:

| Table 1b-1 duplex name | C* | position in consensus | SEQ ID NO: | sense strand sequence (5'-3') | SEQ ID NO: | antisense strand sequence (5'-3') |
|---|---|---|---|---|---|---|
| AD-12598 | a | 1426-1444 | 1 | AcuuuuAGGGuuGuAcGGGTsT | 2 | CcCGuAcAACCCuAAAAGUTsT |
| AD-12708 | b | 1426-1444 | 3 | AcuuuuAGGGuuGuAcGGGTsT | 4 | CCCGuAcAACCCuAAAAGUTsT |
| AD-12599 | a | 1427-1445 | 5 | cuuuuAGGGuuGuAcGGGATsT | 6 | UcCCGuAcAACCCuAAAAGTsT |
| AD-12709 | b | 1427-1445 | 7 | cuuuuAGGGuuGuAcGGGATsT | 8 | UCCCGuAcAACCCuAAAAGTsT |
| AD-12600 | a | 2026-2044 | 9 | cAGAGcAcAAGGcGuAccuTsT | 10 | AgGuACGCCUUGUGCUCUGTsT |
| AD-12710 | b | 2026-2044 | 11 | cAGAGcAcAAGGcGuAccuTsT | 12 | AGGuACGCCUUGUGCUCUGTsT |
| AD-12784 | c | 2026-2044 | 13 | caGAGcAcAAGGcGuAccuTsT | 14 | AGGuACGCCUUGUGCUCUGTsT |
| AD-12832 | d | 2026-2044 | 15 | caGAGcAcAAGGcGuAccuTsT | 16 | AgGuACGCCUUGUGCUCUGTsT |
| AD-12601 | a | 1431-1449 | 17 | uAGGGuuGuAcGGGAcuGuTsT | 18 | AcAGUCCCGuAcAACCCuATsT |

TABLE 1b-continued siRNAs targeting JCV transcripts for primary
screen; 1b-1: sequences; 1b-2: assay results.
C* column describes chemistries as follows:

| Table 1b-1 duplex name | C* | position in consensus | SEQ ID NO: | sense strand sequence (5'-3') | SEQ ID NO: | antisense strand sequence (5'-3') |
|---|---|---|---|---|---|---|
| AD-12785 | c | 1431-1449 | 19 | uaGGGuuGuAcGGGAcuGuTsT | 20 | AcAGUCCCGuAcAACCCuATsT |
| AD-12602 | a | 1432-1450 | 21 | AGGGuuGuAcGGGAcuGuATsT | 22 | uacAGUCCCGuAcAACCCUTsT |
| AD-12711 | b | 1432-1450 | 23 | AGGGuuGuAcGGGAcuGuATsT | 24 | uAcAGUCCCGuAcAACCCUTsT |
| AD-12786 | c | 1432-1450 | 25 | AgGGuuGuAcGGGAcuGuATsT | 26 | uAcAGUCCCGuAcAACCCUTsT |
| AD-12833 | d | 1432-1450 | 27 | AgGGuuGuAcGGGAcuGuATsT | 28 | uacAGUCCCGuAcAACCCUTsT |
| AD-12603 | a | 1436-1454 | 29 | uuGuAcGGGAcuGuAAcAcTsT | 30 | GuGUuAcAGUCCCGuAcAATsT |
| AD-12712 | b | 1436-1454 | 31 | uuGuAcGGGAcuGuAAcAcTsT | 32 | GUGUuAcAGUCCCGuAcAATsT |
| AD-12604 | a | 4794-4812 | 33 | GccuGAuuuuGGuAcAuGGTsT | 34 | CcAUGuAccAAAAUcAGGCTsT |
| AD-12605 | a | 5099-5117 | 35 | GAAGuAGuAAGGGcGuGGATsT | 36 | UccACGCCCUuACuACUUCTsT |
| AD-12713 | b | 5099-5117 | 37 | GAAGuAGuAAGGGcGuGGATsT | 38 | UCcACGCCCUuACuACUUCTsT |
| AD-12787 | c | 5099-5117 | 39 | GaAGuAGuAAGGGcGuGGATsT | 40 | UCcACGCCCUuACuACUUCTsT |
| AD-12834 | d | 5099-5117 | 41 | GaAGuAGuAAGGGcGuGGATsT | 42 | UccACGCCCUuACuACUUCTsT |
| AD-12606 | a | 713-731 | 43 | AuAGGccuuAcuccuGAAATsT | 44 | UuUcAGGAGuAAGGCCuATsT |
| AD-12714 | b | 713-731 | 45 | AuAGGccuuAcuccuGAAATsT | 46 | UUUcAGGAGuAAGGCCuATsT |
| AD-12607 | a | 3946-3964 | 47 | GAcAGccAuAuGcAGuAGuTsT | 48 | AcuACUGcAuAUGGCUGUCTsT |
| AD-12715 | b | 3946-3964 | 49 | GAcAGccAuAuGcAGuAGuTsT | 50 | ACuACUGcAuAUGGCUGUCTsT |
| AD-12788 | c | 3946-3964 | 51 | GacAGccAuAuGcAGuAGuTsT | 52 | ACuACUGcAuAUGGCUGUCTsT |
| AD-12835 | d | 3946-3964 | 53 | GacAGccAuAuGcAGuAGuTsT | 54 | AcuACUGcAuAUGGCUGUCTsT |
| AD-12608 | a | 1128-1146 | 55 | AAAcuAcuuGGGcAAuAGuTsT | 56 | AcuAUUGCCcAAGuAGUUUTsT |
| AD-12716 | b | 1128-1146 | 57 | AAAcuAcuuGGGcAAuAGuTsT | 58 | ACuAUUGCCcAAGuAGUUUTsT |
| AD-12789 | c | 1128-1146 | 59 | AaAcuAcuuGGGcAAuAGuTsT | 60 | ACuAUUGCCcAAGuAGUUUTsT |
| AD-12836 | d | 1128-1146 | 61 | AaAcuAcuuGGGcAAuAGuTsT | 62 | AcuAUUGCCcAAGuAGUUUTsT |
| AD-12609 | a | 525-543 | 63 | ucAGGuucAuGGGuGccGcTsT | 64 | GcGGcACCcAUGAACCUGATsT |
| AD-12717 | b | 525-543 | 65 | ucAGGuucAuGGGuGccGcTsT | 66 | GCGGcACCcAUGAACCUGATsT |
| AD-12610 | a | 5096-5114 | 67 | GuAGuAAGGGcGuGGAGGcTsT | 68 | GcCUCcACGCCCUuACuACTsT |
| AD-12718 | b | 5096-5114 | 69 | GuAGuAAGGGcGuGGAGGcTsT | 70 | GCCUCcACGCCCUuACuACTsT |
| AD-12611 | a | 4727-4745 | 71 | uAuuGcAAGGAAuGGccuATsT | 72 | uaGGCcAUUCCUUGcAAuATsT |
| AD-12719 | b | 4727-4745 | 73 | uAuuGcAAGGAAuGGccuATsT | 74 | uAGGCcAUUCCUUGcAAuATsT |
| AD-12790 | c | 4727-4745 | 75 | uauuGcAAGGAAuGGccuATsT | 76 | uAGGCcAUUCCUUGcAAuATsT |
| AD-12837 | d | 4727-4745 | 77 | uauuGcAAGGAAuGGccuATsT | 78 | uaGGCcAUUCCUUGcAAuATsT |
| AD-12612 | a | 5097-5115 | 79 | AGuAGuAAGGGcGuGGAGGTsT | 80 | CcUCcACGCCCUuACuACUTsT |
| AD-12720 | b | 5097-5115 | 81 | AGuAGuAAGGGcGuGGAGGTsT | 82 | CCUCcACGCCCUuACuACUTsT |
| AD-12791 | c | 5097-5115 | 83 | AguAGuAAGGGcGuGGAGGTsT | 84 | CCUCcACGCCCUuACuACUTsT |
| AD-12838 | d | 5097-5115 | 85 | AguAGuAAGGGcGuGGAGGTsT | 86 | CcUCcACGCCCUuACuACUTsT |
| AD-12613 | a | 4601-4619 | 87 | uGcuAuuGcuuuGAuuGcuTsT | 88 | AgcAAUcAAAGcAAuAGCATsT |
| AD-12721 | b | 4601-4619 | 89 | uGcuAuuGcuuuGAuuGcuTsT | 90 | AGcAAUcAAAGcAAuAGCATsT |

TABLE 1b-continued siRNAs targeting JCV transcripts for primary
screen; 1b-1: sequences; 1b-2: assay results.
C* column describes chemistries as follows:

| Table 1b-1 duplex name | C* | position in consensus | SEQ ID NO: | sense strand sequence (5'-3') | SEQ ID NO: | antisense strand sequence (5'-3') |
|---|---|---|---|---|---|---|
| AD-12792 | c | 4601-4619 | 91 | ugcuAuuGcuuuGAuuGcuTsT | 92 | AGcAAUcAAAGcAAuAGcATsT |
| AD-12839 | d | 4601-4619 | 93 | ugcuAuuGcuuuGAuuGcuTsT | 94 | AgcAAUcAAAGcAAuAGcATsT |
| AD-12614 | a | 4600-4618 | 95 | GcuAuuGcuuuGAuuGcuuTsT | 96 | AaGcAAUcAAAGcAAuAGCTsT |
| AD-12722 | b | 4600-4618 | 97 | GcuAuuGcuuuGAuuGcuuTsT | 98 | AAGcAAUcAAAGcAAuAGCTsT |
| AD-12615 | a | 1421-1439 | 99 | ccuuuAcuuuuAGGGuuGuTsT | 100 | AcAACCCuAAAAGuAAAGGTsT |
| AD-12616 | a | 1424-1442 | 101 | uuAcuuuuAGGGuuGuAcGTsT | 102 | CguAcAACCCuAAAAGuAATsT |
| AD-12723 | b | 1424-1442 | 103 | uuAcuuuuAGGGuuGuAcGTsT | 104 | CGuAcAACCCuAAAAGuAATsT |
| AD-12617 | a | 1403-1421 | 105 | GcuccucAAuGGAuGuuGcTsT | 106 | GcAAcAUCcAUUGAGGAGCTsT |
| AD-12618 | a | 1534-1552 | 107 | uuAuAAGAGGAGGAGuAGATsT | 108 | UcuACUCCUCCUCUuAuAATsT |
| AD-12724 | b | 1534-1552 | 109 | uuAuAAGAGGAGGAGuAGATsT | 110 | UCuACUCCUCCUCUuAuAATsT |
| AD-12619 | a | 5098-5116 | 111 | AAGuAGuAAGGGcGuGGAGTsT | 112 | CuCcACGCCCUuACuACUUTsT |
| AD-12725 | b | 5098-5116 | 113 | AAGuAGuAAGGGcGuGGAGTsT | 114 | CUCcACGCCCUuACuACUUTsT |
| AD-12793 | c | 5098-5116 | 115 | AaGuAGuAAGGGcGuGGAGTsT | 116 | CUCcACGCCCUuACuACUUTsT |
| AD-12840 | d | 5098-5116 | 117 | AaGuAGuAAGGGcGuGGAGTsT | 118 | CuCcACGCCCUuACuACUUTsT |
| AD-12620 | a | 1430-1448 | 119 | uuAGGGuuGuAcGGGAcuGTsT | 120 | caGUCCCGuAcAACCCuAATsT |
| AD-12726 | b | 1430-1448 | 121 | uuAGGGuuGuAcGGGAcuGTsT | 122 | cAGUCCCGuAcAACCCuAATsT |
| AD-12621 | a | 1701-1719 | 123 | GAcAuGcuuccuuGuuAcATsT | 124 | UguAAcAAGGAAGcAUGUCTsT |
| AD-12727 | b | 1701-1719 | 125 | GAcAuGcuuccuuGuuAcATsT | 126 | UGuAAcAAGGAAGcAUGUCTsT |
| AD-12794 | c | 1701-1719 | 127 | GacAuGcuuccuuGuuAcATsT | 128 | UGuAAcAAGGAAGcAUGUCTsT |
| AD-12841 | d | 1701-1719 | 129 | GacAuGcuuccuuGuuAcATsT | 130 | UguAAcAAGGAAGcAUGUCTsT |
| AD-12622 | a | 2066-2084 | 131 | uGuuGAAuGuuGGGuuccuTsT | 132 | AgGAACCcAAcAUUcAAcATsT |
| AD-12728 | b | 2066-2084 | 133 | uGuuGAAuGuuGGGuuccuTsT | 134 | AGGAACCcAAcAUUcAAcATsT |
| AD-12795 | c | 2066-2084 | 135 | uguuGAAuGuuGGGuuccuTsT | 136 | AGGAACCcAAcAUUcAAcATsT |
| AD-12842 | d | 2066-2084 | 137 | uguuGAAuGuuGGGuuccuTsT | 138 | AgGAACCcAAcAUUcAAcATsT |
| AD-12623 | a | 4561-4579 | 139 | AcuuAAcccAAGAAGcucuTsT | 140 | AgAGCUUCUUGGGUuAAGUTsT |
| AD-12729 | b | 4561-4579 | 141 | AcuuAAcccAAGAAGcucuTsT | 142 | AGAGCUUCUUGGGUuAAGUTsT |
| AD-12624 | a | 4797-4815 | 143 | ucAGccuGAuuuuGGuAcATsT | 144 | UguACcAAAAUcAGGCUGATsT |
| AD-12730 | b | 4797-4815 | 145 | ucAGccuGAuuuuGGuAcATsT | 146 | UGuACcAAAAUcAGGCUGATsT |
| AD-12625 | a | 1428-1446 | 147 | uuuuAGGGuuGuAcGGGAcTsT | 148 | GuCCCGuAcAACCCuAAAATsT |
| AD-12731 | b | 1428-1446 | 149 | uuuuAGGGuuGuAcGGGAcTsT | 150 | GUCCCGuAcAACCCuAAAATsT |
| AD-12626 | a | 1429-1447 | 151 | uuuAGGGuuGuAcGGGAcuTsT | 152 | AgUCCCGuAcAACCCuAAATsT |
| AD-12732 | b | 1429-1447 | 153 | uuuAGGGuuGuAcGGGAcuTsT | 154 | AGUCCCGuAcAACCCuAAATsT |
| AD-12627 | a | 662-680 | 155 | ucccuuGcuAcuGuAGAGGTsT | 156 | CcUCuAcAGuAGcAAGGGATsT |
| AD-12733 | b | 662-680 | 157 | ucccuuGcuAcuGuAGAGGTsT | 158 | CCUCuAcAGuAGcAAGGGATsT |
| AD-12628 | a | 663-681 | 159 | cccuuGcuAcuGuAGAGGGTsT | 160 | CcCUCuAcAGuAGcAAGGGTsT |
| AD-12734 | b | 663-681 | 161 | cccuuGcuAcuGuAGAGGGTsT | 162 | CCCUCuAcAGuAGcAAGGGTsT |

TABLE 1b-continued siRNAs targeting JCV transcripts for primary screen; 1b-1: sequences; 1b-2: assay results. C* column describes chemistries as follows:

| Table 1b-1 duplex name | C* | position in consensus | SEQ ID NO: | sense strand sequence (5'-3') | SEQ ID NO: | antisense strand sequence (5'-3') |
|---|---|---|---|---|---|---|
| AD-12629 | a | 1402-1420 | 163 | uGcuccucAAuGGAuGuuGTsT | 164 | caAcAUCcAUUGAGGAGcATsT |
| AD-12735 | b | 1402-1420 | 165 | uGcuccucAAuGGAuGuuGTsT | 166 | cAAcAUCcAUUGAGGAGcATsT |
| AD-12796 | c | 1402-1420 | 167 | ugcuccucAAuGGAuGuuGTsT | 168 | cAAcAUCcAUUGAGGAGcATsT |
| AD-12843 | d | 1402-1420 | 169 | ugcuccucAAuGGAuGuuGTsT | 170 | caAcAUCcAUUGAGGAGcATsT |
| AD-12630 | a | 1398-1416 | 171 | GAucuGcuccucAAuGGAuTsT | 172 | AuCcAUUGAGGAGcAGAUCTsT |
| AD-12736 | b | 1398-1416 | 173 | GAucuGcuccucAAuGGAuTsT | 174 | AUCcAUUGAGGAGcAGAUCTsT |
| AD-12797 | c | 1398-1416 | 175 | GaucuGcuccucAAuGGAuTsT | 176 | AUCcAUUGAGGAGcAGAUCTsT |
| AD-12844 | d | 1398-1416 | 177 | GaucuGcuccucAAuGGAuTsT | 178 | AuCcAUUGAGGAGcAGAUCTsT |
| AD-12631 | a | 1399-1417 | 179 | AucuGcuccucAAuGGAuGTsT | 180 | caUCcAUUGAGGAGcAGAUTsT |
| AD-12737 | b | 1399-1417 | 181 | AucuGcuccucAAuGGAuGTsT | 182 | cAUCcAUUGAGGAGcAGAUTsT |
| AD-12632 | a | 1400-1418 | 183 | ucuGcuccucAAuGGAuGuTsT | 184 | AcAUCcAUUGAGGAGcAGATsT |
| AD-12633 | a | 1401-1419 | 185 | cuGcuccucAAuGGAuGuuTsT | 186 | AacAUCcAUUGAGGAGcAGTsT |
| AD-12738 | b | 1401-1419 | 187 | cuGcuccucAAuGGAuGuuTsT | 188 | AAcAUCcAUUGAGGAGcAGTsT |
| AD-12634 | a | 1435-1453 | 189 | GuuGuAcGGGAcuGuAAcATsT | 190 | UgUuAcAGUCCCGuAcAACTsT |
| AD-12739 | b | 1435-1453 | 191 | GuuGuAcGGGAcuGuAAcATsT | 192 | UGUuAcAGUCCCGuAcAACTsT |
| AD-12635 | a | 1437-1455 | 193 | uGuAcGGGAcuGuAAcAccTsT | 194 | GgUGUuAcAGUCCCGuAcATsT |
| AD-12740 | b | 1437-1455 | 195 | uGuAcGGGAcuGuAAcAccTsT | 196 | GGUGUuAcAGUCCCGuAcATsT |
| AD-12798 | c | 1437-1455 | 197 | uguAcGGGAcuGuAAcAccTsT | 198 | GGUGUuAcAGUCCCGuAcATsT |
| AD-12845 | d | 1437-1455 | 199 | uguAcGGGAcuGuAAcAccTsT | 200 | GgUGUuAcAGUCCCGuAcATsT |
| AD-12636 | a | 1438-1456 | 201 | GuAcGGGAcuGuAAcAccuTsT | 202 | AgGUGUuAcAGUCCCGuACTsT |
| AD-12741 | b | 1438-1456 | 203 | GuAcGGGAcuGuAAcAccuTsT | 204 | AGGUGUuAcAGUCCCGuACTsT |
| AD-12637 | a | 4796-4814 | 205 | cAGccuGAuuuuGGuAcAuTsT | 206 | AuGuACcAAAAUcAGGCUGTsT |
| AD-12742 | b | 4796-4814 | 207 | cAGccuGAuuuuGGuAcAuTsT | 208 | AUGuACcAAAAUcAGGCUGTsT |
| AD-12799 | c | 4796-4814 | 209 | caGccuGAuuuuGGuAcAuTsT | 210 | AUGuACcAAAAUcAGGCUGTsT |
| AD-12846 | d | 4796-4814 | 211 | caGccuGAuuuuGGuAcAuTsT | 212 | AuGuACcAAAAUcAGGCUGTsT |
| AD-12638 | a | 4992-5010 | 213 | GAAuAGGGAGGAAuccAuGTsT | 214 | caUGGAUUCCUCCCuAUUCTsT |
| AD-12743 | b | 4992-5010 | 215 | GAAuAGGGAGGAAuccAuGTsT | 216 | cAUGGAUUCCUCCCuAUUCTsT |
| AD-12800 | c | 4992-5010 | 217 | GaAuAGGGAGGAAuccAuGTsT | 218 | cAUGGAUUCCUCCCuAUUCTsT |
| AD-12847 | d | 4992-5010 | 219 | GaAuAGGGAGGAAuccAuGTsT | 220 | caUGGAUUCCUCCCuAUUCTsT |
| AD-12639 | a | 4999-5017 | 221 | AAGuGcuGAAuAGGGAGGATsT | 222 | UcCUCCCuAUUcAGcACUUTsT |
| AD-12744 | b | 4999-5017 | 223 | AAGuGcuGAAuAGGGAGGATsT | 224 | UCCUCCCuAUUcAGcACUUTsT |
| AD-12801 | c | 4999-5017 | 225 | AaGuGcuGAAuAGGGAGGATsT | 226 | UCCUCCCuAUUcAGcACUUTsT |
| AD-12848 | d | 4999-5017 | 227 | AaGuGcuGAAuAGGGAGGATsT | 228 | UcCUCCCuAUUcAGcACUUTsT |
| AD-12640 | a | 630-648 | 229 | AGGcuGcuGcuAcuAuAGATsT | 230 | UcuAuAGuAGcAGcAGCCUTsT |
| AD-12745 | b | 630-648 | 231 | AGGcuGcuGcuAcuAuAGATsT | 232 | UCuAuAGuAGcAGcAGCCUTsT |
| AD-12802 | c | 630-648 | 233 | AgGcuGcuGcuAcuAuAGATsT | 234 | UCuAuAGuAGcAGcAGCCUTsT |

TABLE 1b-continued siRNAs targeting JCV transcripts for primary
screen; 1b-1: sequences; 1b-2: assay results.
C* column describes chemistries as follows:

| Table 1b-1 duplex name | C* | position in consensus | SEQ ID NO: | sense strand sequence (5'-3') | SEQ ID NO: | antisense strand sequence (5'-3') |
|---|---|---|---|---|---|---|
| AD-12849 | d | 630-648 | 235 | AgGcuGcuGcuAcuAuAGATsT | 236 | UcuAuAGuAGcAGcAGCCUTsT |
| AD-12641 | a | 3947-3965 | 237 | AGAcAGccAuAuGcAGuAGTsT | 238 | CuACUGcAuAUGGCUGUCUTsT |
| AD-12803 | c | 3947-3965 | 239 | AgAcAGccAuAuGcAGuAGTsT | 240 | CuACUGcAuAUGGCUGUCUTsT |
| AD-12642 | a | 524-542 | 241 | uucAGGuucAuGGGuGccGTsT | 242 | CgGcACCcAUGAACCUGAATsT |
| AD-12746 | b | 524-542 | 243 | uucAGGuucAuGGGuGccGTsT | 244 | CGGcACCcAUGAACCUGAATsT |
| AD-12643 | a | 3948-3966 | 245 | uAGAcAGccAuAuGcAGuATsT | 246 | uaCUGcAuAUGGCUGUCuATsT |
| AD-12747 | b | 3948-3966 | 247 | uAGAcAGccAuAuGcAGuATsT | 248 | uACUGcAuAUGGCUGUCuATsT |
| AD-12804 | c | 3948-3966 | 249 | uaGAcAGccAuAuGcAGuATsT | 250 | uACUGcAuAUGGCUGUCuATsT |
| AD-12850 | d | 3948-3966 | 251 | uaGAcAGccAuAuGcAGuATsT | 252 | uaCUGcAuAUGGCUGUCuATsT |
| AD-12644 | a | 3900-3918 | 253 | GGAGcAuGAcuuuAAcccATsT | 254 | UgGGUuAAAGUcAUGCUCCTsT |
| AD-12748 | b | 3900-3918 | 255 | GGAGcAuGAcuuuAAcccATsT | 256 | UGGGUuAAAGUcAUGCUCCTsT |
| AD-12805 | c | 3900-3918 | 257 | GgAGcAuGAcuuuAAcccATsT | 258 | UGGGUuAAAGUcAUGCUCCTsT |
| AD-12851 | d | 3900-3918 | 259 | GgAGcAuGAcuuuAAcccATsT | 260 | UgGGUuAAAGUcAUGCUCCTsT |
| AD-12645 | a | 1417-1435 | 261 | GuuGccuuuAcuuuAGGGTsT | 262 | CcCuAAAAGuAAAGGcAACTsT |
| AD-12749 | b | 1417-1435 | 263 | GuuGccuuuAcuuuAGGGTsT | 264 | CCCuAAAAGuAAAGGcAACTsT |
| AD-12646 | a | 4565-4583 | 265 | uGuGAcuuAAcccAAGAAGTsT | 266 | CuUCUUGGGUuAAGUcAcATsT |
| AD-12750 | b | 4565-4583 | 267 | uGuGAcuuAAcccAAGAAGTsT | 268 | CUUCUUGGGUuAAGUcACATsT |
| AD-12806 | c | 4565-4583 | 269 | uguGAcuuAAcccAAGAAGTsT | 270 | CUUCUUGGGUuAAGUcAcATsT |
| AD-12852 | d | 4565-4583 | 271 | uguGAcuuAAcccAAGAAGTsT | 272 | CuUCUUGGGUuAAGUcAcATsT |
| AD-12647 | a | 4598-4616 | 273 | uAuuGcuuuGAuuGcuucATsT | 274 | UgAAGcAAUcAAAGcAAuATsT |
| AD-12751 | b | 4598-4616 | 275 | uAuuGcuuuGAuuGcuucATsT | 276 | UGAAGcAAUcAAAGcAAuATsT |
| AD-12807 | c | 4598-4616 | 277 | uauuGcuuuGAuuGcuucATsT | 278 | UGAAGcAAUcAAAGcAAuATsT |
| AD-12853 | d | 4598-4616 | 279 | uauuGcuuuGAuuGcuucATsT | 280 | UgAAGcAAUcAAAGcAAuATsT |
| AD-12648 | a | 2060-2078 | 281 | AuAuccuGuuGAAuGuuGGTsT | 282 | CcAAcAUUcAAcAGGAuAUTsT |
| AD-12649 | a | 4729-4747 | 283 | uuuAuuGcAAGGAAuGGccTsT | 284 | GgCcAUUCCUUGcAAuAAATsT |
| AD-12752 | b | 4729-4747 | 285 | uuuAuuGcAAGGAAuGGccTsT | 286 | GGCcAUUCCUUGcAAuAAATsT |
| AD-12650 | a | 1122-1140 | 287 | uGGAAGAAAcuAcuuGGGcTsT | 288 | GcCcAAGuAGUUUCUUCcATsT |
| AD-12753 | b | 1122-1140 | 289 | uGGAAGAAAcuAcuuGGGcTsT | 290 | GCCcAAGuAGUUUCUUCcATsT |
| AD-12808 | c | 1122-1140 | 291 | ugGAAGAAAcuAcuuGGGcTsT | 292 | GCCcAAGuAGUUUCUUCcATsT |
| AD-12854 | d | 1122-1140 | 293 | ugGAAGAAAcuAcuuGGGcTsT | 294 | GcCcAAGuAGUUUCUUCcATsT |
| AD-12651 | a | 4261-4279 | 295 | AAGAcccuAAAGAcuuuccTsT | 296 | GgAAAGUCUUuAGGGUCUUTsT |
| AD-12754 | b | 4261-4279 | 297 | AAGAcccuAAAGAcuuuccTsT | 298 | GGAAAGUCUUuAGGGUCUUTsT |
| AD-12809 | c | 4261-4279 | 299 | AaGAcccuAAAGAcuuuccTsT | 300 | GGAAAGUCUUuAGGGUCUUTsT |
| AD-12855 | d | 4261-4279 | 301 | AaGAcccuAAAGAcuuuccTsT | 302 | GgAAAGUCUUuAGGGUCUUTsT |
| AD-12652 | a | 1412-1430 | 303 | uGGAuGuuGccuuuAcuuuTsT | 304 | AaAGuAAAGGcAAcAUCcATsT |
| AD-12755 | b | 1412-1430 | 305 | uGGAuGuuGccuuuAcuuuTsT | 306 | AAAGuAAAGGcAAcAUCcATsT |

TABLE 1b-continued siRNAs targeting JCV transcripts for primary
screen; 1b-1: sequences; 1b-2: assay results.
C* column describes chemistries as follows:

| Table 1b-1 duplex name | C* | position in consensus | SEQ ID NO: | sense strand sequence (5'-3') | SEQ ID NO: | antisense strand sequence (5'-3') |
|---|---|---|---|---|---|---|
| AD-12810 | c | 1412-1430 | 307 | ugGAuGuuGccuuuAcuuuTsT | 308 | AAAGuAAAGGcAAcAUCcATsT |
| AD-12856 | d | 1412-1430 | 309 | ugGAuGuuGccuuuAcuuuTsT | 310 | AaAGuAAAGGcAAcAUCcATsT |
| AD-12653 | a | 4592-4610 | 311 | uuuGAuuGcuucAGAcAAuTsT | 312 | AuUGUCUGAAGcAAUcAAATsT |
| AD-12756 | b | 4592-4610 | 313 | uuuGAuuGcuucAGAcAAuTsT | 314 | AUUGUCUGAAGcAAUcAAATsT |
| AD-12654 | a | 4991-5009 | 315 | AAuAGGGAGGAAuccAuGGTsT | 316 | CcAUGGAUUCCUCCCuAUUTsT |
| AD-12811 | c | 4991-5009 | 317 | AauAGGGAGGAAuccAuGGTsT | 318 | CcAUGGAUUCCUCCCuAUUTsT |
| AD-12655 | a | 5004-5022 | 319 | GGAcAAAGuGcuGAAuAGGTsT | 320 | CcuAUUcAGcACUUUGUCCTsT |
| AD-12757 | b | 5004-5022 | 321 | GGAcAAAGuGcuGAAuAGGTsT | 322 | CCuAUUcAGcACUUUGUCCTsT |
| AD-12812 | c | 5004-5022 | 323 | GgAcAAAGuGcuGAAuAGGTsT | 324 | CCuAUUcAGcACUUUGUCCTsT |
| AD-12857 | d | 5004-5022 | 325 | GgAcAAAGuGcuGAAuAGGTsT | 326 | CcuAUUcAGcACUUUGUCCTsT |
| AD-12656 | a | 5005-5023 | 327 | uGGAcAAAGuGcuGAAuAGTsT | 328 | CuAUUcAGcACUUUGUCcATsT |
| AD-12813 | c | 5005-5023 | 329 | ugGAcAAAGuGcuGAAuAGTsT | 330 | CuAUUcAGcACUUUGUCcATsT |
| AD-12657 | a | 654-672 | 331 | AAAuuGcAucccuuGcuAcTsT | 332 | GuAGcAAGGGAuGcAAUUUTsT |
| AD-12814 | c | 654-672 | 333 | AaAuuGcAucccuuGcuAcTsT | 334 | GuAGcAAGGGAuGcAAUUUTsT |
| AD-12658 | a | 659-677 | 335 | GcAucccuuGcuAcuGuAGTsT | 336 | CuAcAGuAGcAAGGGAUGCTsT |
| AD-12659 | a | 4273-4291 | 337 | AAAAAAGGuAGAAGAcccTsT | 338 | GgGUCUUCuACCUUUUUUUTsT |
| AD-12758 | b | 4273-4291 | 339 | AAAAAAGGuAGAAGAcccTsT | 340 | GGGUCUUCuACCUUUUUUUTsT |
| AD-12815 | c | 4273-4291 | 341 | AaAAAAGGuAGAAGAcccTsT | 342 | GGGUCUUCuACCUUUUUUUTsT |
| AD-12858 | d | 4273-4291 | 343 | AaAAAAGGuAGAAGAcccTsT | 344 | GgGUCUUCuACCUUUUUUUTsT |
| AD-12660 | a | 2025-2043 | 345 | AcAGAGcAcAAGGcGuAccTsT | 346 | GguACGCCUUGUGCUCUGUTsT |
| AD-12759 | b | 2025-2043 | 347 | AcAGAGcAcAAGGcGuAccTsT | 348 | GGuACGCCUUGUGCUCUGUTsT |
| AD-12661 | a | 4791-4809 | 349 | uGAuuuuGGuAcAuGGAAuTsT | 350 | AuUCcAUGuAccAAAAUcATsT |
| AD-12760 | b | 4791-4809 | 351 | uGAuuuuGGuAcAuGGAAuTsT | 352 | AUUCcAUGuAccAAAAUcATsT |
| AD-12816 | c | 4791-4809 | 353 | ugAuuuuGGuAcAuGGAAuTsT | 354 | AUUCcAUGuAccAAAAUcATsT |
| AD-12859 | d | 4791-4809 | 355 | ugAuuuuGGuAcAuGGAAuTsT | 356 | AuUCcAUGuAccAAAAUcATsT |
| AD-12662 | a | 1433-1451 | 357 | GGGuuGuAcGGGAcuGuAATsT | 358 | UuAcAGUCCCGuAcAACCCTsT |
| AD-12817 | c | 1433-1451 | 359 | GgGuuGuAcGGGAcuGuAATsT | 360 | UuAcAGUCCCGuAcAACCCTsT |
| AD-12663 | a | 1434-1452 | 361 | GGuuGuAcGGGAcuGuAAcTsT | 362 | GuuAcAGUCCCGuAcAACCTsT |
| AD-12761 | b | 1434-1452 | 363 | GGuuGuAcGGGAcuGuAAcTsT | 364 | GUuAcAGUCCCGuAcAACCTsT |
| AD-12818 | c | 1434-1452 | 365 | GguuGuAcGGGAcuGuAAcTsT | 366 | GUuAcAGUCCCGuAcAACCTsT |
| AD-12860 | d | 1434-1452 | 367 | GguuGuAcGGGAcuGuAAcTsT | 368 | GuuAcAGUCCCGuAcAACCTsT |
| AD-12664 | a | 1440-1458 | 369 | AcGGGAcuGuAAcAccuGcTsT | 370 | GcAGGUGUuAcAGUCCCGUTsT |
| AD-12665 | a | 1442-1460 | 371 | GGGAcuGuAAcAccuGcucTsT | 372 | GaGcAGGUGUuAcAGUCCCTsT |
| AD-12762 | b | 1442-1460 | 373 | GGGAcuGuAAcAccuGcucTsT | 374 | GAGcAGGUGUuAcAGUCCCTsT |
| AD-12819 | c | 1442-1460 | 375 | GgGAcuGuAAcAccuGcucTsT | 376 | GAGcAGGUGUuAcAGUCCCTsT |
| AD-12861 | d | 1442-1460 | 377 | GgGAcuGuAAcAccuGcucTsT | 378 | GaGcAGGUGUuAcAGUCCCTsT |

TABLE 1b-continued siRNAs targeting JCV transcripts for primary
screen; 1b-1: sequences; 1b-2: assay results.
C* column describes chemistries as follows:

| Table 1b-1 duplex name | C* | position in consensus | SEQ ID NO: | sense strand sequence (5'-3') | SEQ ID NO: | antisense strand sequence (5'-3') |
|---|---|---|---|---|---|---|
| AD-12666 | a | 1608-1626 | 379 | AcuccAGAAAuGGGuGAccTsT | 380 | GgUcACCcAUUUCUGGAGUTsT |
| AD-12763 | b | 1608-1626 | 381 | AcuccAGAAAuGGGuGAccTsT | 382 | GGUcACCcAUUUCUGGAGUTsT |
| AD-12667 | a | 4793-4811 | 383 | ccuGAuuuuGGuAcAuGGATsT | 384 | UccAUGuACcAAAAUcAGGTsT |
| AD-12764 | b | 4793-4811 | 385 | ccuGAuuuuGGuAcAuGGATsT | 386 | UCcAUGuACcAAAAUcAGGTsT |
| AD-12668 | a | 5001-5019 | 387 | cAAAGuGcuGAAuAGGGAGTsT | 388 | CuCCCuAUUcAGcACUUUGTsT |
| AD-12765 | b | 5001-5019 | 389 | cAAAGuGcuGAAuAGGGAGTsT | 390 | CUCCCuAUUcAGcACUUUGTsT |
| AD-12820 | c | 5001-5019 | 391 | caAAGuGcuGAAuAGGGAGTsT | 392 | CUCCCuAUUcAGcACUUUGTsT |
| AD-12862 | d | 5001-5019 | 393 | caAAGuGcuGAAuAGGGAGTsT | 394 | CuCCCuAUUcAGcACUUUGTsT |
| AD-12669 | a | 5066-5084 | 395 | ccAGGGAAAuucccuuGuuTsT | 396 | AacAAGGGAAUUUCCCUGGTsT |
| AD-12766 | b | 5066-5084 | 397 | ccAGGGAAAuucccuuGuuTsT | 398 | AAcAAGGGAAUUUCCCUGGTsT |
| AD-12670 | a | 5069-5087 | 399 | AGGccAGGGAAAuucccuuTsT | 400 | AaGGGAAUUUCCCUGGCCUTsT |
| AD-12767 | b | 5069-5087 | 401 | AGGccAGGGAAAuucccuuTsT | 402 | AAGGGAAUUUCCCUGGCCUTsT |
| AD-12821 | c | 5069-5087 | 403 | AgGccAGGGAAAuucccuuTsT | 404 | AAGGGAAUUUCCCUGGCCUTsT |
| AD-12863 | d | 5069-5087 | 405 | AgGccAGGGAAAuucccuuTsT | 406 | AaGGGAAUUUCCCUGGCCUTsT |
| AD-12671 | a | 564-582 | 407 | uAGuuGcuAcuGuuucuGATsT | 408 | UcAGAAAcAGuAGcAACuATsT |
| AD-12822 | c | 564-582 | 409 | uaGuuGcuAcuGuuucuGATsT | 410 | UcAGAAAcAGuAGcAACuATsT |
| AD-12672 | a | 633-651 | 411 | cuGcuGcuAcuAuAGAAGuTsT | 412 | AcUUCuAuAGuAGcAGcAGTsT |
| AD-12768 | b | 633-651 | 413 | cuGcuGcuAcuAuAGAAGuTsT | 414 | ACUUCuAuAGuAGcAGcAGTsT |
| AD-12673 | a | 634-652 | 415 | uGcuGcuAcuAuAGAAGuuTsT | 416 | AaCUUCuAuAGuAGcAGcATsT |
| AD-12769 | b | 634-652 | 417 | uGcuGcuAcuAuAGAAGuuTsT | 418 | AACUUCuAuAGuAGcAGcATsT |
| AD-12823 | c | 634-652 | 419 | ugcuGcuAcuAuAGAAGuuTsT | 420 | AACUUCuAuAGuAGcAGcATsT |
| AD-12864 | d | 634-652 | 421 | ugcuGcuAcuAuAGAAGuuTsT | 422 | AaCUUCuAuAGuAGcAGcATsT |
| AD-12674 | a | 635-653 | 423 | GcuGcuAcuAuAGAAGuuGTsT | 424 | caACUUCuAuAGuAGcAGCTsT |
| AD-12770 | b | 635-653 | 425 | GcuGcuAcuAuAGAAGuuGTsT | 426 | cAACUUCuAuAGuAGcAGCTsT |
| AD-12675 | a | 636-654 | 427 | cuGcuAcuAuAGAAGuuGATsT | 428 | UcAACUUCuAuAGuAGcAGTsT |
| AD-12676 | a | 637-655 | 429 | uGcuAcuAuAGAAGuuGAATsT | 430 | UucAACUUCuAuAGuAGcATsT |
| AD-12771 | b | 637-655 | 431 | uGcuAcuAuAGAAGuuGAATsT | 432 | UUcAACUUCuAuAGuAGcATsT |
| AD-12824 | c | 637-655 | 433 | ugcuAcuAuAGAAGuuGAATsT | 434 | UUcAACUUCuAuAGuAGcATsT |
| AD-12865 | d | 637-655 | 435 | ugcuAcuAuAGAAGuuGAATsT | 436 | UucAACUUCuAuAGuAGcATsT |
| AD-12677 | a | 912-930 | 437 | cAGAAGAcuAcuAuGAuAuTsT | 438 | AuAUcAuAGuAGUCUUCUGTsT |
| AD-12825 | c | 912-930 | 439 | caGAAGAcuAcuAuGAuAuTsT | 440 | AuAUcAuAGuAGUCUUCUGTsT |
| AD-12678 | a | 4153-4171 | 441 | AAAuuuuAuAuAAGAAAcuTsT | 442 | AgUUUCUuAuAuAAAAUUUTsT |
| AD-12772 | b | 4153-4171 | 443 | AAAuuuuAuAuAAGAAAcuTsT | 444 | AGUUUCU uAuAuAAAAUUUTsT |
| AD-12826 | c | 4153-4171 | 445 | AaAuuuuAuAuAAGAAAcuTsT | 446 | AGUUUCU uAuAuAAAAUUUTsT |
| AD-12866 | d | 4153-4171 | 447 | AaAuuuuAuAuAAGAAAcuTsT | 448 | AgUUUCUuAuAuAAAAUUUTsT |
| AD-12679 | a | 4779-4797 | 449 | AuGGAAuAGuucAGAGGuuTsT | 450 | AaCCUCUGAACuAUUCcAUTsT |

TABLE 1b-continued siRNAs targeting JCV transcripts for primary
screen; 1b-1: sequences; 1b-2: assay results.
C* column describes chemistries as follows:

| Table 1b-1 duplex name | C* | position in consensus | SEQ ID NO: | sense strand sequence (5'-3') | SEQ ID NO: | antisense strand sequence (5'-3') |
|---|---|---|---|---|---|---|
| AD-12773 | b | 4779-4797 | 451 | AuGGAAAuAGuucAGAGGuuTsT | 452 | AACCUCUGAACuAUUCcAUTsT |
| AD-12680 | a | 4780-4798 | 453 | cAuGGAAuAGuucAGAGGuTsT | 454 | AcCUCUGAACuAUUCcAUGTsT |
| AD-12774 | b | 4780-4798 | 455 | cAuGGAAuAGuucAGAGGuTsT | 456 | ACCUCUGAACuAUUCcAUGTsT |
| AD-12827 | c | 4780-4798 | 457 | cauGGAAuAGuucAGAGGuTsT | 458 | ACCUCUGAACuAUUCcAUGTsT |
| AD-12867 | d | 4780-4798 | 459 | cauGGAAuAGuucAGAGGuTsT | 460 | AcCUCUGAACuAUUCcAUGTsT |
| AD-12681 | a | 4781-4799 | 461 | AcAuGGAAuAGuucAGAGGTsT | 462 | CcUCUGAACuAUUCcAUGUTsT |
| AD-12775 | b | 4781-4799 | 463 | AcAuGGAAuAGuucAGAGGTsT | 464 | CCUCUGAACuAUUCcAUGUTsT |
| AD-12682 | a | 4784-4802 | 465 | GGuAcAuGGAAuAGuucAGTsT | 466 | CuGAACuAUUCcAUGuACCTsT |
| AD-12776 | b | 4784-4802 | 467 | GGuAcAuGGAAuAGuucAGTsT | 468 | CUGAACuAUUCcAUGuACCTsT |
| AD-12828 | c | 4784-4802 | 469 | GguAcAuGGAAuAGuucAGTsT | 470 | CUGAACuAUUCcAUGuACCTsT |
| AD-12868 | d | 4784-4802 | 471 | GguAcAuGGAAuAGuucAGTsT | 472 | CuGAACuAUUCcAUGuACCTsT |
| AD-12683 | a | 4785-4803 | 473 | uGGuAcAuGGAAuAGuucATsT | 474 | UgAACuAUUCcAUGuACcATsT |
| AD-12777 | b | 4785-4803 | 475 | uGGuAcAuGGAAuAGuucATsT | 476 | UGAACuAUUCcAUGuACcATsT |
| AD-12829 | c | 4785-4803 | 477 | ugGuAcAuGGAAuAGuucATsT | 478 | UGAACuAUUCcAUGuACcATsT |
| AD-12869 | d | 4785-4803 | 479 | ugGuAcAuGGAAuAGuucATsT | 480 | UgAACuAUUCcAUGuACcATsT |
| AD-12684 | a | 719-737 | 481 | cuuAcuccuGAAAcAuAuGTsT | 482 | cauAUGUUUcAGGAGuAAGTsT |
| AD-12778 | b | 719-737 | 483 | cuuAcuccuGAAAcAuAuGTsT | 484 | cAuAUGUUUcAGGAGuAAGTsT |
| AD-12685 | a | 909-927 | 485 | AuccAGAAGAcuAcuAuGATsT | 486 | UcAuAGuAGUCUUCUGGAUTsT |
| AD-12686 | a | 1119-1137 | 487 | uuuuGGAAGAAAcuAcuuGTsT | 488 | caAGuAGUUUCUUCcAAAATsT |
| AD-12779 | b | 1119-1137 | 489 | uuuuGGAAGAAAcuAcuuGTsT | 490 | cAAGuAGUUUCUUCcAAAATsT |
| AD-12687 | a | 1121-1139 | 491 | uuGGAAGAAAcuAcuuGGGTsT | 492 | CccAAGuAGUUUCUUCcAATsT |
| AD-12780 | b | 1121-1139 | 493 | uuGGAAGAAAcuAcuuGGGTsT | 494 | CCcAAGuAGUUUCUUCcAATsT |
| AD-12688 | a | 4357-4375 | 495 | AuGAAGAccuGuuuuGccATsT | 496 | UgGcAAAAcAGGUCUUcAUTsT |
| AD-12781 | b | 4357-4375 | 497 | AuGAAGAccuGuuuuGccATsT | 498 | UGGcAAAAcAGGUCUUcAUTsT |
| AD-12689 | a | 4358-4376 | 499 | GAuGAAGAccuGuuuuGccTsT | 500 | GgcAAAAcAGGUCUUcAUCTsT |
| AD-12782 | b | 4358-4376 | 501 | GAuGAAGAccuGuuuuGccTsT | 502 | GGcAAAAcAGGUCUUcAUCTsT |
| AD-12830 | c | 4358-4376 | 503 | GauGAAGAccuGuuuuGccTsT | 504 | GGcAAAAcAGGUCUUcAUCTsT |
| AD-12870 | d | 4358-4376 | 505 | GauGAAGAccuGuuuuGccTsT | 506 | GgcAAAAcAGGUCUUcAUCTsT |
| AD-12690 | a | 4360-4378 | 507 | GGGAuGAAGAccuGuuuuGTsT | 508 | caAAAcAGGUCUUcAUCCCTsT |
| AD-12783 | b | 4360-4378 | 509 | GGGAuGAAGAccuGuuuuGTsT | 510 | cAAAAcAGGUCUUcAUCCCTsT |
| AD-12831 | c | 4360-4378 | 511 | GgGAuGAAGAccuGuuuuGTsT | 512 | cAAAAcAGGUCUUcAUCCCTsT |
| AD-12871 | d | 4360-4378 | 513 | GgGAuGAAGAccuGuuuuGTsT | 514 | caAAAcAGGUCUUcAUCCCTsT |

Description of chemistries:
a exo/endo-light + 2'-O-methyl in position 2 of antisense
b exo/endo-light: sense strand: dTsdT + 2'OMe@ all Py; antisense strand: dTsdT + 2'OMe@ Py in uA,cA
c exo/endo-light + 2'-O-methyl in position 2 of sense
d exo/endo-light + 2'-O-methyl in position 2 of sense and antisense TABLE 1b-2

| duplex name | Residual luciferase activity (relative to control siRNA treated cells) | SD of residual luciferase activity | Residual luciferase activity +/− SD | Relative siRNA activity (normalized to positive control luc-siRNA) | SD of relative siRNA activity | Relative siRNA activity +/− SD |
|---|---|---|---|---|---|---|
| AD-12598 | 91 | 11 | 91 ± 11% | 9 | 2 | 9 ± 2% |
| AD-12708 | 32 | 5 | 32 ± 5% | 76 | 17 | 76 ± 17% |
| AD-12599 | 25 | 6 | 25 ± 6% | 79 | 13 | 79 ± 13% |
| AD-12709 | 16 | 4 | 16 ± 4% | 97 | 26 | 97 ± 26% |
| AD-12600 | 79 | 9 | 79 ± 9% | 21 | 3 | 21 ± 3% |
| AD-12710 | 25 | 4 | 25 ± 4% | 85 | 24 | 85 ± 24% |
| AD-12784 | 23 | 2 | 23 ± 2% | 87 | 14 | 87 ± 14% |
| AD-12832 | 84 | 11 | 84 ± 11% | 18 | 4 | 18 ± 4% |
| AD-12601 | 102 | 8 | 102 ± 8% | −6 | 1 | −6 ± 1% |
| AD-12785 | 95 | 10 | 95 ± 10% | 6 | 1 | 6 ± 1% |
| AD-12602 | 107 | 9 | 107 ± 9% | −11 | 2 | −11 ± 2% |
| AD-12711 | 70 | 4 | 70 ± 4% | 34 | 3 | 34 ± 3% |
| AD-12786 | 69 | 8 | 69 ± 8% | 35 | 7 | 35 ± 7% |
| AD-12833 | 94 | 8 | 94 ± 8% | 7 | 1 | 7 ± 1% |
| AD-12603 | 100 | 9 | 100 ± 9% | −4 | 1 | −4 ± 1% |
| AD-12712 | 27 | 5 | 27 ± 5% | 82 | 16 | 82 ± 16% |
| AD-12604 | 15 | 2 | 15 ± 2% | 94 | 13 | 94 ± 13% |
| AD-12605 | 94 | 5 | 94 ± 5% | 7 | 0 | 7 ± 0% |
| AD-12713 | 61 | 10 | 61 ± 10% | 41 | 8 | 41 ± 8% |
| AD-12787 | 55 | 6 | 55 ± 6% | 47 | 6 | 47 ± 6% |
| AD-12834 | 92 | 16 | 92 ± 16% | 8 | 2 | 8 ± 2% |
| AD-12606 | 78 | 3 | 78 ± 3% | 25 | 1 | 25 ± 1% |
| AD-12714 | 63 | 6 | 63 ± 6% | 42 | 5 | 42 ± 5% |
| AD-12607 | 101 | 9 | 101 ± 9% | −1 | 0 | −1 ± 0% |
| AD-12715 | 101 | 5 | 101 ± 5% | −1 | 0 | −1 ± 0% |
| AD-12788 | 85 | 18 | 85 ± 18% | 15 | 4 | 15 ± 4% |
| AD-12835 | 95 | 9 | 95 ± 9% | 6 | 1 | 6 ± 1% |
| AD-12608 | 103 | 13 | 103 ± 13% | −3 | 0 | −3 ± 0% |
| AD-12716 | 81 | 9 | 81 ± 9% | 22 | 3 | 22 ± 3% |
| AD-12789 | 61 | 4 | 61 ± 4% | 44 | 4 | 44 ± 4% |
| AD-12836 | 103 | 11 | 103 ± 11% | −3 | 0 | −3 ± 0% |
| AD-12609 | 108 | 19 | 108 ± 19% | −9 | 2 | −9 ± 2% |
| AD-12717 | 94 | 17 | 94 ± 17% | 7 | 1 | 7 ± 1% |
| AD-12610 | 88 | 9 | 88 ± 9% | 14 | 2 | 14 ± 2% |
| AD-12718 | 39 | 4 | 39 ± 4% | 64 | 8 | 64 ± 8% |
| AD-12611 | 38 | 6 | 38 ± 6% | 69 | 12 | 69 ± 12% |
| AD-12719 | 26 | 4 | 26 ± 4% | 78 | 13 | 78 ± 13% |
| AD-12790 | 17 | 3 | 17 ± 3% | 87 | 18 | 87 ± 18% |
| AD-12837 | 22 | 4 | 22 ± 4% | 81 | 16 | 81 ± 16% |
| AD-12612 | 100 | 6 | 100 ± 6% | 0 | 0 | 0 ± 0% |
| AD-12720 | 73 | 6 | 73 ± 6% | 28 | 3 | 28 ± 3% |
| AD-12791 | 46 | 9 | 46 ± 9% | 57 | 12 | 57 ± 12% |
| AD-12838 | 97 | 15 | 97 ± 15% | 3 | 1 | 3 ± 1% |
| AD-12613 | 26 | 4 | 26 ± 4% | 82 | 15 | 82 ± 15% |
| AD-12721 | 10 | 1 | 10 ± 1% | 94 | 12 | 94 ± 12% |
| AD-12792 | 10 | 3 | 10 ± 3% | 94 | 40 | 94 ± 40% |
| AD-12839 | 22 | 3 | 22 ± 3% | 81 | 12 | 81 ± 12% |
| AD-12614 | 15 | 5 | 15 ± 5% | 94 | 38 | 94 ± 38% |
| AD-12722 | 6 | 1 | 6 ± 1% | 98 | 26 | 98 ± 26% |
| AD-12615 | 93 | 4 | 93 ± 4% | 8 | 0 | 8 ± 0% |
| AD-12616 | 95 | 4 | 95 ± 4% | 5 | 0 | 5 ± 0% |
| AD-12723 | 73 | 7 | 73 ± 7% | 30 | 3 | 30 ± 3% |
| AD-12617 | 88 | 10 | 88 ± 10% | 13 | 2 | 13 ± 2% |
| AD-12618 | 42 | 7 | 42 ± 7% | 60 | 7 | 60 ± 7% |
| AD-12724 | 21 | 5 | 21 ± 5% | 89 | 32 | 89 ± 32% |
| AD-12619 | 95 | 7 | 95 ± 7% | 6 | 1 | 6 ± 1% |
| AD-12725 | 71 | 2 | 71 ± 2% | 30 | 1 | 30 ± 1% |
| AD-12793 | 54 | 7 | 54 ± 7% | 48 | 7 | 48 ± 7% |
| AD-12840 | 94 | 9 | 94 ± 9% | 7 | 1 | 7 ± 1% |
| AD-12620 | 106 | 7 | 106 ± 7% | −8 | 1 | −8 ± 1% |
| AD-12726 | 100 | 7 | 100 ± 7% | 0 | 0 | 0 ± 0% |
| AD-12621 | 107 | 9 | 107 ± 9% | −7 | 1 | −7 ± 1% |
| AD-12727 | 47 | 4 | 47 ± 4% | 60 | 8 | 60 ± 8% |
| AD-12794 | 40 | 8 | 40 ± 8% | 67 | 20 | 67 ± 20% |
| AD-12841 | 78 | 13 | 78 ± 13% | 25 | 8 | 25 ± 8% |
| AD-12622 | 16 | 4 | 16 ± 4% | 92 | 29 | 92 ± 29% |
| AD-12728 | 25 | 6 | 25 ± 6% | 84 | 29 | 84 ± 29% |
| AD-12795 | 23 | 3 | 23 ± 3% | 86 | 20 | 86 ± 20% |
| AD-12842 | 19 | 4 | 19 ± 4% | 91 | 20 | 91 ± 20% |
| AD-12623 | 103 | 9 | 103 ± 9% | −3 | 0 | −3 ± 0% |
| AD-12729 | 84 | 8 | 84 ± 8% | 17 | 2 | 17 ± 2% |
| AD-12624 | 31 | 4 | 31 ± 4% | 77 | 12 | 77 ± 12% |
| AD-12730 | 18 | 1 | 18 ± 1% | 85 | 3 | 85 ± 3% |
| AD-12625 | 94 | 10 | 94 ± 10% | 5 | 1 | 5 ± 1% |
| AD-12731 | 57 | 4 | 57 ± 4% | 48 | 4 | 48 ± 4% |

TABLE 1b-2-continued

| duplex name | Residual luciferase activity (relative to control siRNA treated cells) | SD of residual luciferase activity | Residual luciferase activity +/− SD | Relative siRNA activity (normalized to positive control luc-siRNA) | SD of relative siRNA activity | Relative siRNA activity +/− SD |
|---|---|---|---|---|---|---|
| AD-12626 | 99 | 7 | 99 ± 7% | 0 | 0 | 0 ± 0% |
| AD-12732 | 82 | 5 | 82 ± 5% | 20 | 1 | 20 ± 1% |
| AD-12627 | 80 | 6 | 80 ± 6% | 22 | 2 | 22 ± 2% |
| AD-12733 | 65 | 6 | 65 ± 6% | 39 | 4 | 39 ± 4% |
| AD-12628 | 81 | 6 | 81 ± 6% | 21 | 2 | 21 ± 2% |
| AD-12734 | 82 | 7 | 82 ± 7% | 21 | 2 | 21 ± 2% |
| AD-12629 | 113 | 11 | 113 ± 11% | −14 | 2 | −14 ± 2% |
| AD-12735 | 90 | 9 | 90 ± 9% | 11 | 1 | 11 ± 1% |
| AD-12796 | 92 | 8 | 92 ± 8% | 9 | 1 | 9 ± 1% |
| AD-12843 | 117 | 7 | 117 ± 7% | −19 | 1 | −19 ± 1% |
| AD-12630 | 124 | 3 | 124 ± 3% | −27 | 1 | −27 ± 1% |
| AD-12736 | 85 | 4 | 85 ± 4% | 16 | 1 | 16 ± 1% |
| AD-12797 | 52 | 1 | 52 ± 1% | 53 | 1 | 53 ± 1% |
| AD-12844 | 96 | 4 | 96 ± 4% | 5 | 0 | 5 ± 0% |
| AD-12631 | 110 | 11 | 110 ± 11% | −12 | 1 | −12 ± 1% |
| AD-12737 | 115 | 13 | 115 ± 13% | −17 | 2 | −17 ± 2% |
| AD-12632 | 106 | 2 | 106 ± 2% | −7 | 0 | −7 ± 0% |
| AD-12633 | 107 | 12 | 107 ± 12% | −8 | 1 | −8 ± 1% |
| AD-12738 | 88 | 5 | 88 ± 5% | 14 | 1 | 14 ± 1% |
| AD-12634 | 79 | 5 | 79 ± 5% | 24 | 1 | 24 ± 1% |
| AD-12739 | 69 | 8 | 69 ± 8% | 35 | 6 | 35 ± 6% |
| AD-12635 | 75 | 8 | 75 ± 8% | 25 | 6 | 25 ± 6% |
| AD-12740 | 65 | 8 | 65 ± 8% | 40 | 8 | 40 ± 8% |
| AD-12798 | 56 | 4 | 56 ± 4% | 50 | 6 | 50 ± 6% |
| AD-12845 | 74 | 6 | 74 ± 6% | 30 | 3 | 30 ± 3% |
| AD-12636 | 89 | 8 | 89 ± 8% | 9 | 1 | 9 ± 1% |
| AD-12741 | 31 | 4 | 31 ± 4% | 78 | 14 | 78 ± 14% |
| AD-12637 | 16 | 2 | 16 ± 2% | 93 | 14 | 93 ± 14% |
| AD-12742 | 18 | 3 | 18 ± 3% | 85 | 14 | 85 ± 14% |
| AD-12799 | 18 | 4 | 18 ± 4% | 86 | 22 | 86 ± 22% |
| AD-12846 | 15 | 2 | 15 ± 2% | 89 | 14 | 89 ± 14% |
| AD-12638 | 95 | 6 | 95 ± 6% | 5 | 0 | 5 ± 0% |
| AD-12743 | 23 | 4 | 23 ± 4% | 81 | 15 | 81 ± 15% |
| AD-12800 | 14 | 1 | 14 ± 1% | 90 | 10 | 90 ± 10% |
| AD-12847 | 90 | 12 | 90 ± 12% | 10 | 2 | 10 ± 2% |
| AD-12639 | 113 | 11 | 113 ± 11% | −15 | 2 | −15 ± 2% |
| AD-12744 | 42 | 4 | 42 ± 4% | 60 | 7 | 60 ± 7% |
| AD-12801 | 34 | 3 | 34 ± 3% | 68 | 8 | 68 ± 8% |
| AD-12848 | 114 | 3 | 114 ± 3% | −14 | 0 | −14 ± 0% |
| AD-12640 | 96 | 11 | 96 ± 11% | 4 | 1 | 4 ± 1% |
| AD-12745 | 52 | 7 | 52 ± 7% | 53 | 8 | 53 ± 8% |
| AD-12802 | 74 | 9 | 74 ± 9% | 29 | 4 | 29 ± 4% |
| AD-12849 | 111 | 5 | 111 ± 5% | −12 | 1 | −12 ± 1% |
| AD-12641 | 103 | 8 | 103 ± 8% | −3 | 0 | −3 ± 0% |
| AD-12803 | 94 | 13 | 94 ± 13% | 6 | 1 | 6 ± 1% |
| AD-12642 | 105 | 3 | 105 ± 3% | −6 | 0 | −6 ± 0% |
| AD-12746 | 100 | 9 | 100 ± 9% | 0 | 0 | 0 ± 0% |
| AD-12643 | 33 | 4 | 33 ± 4% | 74 | 10 | 74 ± 10% |
| AD-12747 | 21 | 3 | 21 ± 3% | 83 | 13 | 83 ± 13% |
| AD-12804 | 25 | 4 | 25 ± 4% | 78 | 14 | 78 ± 14% |
| AD-12850 | 28 | 4 | 28 ± 4% | 75 | 11 | 75 ± 11% |
| AD-12644 | 82 | 7 | 82 ± 7% | 20 | 2 | 20 ± 2% |
| AD-12748 | 25 | 4 | 25 ± 4% | 78 | 14 | 78 ± 14% |
| AD-12805 | 23 | 7 | 23 ± 7% | 80 | 30 | 80 ± 30% |
| AD-12851 | 61 | 7 | 61 ± 7% | 41 | 5 | 41 ± 5% |
| AD-12645 | 112 | 6 | 112 ± 6% | −14 | 1 | −14 ± 1% |
| AD-12749 | 86 | 10 | 86 ± 10% | 16 | 2 | 16 ± 2% |
| AD-12646 | 94 | 10 | 94 ± 10% | 6 | 1 | 6 ± 1% |
| AD-12750 | 93 | 11 | 93 ± 11% | 7 | 1 | 7 ± 1% |
| AD-12806 | 77 | 8 | 77 ± 8% | 24 | 3 | 24 ± 3% |
| AD-12852 | 96 | 4 | 96 ± 4% | 5 | 0 | 5 ± 0% |
| AD-12647 | 27 | 3 | 27 ± 3% | 81 | 11 | 81 ± 11% |
| AD-12751 | 29 | 6 | 29 ± 6% | 74 | 19 | 74 ± 19% |
| AD-12807 | 31 | 2 | 31 ± 2% | 72 | 6 | 72 ± 6% |
| AD-12853 | 26 | 3 | 26 ± 3% | 78 | 11 | 78 ± 11% |
| AD-12648 | 81 | 9 | 81 ± 9% | 17 | 3 | 17 ± 3% |
| AD-12649 | 92 | 9 | 92 ± 9% | 8 | 1 | 8 ± 1% |
| AD-12752 | 71 | 9 | 71 ± 9% | 30 | 5 | 30 ± 5% |
| AD-12650 | 81 | 2 | 81 ± 2% | 21 | 1 | 21 ± 1% |
| AD-12753 | 57 | 1 | 57 ± 1% | 48 | 1 | 48 ± 1% |
| AD-12808 | 52 | 4 | 52 ± 4% | 54 | 5 | 54 ± 5% |
| AD-12854 | 77 | 5 | 77 ± 5% | 26 | 2 | 26 ± 2% |
| AD-12651 | 89 | 6 | 89 ± 6% | 13 | 1 | 13 ± 1% |
| AD-12754 | 88 | 7 | 88 ± 7% | 12 | 1 | 12 ± 1% |
| AD-12809 | 67 | 6 | 67 ± 6% | 35 | 4 | 35 ± 4% |

TABLE 1b-2-continued

| duplex name | Residual luciferase activity (relative to control siRNA treated cells) | SD of residual luciferase activity | Residual luciferase activity +/− SD | Relative siRNA activity (normalized to positive control luc-siRNA) | SD of relative siRNA activity | Relative siRNA activity +/− SD |
|---|---|---|---|---|---|---|
| AD-12855 | 88 | 10 | 88 ± 10% | 12 | 2 | 12 ± 2% |
| AD-12652 | 91 | 2 | 91 ± 2% | 10 | 0 | 10 ± 0% |
| AD-12755 | 40 | 3 | 40 ± 3% | 67 | 6 | 67 ± 6% |
| AD-12810 | 35 | 1 | 35 ± 1% | 72 | 3 | 72 ± 3% |
| AD-12856 | 75 | 8 | 75 ± 8% | 28 | 4 | 28 ± 4% |
| AD-12653 | 79 | 8 | 79 ± 8% | 23 | 3 | 23 ± 3% |
| AD-12756 | 17 | 5 | 17 ± 5% | 86 | 27 | 86 ± 27% |
| AD-12654 | 97 | 6 | 97 ± 6% | 3 | 0 | 3 ± 0% |
| AD-12811 | 74 | 5 | 74 ± 5% | 27 | 2 | 27 ± 2% |
| AD-12655 | 46 | 6 | 46 ± 6% | 59 | 9 | 59 ± 9% |
| AD-12757 | 14 | 0 | 14 ± 0% | 89 | 2 | 89 ± 2% |
| AD-12812 | 12 | 3 | 12 ± 3% | 92 | 28 | 92 ± 28% |
| AD-12857 | 35 | 7 | 35 ± 7% | 70 | 17 | 70 ± 17% |
| AD-12656 | 10 | 3 | 10 ± 3% | 99 | 33 | 99 ± 33% |
| AD-12813 | 9 | 1 | 9 ± 1% | 95 | 18 | 95 ± 18% |
| AD-12657 | 108 | 1 | 108 ± 1% | −9 | 0 | −9 ± 0% |
| AD-12814 | 101 | 4 | 101 ± 4% | −1 | 0 | −1 ± 0% |
| AD-12658 | 98 | 9 | 98 ± 9% | 2 | 0 | 2 ± 0% |
| AD-12659 | 83 | 4 | 83 ± 4% | 18 | 1 | 18 ± 1% |
| AD-12758 | 80 | 14 | 80 ± 14% | 21 | 4 | 21 ± 4% |
| AD-12815 | 25 | 3 | 25 ± 3% | 79 | 11 | 79 ± 11% |
| AD-12858 | 67 | 4 | 67 ± 4% | 35 | 2 | 35 ± 2% |
| AD-12660 | 95 | 11 | 95 ± 11% | 8 | 3 | 8 ± 3% |
| AD-12759 | 66 | 7 | 66 ± 7% | 39 | 6 | 39 ± 6% |
| AD-12661 | 34 | 2 | 34 ± 2% | 73 | 5 | 73 ± 5% |
| AD-12760 | 10 | 3 | 10 ± 3% | 94 | 30 | 94 ± 30% |
| AD-12816 | 12 | 4 | 12 ± 4% | 92 | 37 | 92 ± 37% |
| AD-12859 | 33 | 1 | 33 ± 1% | 72 | 2 | 72 ± 2% |
| AD-12662 | 92 | 7 | 92 ± 7% | 7 | 1 | 7 ± 1% |
| AD-12817 | 91 | 11 | 91 ± 11% | 10 | 2 | 10 ± 2% |
| AD-12663 | 99 | 10 | 99 ± 10% | 3 | 1 | 3 ± 1% |
| AD-12761 | 20 | 5 | 20 ± 5% | 89 | 22 | 89 ± 22% |
| AD-12818 | 20 | 4 | 20 ± 4% | 90 | 20 | 90 ± 20% |
| AD-12860 | 93 | 11 | 93 ± 11% | 8 | 1 | 8 ± 1% |
| AD-12664 | 93 | 9 | 93 ± 9% | 6 | 2 | 6 ± 2% |
| AD-12665 | 94 | 8 | 94 ± 8% | 10 | 1 | 10 ± 1% |
| AD-12762 | 58 | 8 | 58 ± 8% | 47 | 10 | 47 ± 10% |
| AD-12819 | 49 | 6 | 49 ± 6% | 58 | 9 | 58 ± 9% |
| AD-12861 | 93 | 8 | 93 ± 8% | 8 | 1 | 8 ± 1% |
| AD-12666 | 30 | 5 | 30 ± 5% | 76 | 18 | 76 ± 18% |
| AD-12763 | 25 | 2 | 25 ± 2% | 84 | 9 | 84 ± 9% |
| AD-12667 | 65 | 10 | 65 ± 10% | 38 | 7 | 38 ± 7% |
| AD-12764 | 34 | 7 | 34 ± 7% | 69 | 17 | 69 ± 17% |
| AD-12668 | 34 | 4 | 34 ± 4% | 73 | 10 | 73 ± 10% |
| AD-12765 | 13 | 3 | 13 ± 3% | 91 | 22 | 91 ± 22% |
| AD-12820 | 11 | 2 | 11 ± 2% | 93 | 17 | 93 ± 17% |
| AD-12862 | 19 | 4 | 19 ± 4% | 87 | 22 | 87 ± 22% |
| AD-12669 | 22 | 3 | 22 ± 3% | 87 | 12 | 87 ± 12% |
| AD-12766 | 11 | 4 | 11 ± 4% | 93 | 39 | 93 ± 39% |
| AD-12670 | 45 | 3 | 45 ± 3% | 61 | 5 | 61 ± 5% |
| AD-12767 | 10 | 3 | 10 ± 3% | 94 | 31 | 94 ± 31% |
| AD-12821 | 12 | 1 | 12 ± 1% | 92 | 13 | 92 ± 13% |
| AD-12863 | 41 | 4 | 41 ± 4% | 64 | 8 | 64 ± 8% |
| AD-12671 | 83 | 9 | 83 ± 9% | 19 | 2 | 19 ± 2% |
| AD-12822 | 74 | 7 | 74 ± 7% | 29 | 3 | 29 ± 3% |
| AD-12672 | 52 | 7 | 52 ± 7% | 54 | 9 | 54 ± 9% |
| AD-12768 | 28 | 3 | 28 ± 3% | 81 | 12 | 81 ± 12% |
| AD-12673 | 56 | 5 | 56 ± 5% | 49 | 5 | 49 ± 5% |
| AD-12769 | 36 | 2 | 36 ± 2% | 72 | 5 | 72 ± 5% |
| AD-12823 | 33 | 2 | 33 ± 2% | 75 | 5 | 75 ± 5% |
| AD-12864 | 49 | 7 | 49 ± 7% | 57 | 10 | 57 ± 10% |
| AD-12674 | 90 | 9 | 90 ± 9% | 11 | 1 | 11 ± 1% |
| AD-12770 | 45 | 6 | 45 ± 6% | 61 | 9 | 61 ± 9% |
| AD-12675 | 45 | 5 | 45 ± 5% | 62 | 8 | 62 ± 8% |
| AD-12676 | 47 | 6 | 47 ± 6% | 59 | 9 | 59 ± 9% |
| AD-12771 | 31 | 4 | 31 ± 4% | 77 | 11 | 77 ± 11% |
| AD-12824 | 31 | 3 | 31 ± 3% | 77 | 10 | 77 ± 10% |
| AD-12865 | 43 | 7 | 43 ± 7% | 64 | 12 | 64 ± 12% |
| AD-12677 | 23 | 4 | 23 ± 4% | 86 | 16 | 86 ± 16% |
| AD-12825 | 22 | 4 | 22 ± 4% | 87 | 16 | 87 ± 16% |
| AD-12678 | 102 | 8 | 102 ± 8% | −2 | 0 | −2 ± 0% |
| AD-12772 | 101 | 13 | 101 ± 13% | −1 | 0 | −1 ± 0% |
| AD-12826 | 99 | 1 | 99 ± 1% | 1 | 0 | 1 ± 0% |
| AD-12866 | 91 | 7 | 91 ± 7% | 10 | 1 | 10 ± 1% |
| AD-12679 | 81 | 8 | 81 ± 8% | 21 | 2 | 21 ± 2% |

TABLE 1b-2-continued

| duplex name | Residual luciferase activity (relative to control siRNA treated cells) | SD of residual luciferase activity | Residual luciferase activity +/− SD | Relative siRNA activity (normalized to positive control luc-siRNA) | SD of relative siRNA activity | Relative siRNA activity +/− SD |
|---|---|---|---|---|---|---|
| AD-12773 | 11 | 2 | 11 ± 2% | 93 | 19 | 93 ± 19% |
| AD-12680 | 17 | 3 | 17 ± 3% | 92 | 17 | 92 ± 17% |
| AD-12774 | 15 | 2 | 15 ± 2% | 89 | 17 | 89 ± 17% |
| AD-12827 | 11 | 2 | 11 ± 2% | 93 | 18 | 93 ± 18% |
| AD-12867 | 15 | 3 | 15 ± 3% | 91 | 22 | 91 ± 22% |
| AD-12681 | 28 | 3 | 28 ± 3% | 79 | 10 | 79 ± 10% |
| AD-12775 | 8 | 1 | 8 ± 1% | 95 | 19 | 95 ± 19% |
| AD-12682 | 43 | 6 | 43 ± 6% | 63 | 9 | 63 ± 9% |
| AD-12776 | 23 | 5 | 23 ± 5% | 80 | 19 | 80 ± 19% |
| AD-12828 | 23 | 5 | 23 ± 5% | 80 | 20 | 80 ± 20% |
| AD-12868 | 25 | 4 | 25 ± 4% | 81 | 16 | 81 ± 16% |
| AD-12683 | 17 | 2 | 17 ± 2% | 91 | 15 | 91 ± 15% |
| AD-12777 | 11 | 2 | 11 ± 2% | 92 | 22 | 92 ± 22% |
| AD-12829 | 12 | 1 | 12 ± 1% | 92 | 11 | 92 ± 11% |
| AD-12869 | 19 | 3 | 19 ± 3% | 87 | 16 | 87 ± 16% |
| AD-12684 | 87 | 12 | 87 ± 12% | 14 | 2 | 14 ± 2% |
| AD-12778 | 41 | 4 | 41 ± 4% | 66 | 8 | 66 ± 8% |
| AD-12685 | 35 | 1 | 35 ± 1% | 72 | 1 | 72 ± 1% |
| AD-12686 | 68 | 5 | 68 ± 5% | 36 | 3 | 36 ± 3% |
| AD-12779 | 58 | 5 | 58 ± 5% | 47 | 5 | 47 ± 5% |
| AD-12687 | 73 | 8 | 73 ± 8% | 30 | 4 | 30 ± 4% |
| AD-12780 | 62 | 8 | 62 ± 8% | 42 | 7 | 42 ± 7% |
| AD-12688 | 18 | 1 | 18 ± 1% | 91 | 4 | 91 ± 4% |
| AD-12781 | 11 | 3 | 11 ± 3% | 93 | 33 | 93 ± 33% |
| AD-12689 | 96 | 4 | 96 ± 4% | 4 | 0 | 4 ± 0% |
| AD-12782 | 45 | 7 | 45 ± 7% | 58 | 10 | 58 ± 10% |
| AD-12830 | 15 | 3 | 15 ± 3% | 89 | 19 | 89 ± 19% |
| AD-12870 | 51 | 3 | 51 ± 3% | 52 | 4 | 52 ± 4% |
| AD-12690 | 93 | 6 | 93 ± 6% | 8 | 1 | 8 ± 1% |
| AD-12783 | 36 | 3 | 36 ± 3% | 66 | 7 | 66 ± 7% |
| AD-12831 | 27 | 2 | 27 ± 2% | 76 | 7 | 76 ± 7% |
| AD-12871 | 81 | 18 | 81 ± 18% | 21 | 5 | 21 ± 5% |

We claim:

1. A double-stranded ribonucleic acid (dsRNA) for inhibiting the expression of a human JC virus genome in a cell, wherein said dsRNA comprises a sense strand and an antisense strand that together form a region of complementarity, and wherein said sense strand consists of UGUUGAAUG-UUGGGUUCCUTT (SEQ ID NO: 936) and said antisense strand consists of AGGAACCCAACAUUCAACATT (SEQ ID NO: 937).

2. The dsRNA of claim 1, wherein at least one nucleotide of said sense strand or said antisense strand is a modified nucleotide.

3. The dsRNA of claim 2, wherein said modified nucleotide is chosen from the group of: a 2′-O-methyl modified nucleotide, a nucleotide comprising a 5′-phosphorothioate group, and a terminal nucleotide linked to a cholesteryl derivative or dodecanoic acid bisdecylamide group.

4. The dsRNA of claim 2, wherein said modified nucleotide is chosen from the group of: a 2′-deoxy-2′-fluoro modified nucleotide, a 2′-deoxy-modified nucleotide, a locked nucleotide, an abasic nucleotide, 2′-amino-modified nucleotide, 2′-alkyl-modified nucleotide, morpholino nucleotide, a phosphoramidate, and a non-natural base comprising nucleotide.

5. A cell comprising the dsRNA of claim 1.

6. A pharmaceutical composition for inhibiting the expression of a gene from a JC Virus in an organism, comprising the dsRNA of claim 1 and a pharmaceutically acceptable carrier.

7. The pharmaceutical composition of claim 6, wherein the pharmaceutically acceptable carrier comprises a lipid.

8. A method for inhibiting the expression of a gene from a JC Virus in a cell, the method comprising:

(a) introducing into the cell the dsRNA of claim 1; and
(b) maintaining the cell produced in step (a) for a time sufficient to obtain degradation of the mRNA transcript of a gene from a JC Virus, thereby inhibiting expression of a gene from a JC Virus in the cell.

9. A method of inhibiting replication of a JC virus in a patient comprising administering to the patient an amount of the dsRNA of claim 1 effective to inhibit replication of the virus.

10. A vector for inhibiting the expression of a gene from a JC Virus in a cell, said vector being capable of a) expressing the dsRNA of claim 1 as a single RNA molecule with two complementary regions; or alternatively b) expressing each strand of the dsRNA of claim 1 under the control of a separate promoter.

11. A cell comprising the vector of claim 10.

12. The dsRNA of claim 1, wherein said sense strand consists of uGuuGAAuGuuGGGuuccuTsT (SEQ ID NO: 131), and wherein said antisense strand consists of AgGAAC-CcAAcAUUcAAcATsT (SEQ ID NO:132), wherein u is a uridine ribonucleotide having a 2′-O-methyl modification, and wherein c is a cytidine ribonucleotide having a 2′-O-methyl modification, and wherein g is a guanosine ribonucleotide having a 2′-O-methyl modification and s is a phosphorothioate between nucleotides 20 and 21.

13. A pharmaceutical composition for inhibiting the expression of a gene from a JC Virus in an organism, comprising the dsRNA of claim 12 and a pharmaceutically acceptable carrier.

14. The pharmaceutical composition of claim 13, wherein the pharmaceutically acceptable carrier comprises a lipid.

15. A method for inhibiting the expression of a gene from a JC Virus in a cell, the method comprising:
(a) introducing into the cell the dsRNA of claim 12; and
(b) maintaining the cell produced in step (a) for a time sufficient to obtain degradation of the mRNA transcript of a gene from a JC Virus, thereby inhibiting expression of a gene from a JC Virus in the cell.

16. A method of inhibiting replication of a JC virus in a patient comprising administering to the patient an amount of the dsRNA of claim 12 effective to inhibit replication of the virus.

* * * * *